(12) United States Patent
Kesteleyn et al.

(10) Patent No.: US 10,646,469 B2
(45) Date of Patent: May 12, 2020

(54) SUBSTITUTED INDOLE DERIVATIVES AS DENGUE VIRAL REPLICATION INHIBITORS

(71) Applicants: Janssen Pharmaceuticals, Inc., Titusville, NJ (US); Katholieke Universiteit Leuven, Leuven (BE)

(72) Inventors: Bart Rudolf Romanie Kesteleyn, Berlare (BE); Jean-François Bonfanti, Ande (FR); Pierre Jean-Marie Bernard Raboisson, Rosieres (BE); Dorothée Alice Marie-Eve Bardiot, Heverlee (BE); Arnaud Didier M Marchand, Bierbeek (BE)

(73) Assignees: Janssen Pharmaceuticals, Inc., Titusville, NJ (US); Katholieke Universiteit Leuven, Leuven (BE)

( * ) Notice: Subject to any disclaimer, the term of this patent is extended or adjusted under 35 U.S.C. 154(b) by 0 days.

(21) Appl. No.: 16/087,800

(22) PCT Filed: Mar. 31, 2017

(86) PCT No.: PCT/EP2017/057660
§ 371 (c)(1),
(2) Date: Sep. 24, 2018

(87) PCT Pub. No.: WO2017/167950
PCT Pub. Date: Oct. 5, 2017

(65) Prior Publication Data
US 2019/0274999 A1 Sep. 12, 2019

(30) Foreign Application Priority Data
Mar. 31, 2016 (EP) .................... 16163312

(51) Int. Cl.
*C07D 209/12* (2006.01)
*A61K 31/404* (2006.01)
*A61P 31/14* (2006.01)
*C07D 209/32* (2006.01)
*C07D 209/14* (2006.01)

(52) U.S. Cl.
CPC .......... *A61K 31/404* (2013.01); *A61P 31/14* (2018.01); *C07D 209/12* (2013.01); *C07D 209/14* (2013.01); *C07D 209/32* (2013.01)

(58) Field of Classification Search
CPC .................................. C07D 209/12
See application file for complete search history.

(56) References Cited

U.S. PATENT DOCUMENTS

| | | | |
|---|---|---|---|
| 7,601,735 B2 | 10/2009 | Tyms et al. |
| 8,524,764 B2 | 9/2013 | Canales et al. |
| 8,884,030 B2 | 11/2014 | Canales et al. |
| 8,993,604 B2 | 3/2015 | Byrd et al. |
| 9,029,376 B2 | 5/2015 | Byrd et al. |
| 9,522,923 B2 | 12/2016 | Richards et al. |
| 9,944,598 B2 | 4/2018 | Kesteleyn et al. |
| 10,029,984 B2 | 7/2018 | Kesteleyn et al. |
| 10,064,870 B2 | 9/2018 | Rajagopalan et al. |
| 10,071,961 B2 | 9/2018 | Vandyck et al. |
| 10,117,850 B2 | 11/2018 | Griffioen et al. |
| 10,206,902 B2 | 2/2019 | Kesteleyn et al. |
| 10,323,026 B2 | 6/2019 | Ikeda et al. |
| 2005/0239821 A1 | 10/2005 | Neyts et al. |
| 2006/0194835 A1 | 8/2006 | Dugourd et al. |
| 2006/0211698 A1 | 9/2006 | Botyanszki et al. |
| 2008/0318338 A1 | 12/2008 | Kamal et al. |
| 2016/0297810 A1 | 10/2016 | Bardiot et al. |
| 2017/0002006 A1 | 1/2017 | Corte et al. |
| 2017/0096429 A1 | 4/2017 | Corte et al. |
| 2017/0281633 A1 | 10/2017 | Boylan et al. |
| 2017/0281766 A1 | 10/2017 | Wiltzius |
| 2017/0283500 A1 | 10/2017 | Wiltzius et al. |
| 2017/0298017 A1 | 10/2017 | Kesteleyn et al. |
| 2018/0256544 A1 | 9/2018 | Kesteleyn et al. |
| 2018/0256545 A1 | 9/2018 | Kesteleyn et al. |
| 2018/0346419 A1 | 12/2018 | Kesteleyn et al. |
| 2019/0104738 A1 | 4/2019 | Narine et al. |
| 2019/0112266 A1 | 4/2019 | Kesteleyn et al. |
| 2019/0183931 A1 | 6/2019 | Bakker et al. |

FOREIGN PATENT DOCUMENTS

| | | | |
|---|---|---|---|
| WO | 02089780 A2 | 11/2002 |
| WO | 03050295 A2 | 6/2003 |
| WO | 2009149054 A1 | 12/2009 |
| WO | WO 2010/021878 A1 | 2/2010 |
| WO | 2011037643 A2 | 3/2011 |
| WO | 2011088303 A1 | 7/2011 |
| WO | WO 2013/045516 A1 | 4/2013 |
| WO | 2016050841 A1 | 4/2016 |
| WO | 2016053455 A1 | 4/2016 |
| WO | 2017079216 A1 | 5/2017 |
| WO | 2017167832 A1 | 10/2017 |
| WO | 2017167950 A1 | 10/2017 |
| WO | 2017167952 A1 | 10/2017 |
| WO | 2017167953 A1 | 10/2017 |

(Continued)

OTHER PUBLICATIONS

Prasad L. Polavarapu, et al., Intrinsic Rotation and Molecular Structure, Chirality 15: S143-S149 (2003).

(Continued)

*Primary Examiner* — Shawquia Jackson
(74) *Attorney, Agent, or Firm* — Amster, Rothstein & Ebenstein LLP

(57) ABSTRACT

The present invention concerns substituted indole derivatives, methods to prevent or treat dengue viral infections by using said compounds and also relates to said compounds for use as a medicine, more preferably for use as a medicine to treat or prevent dengue viral infections. The present invention furthermore relates to pharmaceutical compositions or combination preparations of the compounds, to the compositions or preparations for use as a medicine, more preferably for the prevention or treatment of dengue viral infections. The invention also relates to processes for preparation of the compounds.

7 Claims, No Drawings

Specification includes a Sequence Listing.

(56) References Cited

FOREIGN PATENT DOCUMENTS

| WO | 2017171100 A1 | 10/2017 |
| WO | 2017173206 A1 | 10/2017 |
| WO | 2017173256 A1 | 10/2017 |
| WO | 2017173384 A1 | 10/2017 |
| WO | 2017173410 A1 | 10/2017 |
| WO | 2018178238 A1 | 10/2018 |
| WO | 2018178240 A1 | 10/2018 |
| WO | 2018215315 A1 | 11/2018 |
| WO | 2018215316 A1 | 11/2018 |

OTHER PUBLICATIONS

Ian Stansfield et al., Development of carboxylic acid replacements in indole-N-acetamide inhibitors of hepatitis C virus NS5B polymerase, Bioorganic & Medicinal Chemistry Letters 17 (2007) 5143-5149, ScienceDirect (2007), www.sciencedirect.com, internet.
Boltromeyuk V.V., Obshchaya khimiya (General Chemistry), Minsk, Vysheyshaya shkola, 2012, p. 65) (translation).
Banker, et al., (1996) Modern Pharmaceuticals, 3rd Edition, Revised and Expanded, p. 596.
Wolff et al., Burger's Medicinal Chemistry and Drug Discovery, 5th Ed. part 1, p. 975-977 (1995).
Prevention, Dengue, Centers for Disease Control and Prevention (Sep. 27, 2012) https://www.cdc.govidengue/prevention/index.html, internet.
Lidia Moreira Lima et al., Bioisosterism: A Useful Strategy for Molecular Modification and Drug Design, Current Medicinal Chemistry, Bentham Science Publishers Ltd. (2005) 12, pp. 23-49.
N.C.B.I.: "qHTS for inhibitors of binding or entry into cells for Marburg Virus," Pubchem Bioassay Record AID 540276, Jul. 2011, 13 pages, XP55641386, Retrieved from the Internet: https://pubchem.ncbi.nlm.nih.gov/bioassay/540276.
EP Search Report dated Nov. 19, 2019 from EP Application No. 19183201.3.
"Solvation," Wikipedia, at internet address: https://en.wikipedia.org/wiki/Solvation, web page last edited on Mar. 13, 2019, 6 pages.
Examination Report dated Jan. 7, 2020 from Indian Patent Appln. No. 201727014547.

SEQUENCE LISTING

```
<160> NUMBER OF SEQ ID NOS: 6

<210> SEQ ID NO 1
<211> LENGTH: 19
<212> TYPE: DNA
<213> ORGANISM: Dengue virus

<400> SEQUENCE: 1
cggttagagg agacccctc                                                19

<210> SEQ ID NO 2
<211> LENGTH: 21
<212> TYPE: DNA
<213> ORGANISM: Dengue virus

<400> SEQUENCE: 2
gagacagcag gatctctggt c                                             21
```

```
<210> SEQ ID NO 3
<211> LENGTH: 28
<212> TYPE: DNA
<213> ORGANISM: Dengue virus

<400> SEQUENCE: 3
aaggactaga ggttagagga gaccccccc                                             28

<210> SEQ ID NO 4
<211> LENGTH: 18
<212> TYPE: DNA
<213> ORGANISM: Dengue virus

<400> SEQUENCE: 4
ggccaggtca tcaccatt                                                         18

<210> SEQ ID NO 5
<211> LENGTH: 21
<212> TYPE: DNA
<213> ORGANISM: Dengue virus

<400> SEQUENCE: 5
atgtccacgt cacacttcat g                                                     21

<210> SEQ ID NO 6
<211> LENGTH: 21
<212> TYPE: DNA
<213> ORGANISM: Dengue virus

<400> SEQUENCE: 6
ttccgctgcc ctgaggctct c                                                     21
```

SUBSTITUTED INDOLE DERIVATIVES AS DENGUE VIRAL REPLICATION INHIBITORS

This application is a national stage application of PCT/EP2017/057660, filed Mar. 31, 2017, which claims priority benefit of Application No. EP16163312.8 filed Mar. 31, 2016. The complete disclosures of the aforementioned related patent applications are hereby incorporated herein by reference for all purposes.

The present invention relates to substituted indole derivatives or compounds, methods to prevent or treat dengue viral infections by using said compounds and also relates to said compounds for use as a medicine, more preferably for use as a medicine to treat or prevent dengue viral infections. The present invention furthermore relates to pharmaceutical compositions or combination preparations of the compounds, to the compositions or preparations for use as a medicine, more preferably for the prevention or treatment of dengue viral infections. The invention also relates to processes for preparation of the compounds.

BACKGROUND OF THE INVENTION

Flaviviruses, which are transmitted by mosquitoes or ticks, cause life-threatening infections in man, such as encephalitis and hemorrhagic fever. Four distinct, but closely related serotypes of the flavivirus dengue are known, so-called DENV-1, -2, -3, and -4. Dengue is endemic in most tropical and sub-tropical regions around the world, predominantly in urban and semi-urban areas. According to the World Health Organization (WHO), 2.5 billion people of which 1 billion children are at risk of DENV infection (WHO, 2002). An estimated 50 to 100 million cases of dengue fever [DF], half a million cases of severe dengue disease (i.e. dengue hemorrhagic fever [DHF] and dengue shock syndrome [DSS]), and more than 20,000 deaths occur worldwide each year. DHF has become a leading cause of hospitalization and death amongst children in endemic regions. Altogether, dengue represents the most common cause of arboviral disease. Because of recent large outbreaks in countries situated in Latin America, South-East Asia and the Western Pacific (including Brazil, Puerto Rico, Venezuela, Cambodia, Indonesia, Vietnam, Thailand), numbers of dengue cases have risen dramatically over the past years. Not only is the number of dengue cases increasing as the disease is spreading to new areas, but the outbreaks tend to be more severe.

Although progress is being made in the development of vaccines against dengue with the availability of the Dengvaxia® vaccine, many difficulties are encountered. These include the existence of a phenomenon referred to as antibody-dependent enhancement (ADE). Recovery from an infection by one serotype provides lifelong immunity against that serotype but confers only partial and transient protection against a subsequent infection by one of the other three serotypes.

Following infection with another serotype, pre-existing heterologous antibodies form complexes with the newly infecting dengue virus serotype but do not neutralize the pathogen. Instead, virus entry into cells is believed to be facilitated, resulting in uncontrolled virus replication and higher peak viral titers. In both primary and secondary infections, higher viral titers are associated with more severe dengue disease. Since maternal antibodies can easily pass on to infants by breast feeding, this might be one of the reasons that children are more affected by severe dengue disease than adults. In locations with two or more serotypes circulating simultaneously, also referred to as hyper endemic regions, the risk of serious dengue disease is significantly higher due to an increased risk of experiencing a secondary, more severe infection. Moreover, in a situation of hyperendemicity, the probability of the emergence of more virulent strains is increased, which in turn augments the probability of dengue hemorrhagic fever (DHF) or dengue shock syndrome.

The mosquitoes that carry dengue, including *Aedes aegypti* and *Aedes albopictus* (tiger mosquito), are moving north on the globe. According to the United States (US) Centers for Disease Control and Prevention (CDC), both mosquitoes are currently omnipresent in southern Texas. The spread north of dengue-carrying mosquitoes is not confined to the US, but has also been observed in Europe. Currently, substantial efforts are ongoing for the development and enrollment of vaccines to protect humans against dengue. The main problem however is to develop a vaccine that offers protection against all four serotypes (a tetravalent vaccine) to the same extent.

Dengvaxia®, the dengue vaccine produced by Sanofi Pasteur was first approved in Mexico and has received in the meantime approval in more countries. Nevertheless, the vaccine leaves considerable room for improvement due to limited efficacy, especially against DENV-1 and -2, low efficacy in flavivirus-naïve subjects and the lengthy dosing schedule.

Despite these shortcomings, the vaccine is a game changer in endemic settings as it will offer protection to a large part of the population, but likely not to very young infants, who bear the largest burden of dengue. In addition, the dosing schedule and very limited efficacy in flavivirus-naïve subjects make it unsuitable and likely not worthwhile/cost-effective for travelers from non-endemic areas to dengue-endemic areas. The above mentioned shortcomings of the dengue vaccines are the reason why there is a need for a pre-exposure prophylactic dengue antiviral.

Furthermore, until today, specific antiviral drugs for the treatment or prevention of dengue fever virus infection are not available. Clearly, there is still a great unmet medical need for therapeutics for the prevention or treatment of viral infections in animals, more in particular in humans and especially for viral infections caused by Flaviviruses, more in particular Dengue virus. Compounds with good anti-viral potency, no or low levels of side-effects, a broad spectrum activity against multiple Dengue virus serotypes, a low toxicity and/or good pharmacokinetic or -dynamic properties are highly needed.

The present invention now provides compounds, substituted indole derivatives, which show high potent activity against all four (4) serotypes of the Dengue virus.

WO-2010/021878 discloses 2-phenylpyrrolidine and indoline derivatives as cold menthol receptor antagonists for treatment of inflammatory and central diseases. WO-2013/045516 discloses indole and indoline derivates for use in the treatment of dengue viral infections.

SUMMARY OF THE INVENTION

The present invention is based on the unexpected finding that at least one of the above-mentioned problems can be solved by the current compounds of the invention.

The present invention provides compounds which have been shown to possess potent antiviral activity against all four (4) serotypes currently known. The present invention furthermore demonstrates that these compounds efficiently inhibit proliferation of Dengue virus (DENV). Therefore, these compounds constitute a useful class of potent compounds that can be used in the treatment and/or prevention of viral infections in animals, mammals and humans, more specifically for the treatment and/or prevention of infections with Dengue viruses.

The present invention furthermore relates to the use of such compounds as medicines and to their use for the manufacture of medicaments for treating and/or preventing viral infections, in particular with viruses belonging to the family of the Dengue viruses in animals or mammals, more in particular in humans. The invention also relates to methods for the preparation of all such compounds and to pharmaceutical compositions comprising them in an effective amount. The present invention also relates to a method of treatment or prevention of dengue viral infections in humans by the administration an effective amount of one or more such compounds, or a pharmaceutically acceptable salt thereof optionally in combination with one or more other medicines, like another antiviral agent, to a patient in need thereof.

One aspect of the invention is the provision of compounds of formula (Ia or Ib)

a stereoisomeric form, a pharmaceutically acceptable salt, solvate or polymorph thereof comprising a mono- or di-substituted indole group; said compound is selected from the group wherein:
$R_1$ is $CF_3$ or $OCF_3$, $R_2$ is H or $OCH_3$ or F, $R_3$ is H; and when $R_2$ is H than $R_3$ can also be $CH_3$.

In particular the compounds of the invention or their stereoisomeric form, a pharmaceutically acceptable salt, solvate or polymorph thereof are selected from the group:

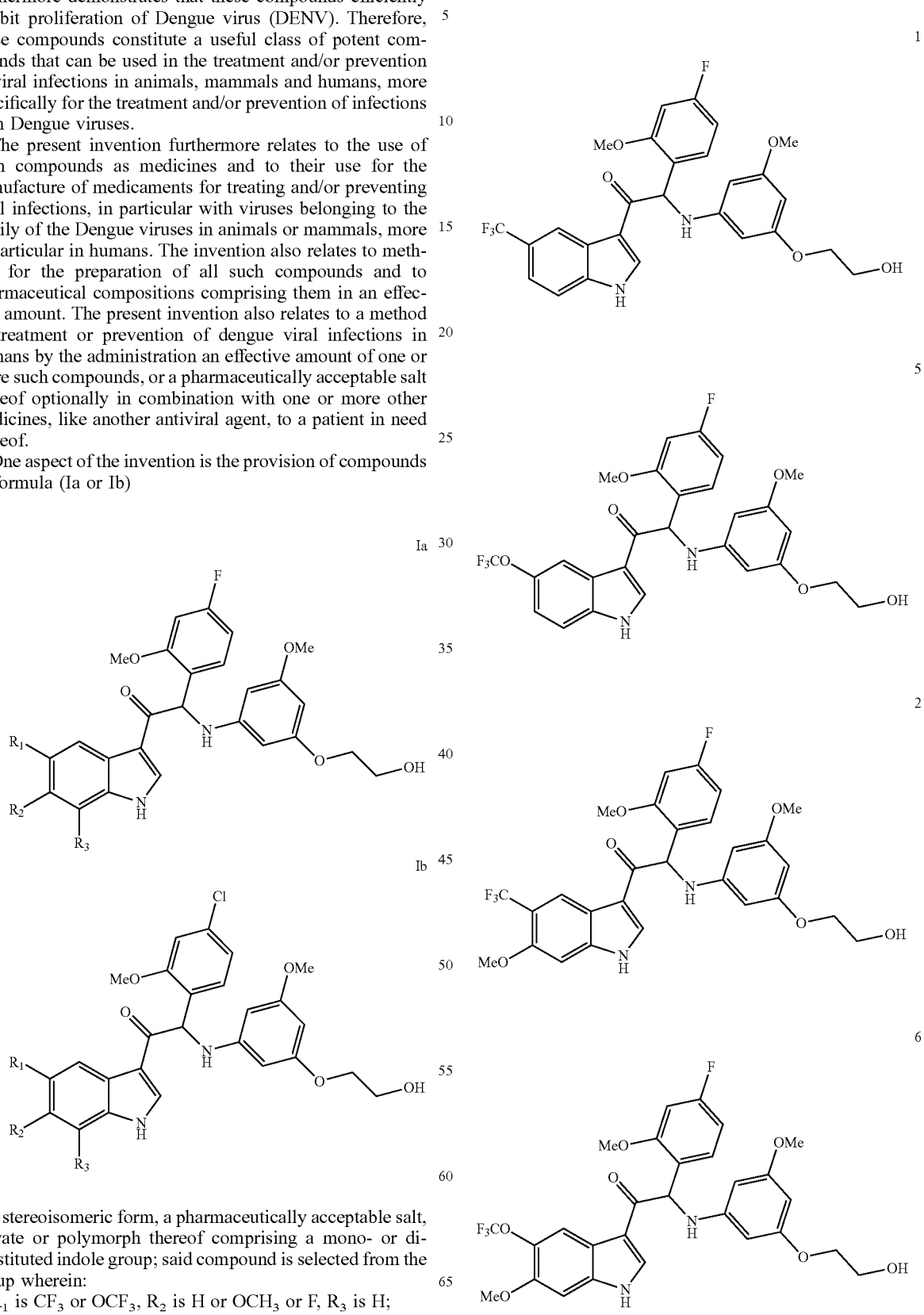

3
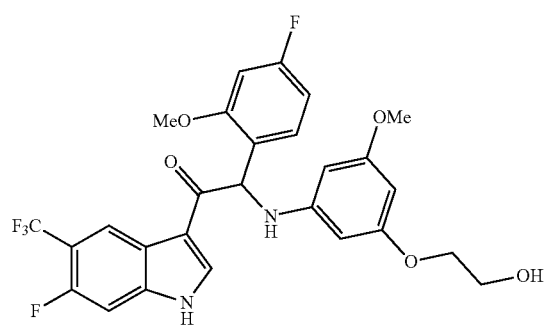
9
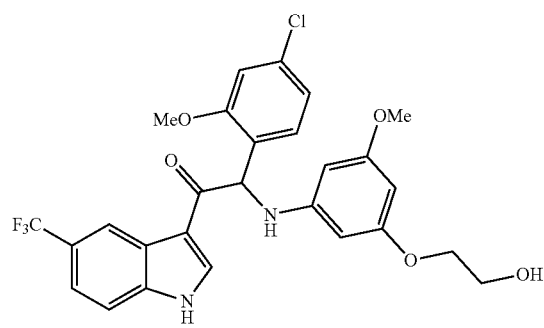
7
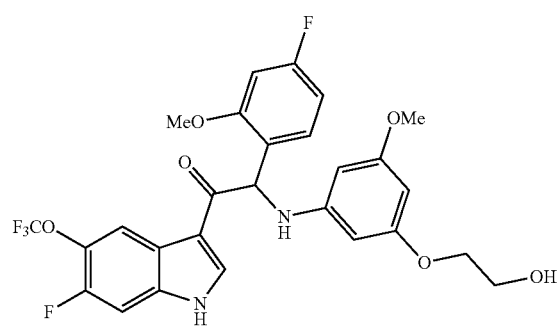
13
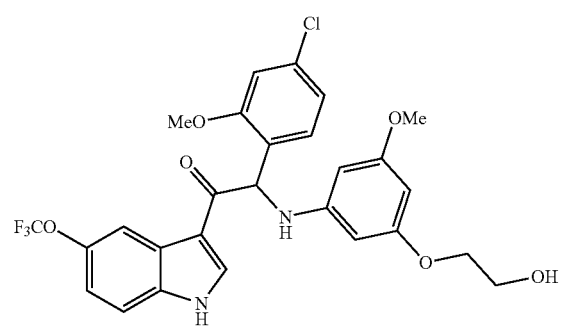
4
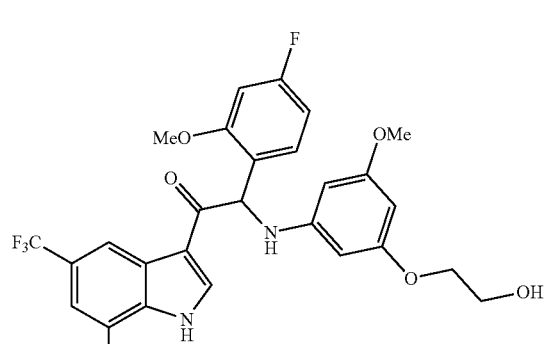
10
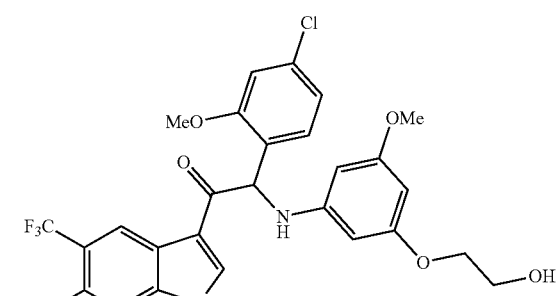
8
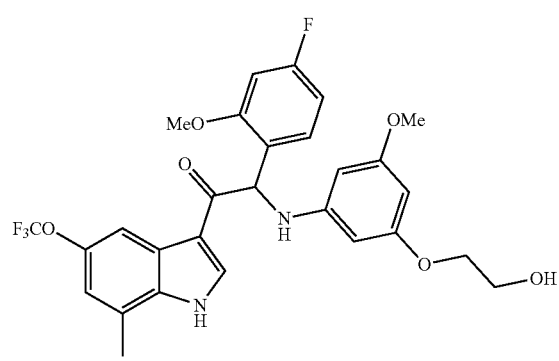
14
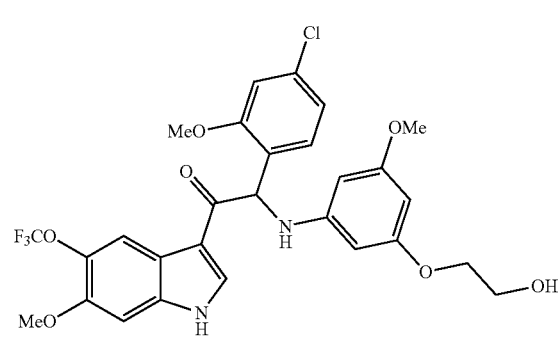

-continued

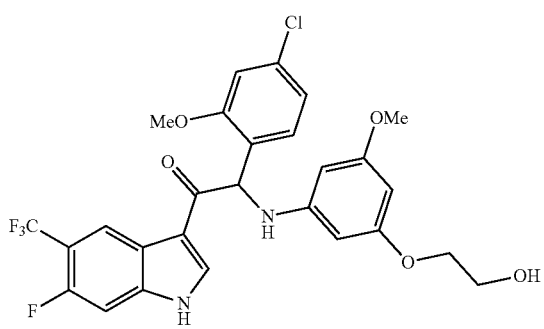

11

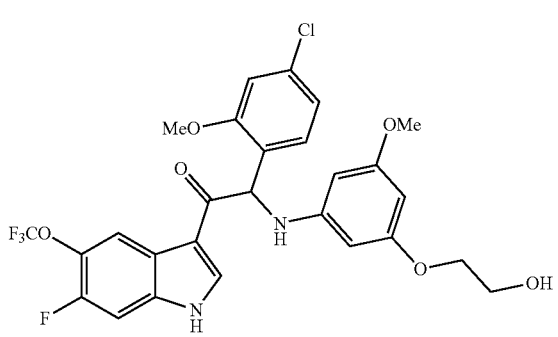

12

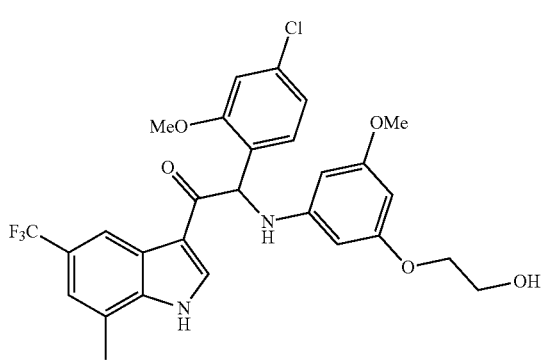

16

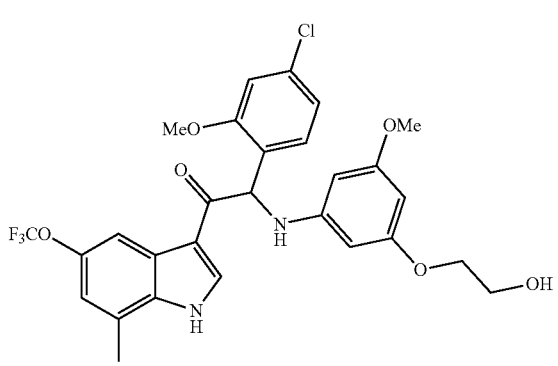

Part of the current invention is also a pharmaceutical composition comprising a compound of formula (Ia or Ib) or a stereoisomeric form, a pharmaceutically acceptable salt, solvate or polymorph thereof together with one or more pharmaceutically acceptable excipients, diluents or carriers.

Pharmaceutically acceptable salts of the compounds of formula (Ia or Ib) include the acid addition and base salts thereof. Suitable acid addition salts are formed from acids which form non-toxic salts. Suitable base salts are formed from bases which form non-toxic salts.

The compounds of the invention may also exist in unsolvated and solvated forms. The term "solvate" is used herein to describe a molecular complex comprising the compound of the invention and one or more pharmaceutically acceptable solvent molecules, for example, ethanol.

The term "polymorph" refers to the ability of the compound of the invention to exist in more than one form or crystal structure.

The compounds of the present invention may be administered as crystalline or amorphous products. They may be obtained for example as solid plugs, powders, or films by methods such as precipitation, crystallization, freeze drying, spray drying, or evaporative drying. They may be administered alone or in combination with one or more other compounds of the invention or in combination with one or more other drugs. Generally, they will be administered as a formulation in association with one or more pharmaceutically acceptable excipients. The term "excipient" is used herein to describe any ingredient other than the compound(s) of the invention. The choice of excipient depends largely on factors such as the particular mode of administration, the effect of the excipient on solubility and stability, and the nature of the dosage form.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, for example, for oral or rectal administration. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions, and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. Also included are solid form preparations that can be converted, shortly before use, to liquid forms.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of infectious diseases will be able to determine the effective amount from the test results presented hereinafter. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (Ia or Ib) used, the particular condition being treated, the severity of the condition being treated, the age, weight and general physical condition of the particular patient as well as other medication the individual may be taking, as is well known to those skilled in the art. Furthermore, it is evident that the effective amount may be lowered or increased depending on the response of the treated subject and/or depending on the evaluation of the physician prescribing the compounds of the instant invention. The effective amount ranges mentioned above are therefore only guidelines and are not intended to limit the scope or use of the invention to any extent.

The present disclosure is also intended to include any isotopes of atoms present in the compounds of the invention. For example, isotopes of hydrogen include tritium and deuterium and isotopes of carbon include C-13 and C-14.

The present compounds used in the current invention may also exist in their stereochemically isomeric form, defining all possible compounds made up of the same atoms bonded by the same sequence of bonds but having different three-dimensional structures, which are not interchangeable. Unless otherwise mentioned or indicated, the chemical designation of compounds encompasses the mixture of all possible stereochemically isomeric forms, which said compounds might possess.

Said mixture may contain all diastereomers and/or enantiomers of the basic molecular structure of said compound. All stereochemically isomeric forms of the compounds used in the present invention either in pure form or in admixture with each other are intended to be embraced within the scope of the present invention including any racemic mixtures or racemates.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i. e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of compounds and intermediates used in this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The compounds of formula (Ia) or (Ib) of the present invention all have at least one chiral carbon atom as indicated in the figure below by the carbon atom labelled with *:

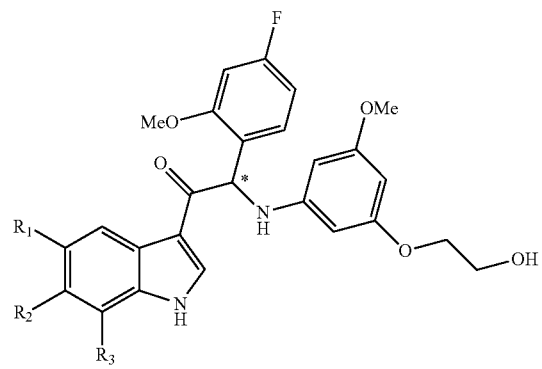

Ia

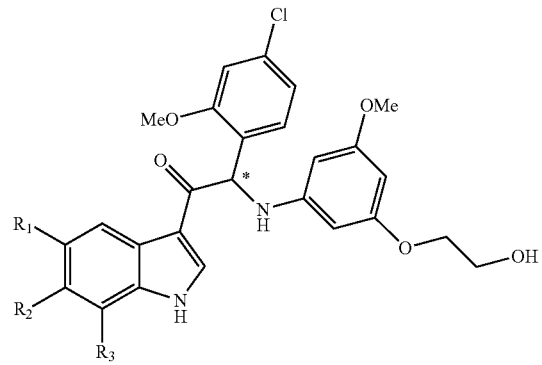

Ib

Due to the presence of said chiral carbon atom, a "compound of formula (Ia) or (Ib)" can be the (R)-enantiomer, the (S)-enantiomer, the racemic form, or any possible combination of the two individual enantiomers in any ratio. When the absolute (R)- or (S)-configuration of an enantiomer is not known, this enantiomer can also be identified by indicating whether the enantiomer is dextrorotatory (+)- or levorotatory (−)- after measuring the specific optical rotation of said particular enantiomer.

In an aspect the present invention relates to a first group of compound of formula (I) wherein the compounds of formula (I) have the (+) specific rotation.

In a further aspect the present invention relates to a second ground of compounds of formula (I) wherein the compounds of formula (I) have the (−) specific rotation.

EXAMPLES

LC/MS Methods

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Compounds are described by their experimental retention times ($R_t$) and ions. If not specified differently in the table of data, the reported molecular ion corresponds to the $[M+H]^+$ (protonated molecule) and/or $[M-H]^-$ (deprotonated molecule). In case the compound was not directly ionizable the type of adduct is specified (i.e. $[M+NH_4]^+$, $[M+HCOO]^-$, etc. . . . ). For molecules with multiple isotopic patterns (Br, Cl), the reported value is the one obtained for the lowest isotope mass. All results were obtained with experimental uncertainties that are commonly associated with the method used.

Hereinafter, "SQD" means Single Quadrupole Detector, "MSD" Mass Selective Detector, "RT" room temperature, "BEH" bridged ethylsiloxane/silica hybrid, "DAD" Diode Array Detector, "HSS" High Strength silica.

LC/MS Method codes (Flow expressed in mL/min; column temperature (T) in ° C.; Run time in minutes)

| Method code | Instrument | Column | Mobile phase | Gradient | Flow Col T | Run time (min) |
|---|---|---|---|---|---|---|
| LC-A | Waters: Acquity ® UPLC ®-DAD-SOD | Waters: BEH C18 (1.7 μm, 2.1 × 50 mm) | A: 10 mM CH$_3$COONH$_4$ in 95% H$_2$O + 5% CH$_3$CN B: CH$_3$CN | from 95% A to 5% A in 1.3 min, held for 0.7 min. | 0.8 mL/min 55° C. | 2 |
| LC-B | Waters: Acquity ® UPLC ®-DAD-SQD | Waters: HSS T3 (1.8 μm, 2.1 × 100 mm) | A: 10 mM CH$_3$COONH$_4$ in 95% H$_2$O + 5% CH$_3$CN B: CH$_3$CN | from 100% A to 5% A in 2.10 min, to 0% A in 0.90 min, to 5% A in 0.5 min | 0.7 mL/min 55° C. | 3.5 |
| LC-C | Waters: Acquity ® UPLC ®-DAD-Quattro Micro ™ | Waters: BEH C18 (1.7 μm, 2.1 × 100 mm) | A: 95% CH$_3$COONH$_4$ 7 mM/5% CH$_3$CN, B: CH$_3$CN | 84.2% A for 0.49 min, to 10.5% A in 2.18 min, held for 1.94 min, back to 84.2% A in 0.73 min, held for 0.73 min. | 0.343 mL/min 40° C. | 6.2 |

SFC/MS Methods

The SFC measurement was performed using an Analytical Supercritical fluid chromatography (SFC) system composed by a binary pump for delivering carbon dioxide (CO2) and modifier, an autosampler, a column oven, a diode array detector equipped with a high-pressure flow cell standing up to 400 bars. If configured with a Mass Spectrometer (MS) the flow from the column was brought to the (MS). It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Analytical SFC/MS Methods (Flow expressed in mL/min; column temperature (T) in ° C.; Run time in minutes, Backpressure (BPR) in bars.

| Method code | column | mobile phase | gradient | Flow Col T | Run time BPR |
|---|---|---|---|---|---|
| SFC-A | Daicel Chiralcel ® OD-H column (5 μm, 150 × 4.6 mm) | A: CO$_2$ B: EtOH (+0.3% iPrNH$_2$) | 30% B hold 7 min, | 3 35 | 7 100 |
| SFC-B | Deicel Chiralpak ® IC column (5 μm, 150 × 4.6 mm) | A: CO$_2$ B: iPrOH (+0.3% iPrNH$_2$) | 30% B hold 7 min, | 3 35 | 7 100 |
| SFC-C | Deicel Chiralpak ® IC column (5 μm, 150 × 4.6 mm) | A: CO$_2$ B: EtOH +0.3% iPrNH$_2$ | 30% B hold 7 min, | 3 35 | 7 100 |
| SFC-D | Deicel Chiralpak ® AS3 column (3.0 μm, 150 × 4.6 mm) | A: CO$_2$ B: EtOH +0.2% iPrNH$_2$ +3% H$_2$O | 10%-50% B in 6 min, hold 3.5 min | 2.5 40 | 9.5 110 |

Melting Points

Values are either peak values or melt ranges, and are obtained with experimental uncertainties that are commonly associated with this analytical method.

DSC823e (Indicated as DSC)

For a number of compounds, melting points were determined with a DSC823e (Mettler-Toledo). Melting points were measured with a temperature gradient of 10° C./minute. Maximum temperature was 300° C.

Optical Rotations

Optical rotations were measured on a Perkin-Elmer 341 polarimeter with a sodium lamp and reported as follows: $[\alpha]°$ ($\lambda$, c g/100 ml, solvent, T° C.). $[\alpha]_\lambda^T = (100\alpha)/(l \times c)$: where l is the path length in dm and c is the concentration in g/100 ml for a sample at a temperature T (° C.) and a wavelength $\lambda$ (in nm). If the wavelength of light used is 589 nm (the sodium D line), then the symbol D might be used instead. The sign of the rotation (+ or −) should always be given. When using this equation the concentration and solvent are always provided in parentheses after the rotation. The rotation is reported using degrees and no units of concentration are given (it is assumed to be g/100 ml).

Example 1: synthesis of 2-(4-fluoro-2-methoxyphenyl)-2-((3-(2-hydroxyethoxy)-5-methoxyphenyl)amino)-1-(5-(trifluoromethyl)-1H-indol-3-yl)ethanone (Compound 1) and Chiral Separation into Enantiomers 1A and 1B

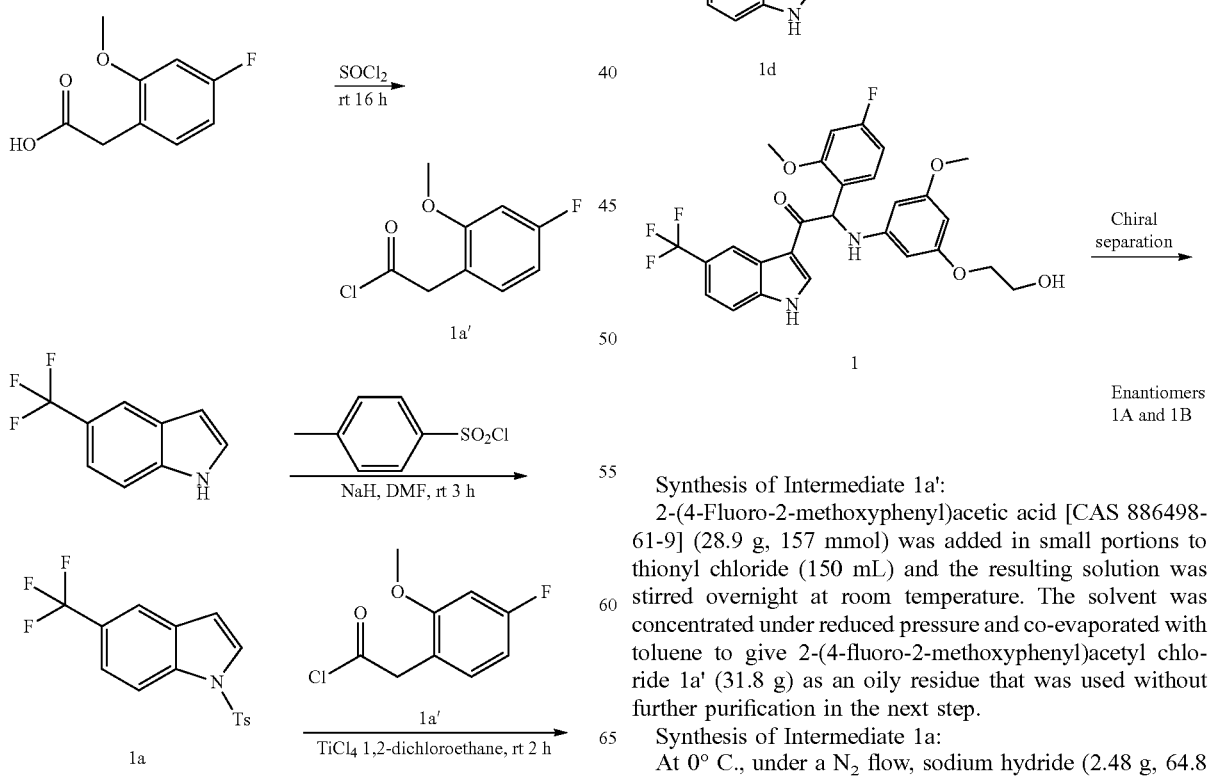

Synthesis of Intermediate 1a':

2-(4-Fluoro-2-methoxyphenyl)acetic acid [CAS 886498-61-9] (28.9 g, 157 mmol) was added in small portions to thionyl chloride (150 mL) and the resulting solution was stirred overnight at room temperature. The solvent was concentrated under reduced pressure and co-evaporated with toluene to give 2-(4-fluoro-2-methoxyphenyl)acetyl chloride 1a' (31.8 g) as an oily residue that was used without further purification in the next step.

Synthesis of Intermediate 1a:

At 0° C., under a $N_2$ flow, sodium hydride (2.48 g, 64.8 mmol) was added portionwise to a mixture of 5-(trifluoromethyl)-1H-indole [CAS 100846-24-0] (10 g, 54.0 mmol) in DMF (150 mL). The mixture was stirred at 0° C. for 30 min. A solution of tosyl chloride (11.3 g, 59.4 mmol) in DMF (50 mL) was added dropwise and the resulting mixture was stirred at room temperature for 3 h. After cooling to 0° C., the mixture was quenched with water and a precipitate was filtered off and dried at 70° C. under reduced pressure overnight to give 1-tosyl-5-(trifluoromethyl)-1H-indole 1a (18.4 g).

Synthesis of Intermediate 1b:

Titanium(IV) chloride (2.32 mL, 21.2 mmol) was added dropwise at room temperature to a stirred solution of 1-tosyl-5-(trifluoromethyl)-1H-indole 1a(3.6 g, 10.6 mmol) and 2-(4-fluoro-2-methoxyphenyl)acetyl chloride 1a' (3.85 g, 19 mmol) in 1,2-dichloroethane (70 mL). The reaction was stirred at room temperature for 2 h. Ice-water was added, and the reaction mixture was extracted with EtOAc. The organic layer was dried over MgSO$_4$, filtered, and the solvent was concentrated under reduced pressure. The residue was purified by column chromatography on silica gel (15-40 µm, 80 g, CH$_2$Cl$_2$/MeOH 99.5/0.5). The fractions containing Compound 1b were combined and the solvent was evaporated under reduced pressure. The compound was taken up with CH$_3$CN/diisopropyl ether. The precipitate was filtered off and dried to give 2-(4-fluoro-2-methoxyphenyl)-1-(1-tosyl-5-(trifluoromethyl)-1H-indol-3-yl)ethanone 1b (3 g).

Synthesis of Intermediate 1c:

Lithium hydroxide (0.66 g, 15.8 mmol) was added to a solution of 2-(4-fluoro-2-methoxyphenyl)-1-(1-tosyl-5-(trifluoromethyl)-1H-indol-3-yl)ethanone 1 b (3.2 g, 6.33 mmol) in THF (18 mL) and water (6 mL). The mixture was stirred at 30° C. for 1 h. Water and EtOAc were added. The organic layer was separated, dried over MgSO$_4$, filtered and the solvent was evaporated under reduced pressure. The solid residue was taken up with diisopropyl ether. The precipitate was filtered off and dried to give 2-(4-fluoro-2-methoxyphenyl)-1-(5-(trifluoromethyl)-1H-indol-3-yl)ethanone 1c (2.1 g).

Synthesis of Intermediate 1d:

At 0° C., a solution of phenyltrimethylammonium tribromide [CAS 4207-56-1] (1.6 g, 4.27 mmol) in THF (50 mL) was added dropwise to a mixture of 2-(4-fluoro-2-methoxyphenyl)-1-(5-(trifluoromethyl)-1H-indol-3-yl)ethanone 1c (1.5 g, 4.27 mmol) in THF (50 mL). The mixture was stirred at 0° C. for 1 h and at room temperature for 4 h. The precipitate was filtered off and washed with EtOAc. The combined filtrates were concentrated under reduced pressure. The residue was dissolved in EtOAc. The organic layer was washed with water, dried over MgSO$_4$, filtered, and the solvent was evaporated under reduced pressure. The residue was taken up with diisopropyl ether. The precipitate was filtered off and dried to give 2-bromo-2-(4-fluoro-2-methoxyphenyl)-1-(5-(trifluoromethyl)-1H-indol-3-yl)ethanone 1d (1.8 g).

Synthesis of Compound 1 and Chiral Separation into Enantiomers 1A and 1B:

A mixture of 2-bromo-2-(4-fluoro-2-methoxyphenyl)-1-(5-(trifluoromethyl)-1H-indol-3-yl)ethanone 1d (1.8 g, 4.18 mmol), 2-(3-amino-5-methoxyphenoxy)ethanol [CAS 725237-16-1] (0.77 g, 4.18 mmol) and diisopropylethylamine (1.08 mL, 6.27 mmol) in CH$_3$CN (100 mL) was stirred at 70° C. for 24 h. The residue was diluted with CH$_2$Cl$_2$ and 1N HCl. The organic layer was separated, dried over MgSO$_4$, filtered, and the solvent was evaporated under reduced pressure. The residue was purified by column chromatography on silica gel (15-40 µm, 80 g, CH$_2$Cl$_2$/MeOH 99/1). The fractions containing Compound 1 were combined and the solvent was evaporated under reduced pressure. The residue (660 mg) was crystallized from diisopropyl ether/CH$_3$CN to give 2-(4-fluoro-2-methoxyphenyl)-2-((3-(2-hydroxyethoxy)-5-methoxyphenyl)amino)-1-(5-(trifluoromethyl)-1H-indol-3-yl)ethanone (Compound 1, 580 mg) as a racemic mixture. The enantiomers were separated via Preparative Chiral SFC (Stationary phase: Chiralcel® OD-H 5 µm 250×20 mm, Mobile phase: 70% CO$_2$, 30% EtOH) to give, after solidification from petroleum ether/diisopropyl ether, 239 mg of the first eluted enantiomer 1A and 248 mg of the second eluted enantiomer 1B.

Compound 1:

$^1$H NMR (500 MHz, DMSO-d$_6$) δ ppm 3.56-3.68 (m, 5H) 3.77-3.89 (m, 2H) 3.95 (s, 3H) 4.79 (t, J=5.4 Hz, 1H) 5.72 (t, J=2.0 Hz, 1H) 5.94 (d, J=1.9 Hz, 2H) 6.18 (d, J=7.9 Hz, 1H) 6.39 (d, J=8.2 Hz, 1H) 6.74 (td, J=8.5, 2.5 Hz, 1H) 6.93 (dd, J=11.3, 2.5 Hz, 1H) 7.38 (dd, J=8.5, 6.9 Hz, 1H) 7.53 (dd, J=8.5, 1.6 Hz, 1H) 7.68 (d, J=8.5 Hz, 1H) 8.49 (br s, 1H) 8.60 (s, 1H) 12.41 (br s, 1H)

LC/MS (method LC-C): R$_t$ 3.03 min, MH$^+$ 533

Melting point: 132° C.

Enantiomer 1A:

$^1$H NMR (400 MHz, DMSO-d$_6$) δ ppm 3.58-3.68 (m, 5H) 3.77-3.89 (m, 2H) 3.94 (s, 3H) 4.77 (t, J=5.6 Hz, 1H) 5.72 (t, J=1.8 Hz, 1H) 5.94 (d, J=1.5 Hz, 2H) 6.18 (d, J=8.1 Hz, 1H) 6.37 (d, J=8.1 Hz, 1H) 6.73 (td, J=8.3, 2.5 Hz, 1H) 6.93 (dd, J=11.4, 2.3 Hz, 1H) 7.38 (dd, J=8.1, 7.1 Hz, 1H) 7.53 (dd, J=8.6, 1.5 Hz, 1H) 7.68 (d, J=8.6 Hz, 1H) 8.49 (s, 1H) 8.59 (s, 1H) 12.34 (br s, 1H)

LC/MS (method LC-C): R$_t$ 3.02 min, MH$^+$ 533

[α]$_D^{20}$: −93.7° (c 0.2455, DMF)

Chiral SFC (method SFC-A): R$_t$ 2.03 min, MH$^+$ 533, chiral purity 100%.

Enantiomer 1B:

$^1$H NMR (400 MHz, DMSO-d$_6$) δ ppm 3.56-3.70 (m, 5H) 3.76-3.89 (m, 2H) 3.94 (s, 3H) 4.77 (t, J=5.6 Hz, 1H) 5.72 (s, 1H) 5.94 (d, J=1.5 Hz, 2H) 6.18 (d, J=8.1 Hz, 1H) 6.37 (d, J=8.1 Hz, 1H) 6.73 (td, J=8.5, 2.3 Hz, 1H) 6.93 (dd, J=11.4, 2.3 Hz, 1H) 7.38 (t, J=7.6 Hz, 1H) 7.53 (d, J=8.6 Hz, 1H) 7.68 (d, J=8.6 Hz, 1H) 8.48 (s, 1H) 8.59 (s, 1H) 12.35 (br s, 1H)

LC/MS (method LC-C): R$_t$ 3.02 min, MH$^+$ 533

[α]$_D^{20}$: +89.5° (c 0.2636, DMF)

Chiral SFC (method SFC-A): R$_t$ 3.28 min, MH$^+$ 533, chiral purity 100%.

Example 2: 2-(4-fluoro-2-methoxyphenyl)-2-((3-(2-hydroxyethoxy)-5-methoxyphenyl)amino)-1-(6-methoxy-5-(trifluoromethyl)-1H-indol-3-yl)ethanone (Compound 2) and Chiral Separation into Enantiomers 2A and 2B

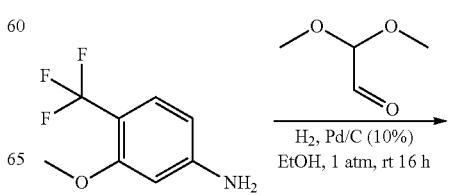

-continued

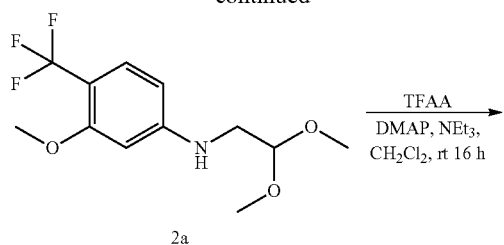

2a

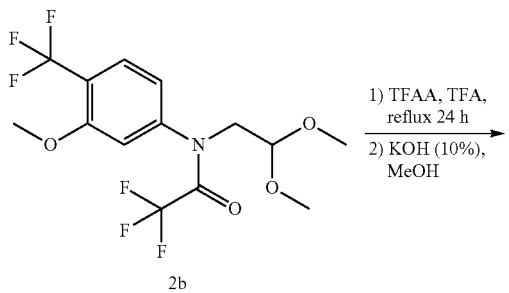

2b

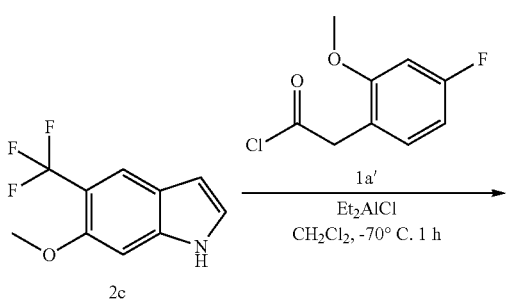

2c

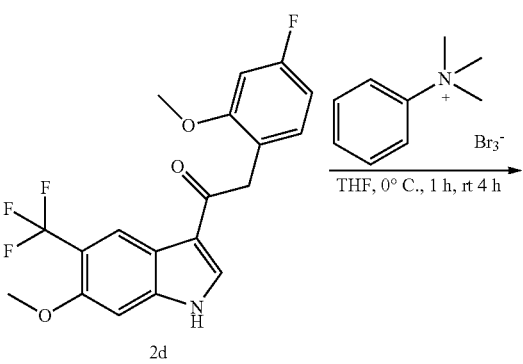

2d

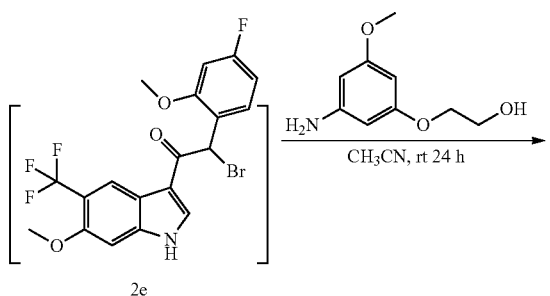

2e

-continued

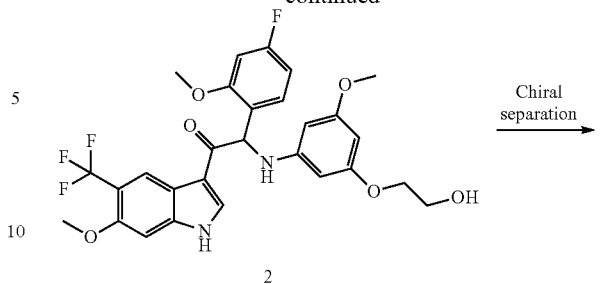

2

Enantiomers 2A and 2B

Synthesis of Intermediate 2a:

A mixture of 3-methoxy-4-(trifluoromethyl)aniline [CAS 106877-20-7] (25 g, 130.7 mmol), glyoxal-dimethylacetal [CAS 51673-84-8] (39.3 mL, 261.571 mmol) and Pd/C (10%) (2.8 g, 2.62 mmol) in EtOH (250 mL) was hydrogenated under atmospheric pressure of $H_2$ at room temperature for 16 h. The mixture was filtered through a pad of Celite®. The filter cake was washed with EtOH and the combined filtrates were concentrated under reduced pressure. The residue was taken up with EtOAc. The organic layer was washed with water, dried over $MgSO_4$, filtered and the solvent was evaporated to give N-(2,2-dimethoxyethyl)-3-methoxy-4-(trifluoromethyl)aniline 2a (39.9 g).

Synthesis of Intermediate 2b:

At 0° C., trifluoroacetic anhydride (TFAA) (18.2 mL, 130.7 mmol) was added dropwise to a solution of N-(2,2-dimethoxyethyl)-3-methoxy-4-(trifluoro-methyl)aniline 2a (36.5 g, 130.7 mmol), triethylamine (21.8 mL, 156.8 mmol) and 4-dimethylaminopyridine (DMAP) (800 mg, 6.54 mmol) in $CH_2Cl_2$ (400 mL). The mixture was stirred at room temperature for 16 h. The reaction was quenched with a solution of $K_2CO_3$ 10% in water and extracted with $CH_2Cl_2$. The organic layer was dried over $MgSO_4$, filtered and the solvent was evaporated under reduced pressure. The residue was purified by flash chromatography on silica gel (15-40 μm, 330 g, heptane/EtOAc 85/15). The pure fractions were combined and evaporated to dryness under reduced pressure to give N-(2,2-dimethoxyethyl)-2,2,2-trifluoro-N-(3-methoxy-4-(trifluoromethyl)phenyl)acetamide 2b (33.5 g).

Synthesis of Intermediate 2c:

A mixture of N-(2,2-dimethoxyethyl)-2,2,2-trifluoro-N-(3-methoxy-4-(trifluoro-methyl)phenyl)acetamide 2b (15.8 g, 42.1 mmol) in trifluoroacetic anhydride (TFAA) (58 mL) and trifluoroacetic acid (TFA) (100 mL) was heated under reflux for 24 h. The mixture was cooled to room temperature and quenched with ice/water. The precipitate was filtered off and washed with water. The precipitate was taken up with KOH 10% in water (200 mL) and $CH_3OH$ (200 mL) and the resulting mixture was stirred at room temperature for 2 h. $CH_3OH$ was evaporated under reduced pressure. The resulting aqueous mixture was further diluted with water and extracted with EtOAc. The organic layer was washed with water, dried over $MgSO_4$, filtered and the solvent was evaporated under reduced pressure. Purification was done by flash chromatography on silica gel (15-40 μm, 220 g, heptane/EtOAc 85/15). The pure fractions were combined and evaporated to dryness under reduced pressure to give 6-methoxy-5-(trifluoromethyl)-1H-indole 2c (5.4 g).

Synthesis of Intermediate 2d:

The reaction was performed in two separate batches, on 6.51 mmol and 12.8 mmol scale of 6-methoxy-5-(trifluoromethyl)-1H-indole 2c, respectively. Under a N₂ flow, diethylaluminum chloride 1M in hexane (19.17 mL, 19.17 mmol) was added dropwise at −70° C. to a solution of 6-methoxy-5-(trifluoromethyl)-1H-indole 2c (1.40 g, 6.51 mmol) in CH₂Cl₂ (15 mL). After 5 min of stirring at −70° C., 2-(4-fluoro-2-methoxyphenyl)acetyl chloride 1a' (3.88 g, 19.17 mmol) in CH₂Cl₂ (15 mL) was added dropwise and the reaction mixture was kept at −70° C. for 1 h. Ice-water was added. The mixture was extracted with EtOAc. The organic layer was dried over MgSO₄, filtered and the solvent was evaporated under reduced pressure. The residue was crystallized from CH₂Cl₂. The precipitate was filtered off and dried to give a first batch of 2-(4-fluoro-2-methoxyphenyl)-1-(6-methoxy-5-(trifluoromethyl)-1H-indol-3-yl)ethanone 2d (1.0 g). The filtrate was concentrated under reduced pressure (fraction 1).

Using the same procedure, starting from 12.8 mmol of 6-methoxy-5-(trifluoromethyl)-1H-indole 2c, a second batch of intermediate 2d (840 mg) was obtained after crystallization from CH₂Cl₂. The filtrate was concentrated under reduced pressure (fraction 2).

The combined filtrates of fractions 1 and 2 were evaporated and the residue was purified by flash chromatography on silica gel (15-40 μm, 120 g, heptane/EtOAc 80/20). The pure fractions were combined and evaporated to dryness to give a third batch of intermediate 2d (730 mg).

Synthesis of Compound 2 and Chiral Separation into Enantiomers 2A and 2B:

At 0° C., a solution of phenyltrimethylammonium tribromide [CAS 4207-56-1] (3 g, 7.97 mmol) in THF (30 mL) was added dropwise to a mixture of 2-(4-fluoro-2-methoxyphenyl)-1-(6-methoxy-5-(trifluoromethyl)-1H-indol-3-yl)ethanone 2d (3.04 g, 7.97 mmol) in THF (30 mL). The mixture was stirred at 0° C. for 1 h and at room temperature for 4 h. A solution of 2-(3-amino-5-methoxyphenoxy)ethanol [CAS 725237-16-1] (4.38 g, 23.9 mmol) in CH₃CN (30 mL) was added dropwise and stirring was continued at room temperature for 24 h. The mixture was concentrated under reduced pressure. The residue was dissolved in EtOAc and washed with 1 N HCl and water. The organic layer was dried over MgSO₄, filtered, and the solvent was evaporated under reduced pressure. The residue (5.1 g) was purified by flash chromatography on silica gel (15-40 μm, 120 g, CH₂Cl₂/CH₃OH 99.5/0.5). The pure fractions were combined and evaporated to dryness under reduced pressure to give a first fraction of 2-(4-fluoro-2-methoxyphenyl)-2-((3-(2-hydroxyethoxy)-5-methoxyphenyl)amino)-1-(6-methoxy-5-(trifluoromethyl)-1H-indol-3-yl)ethanone (Compound 2, 2.1 g) as a racemate. The impure fractions were combined, concentrated under reduced pressure, and crystallized from Et₂O to give 520 mg of second fraction of racemic Compound 2.

The enantiomers of Compound 2 (2.62 g) were separated via chiral SFC (Stationary phase: Chiralpak® IC 5 μm 250×30 mm, Mobile phase: 65% CO₂, 35% iPrOH+0.3% iPrNH₂) to give 1.0 g of the first eluted enantiomer and 1.1 g of the second eluted enantiomer. The first eluted enantiomer was purified by flash chromatography on silica gel (15-40 μm, 24 g, CH₂Cl₂/CH₃OH/NH₄OH 99/1/0.1). The pure fractions were combined and evaporated to dryness to give, after solidification in Et₂O/heptane, 750 mg of Enantiomer 2A. The second eluted enantiomer was purified by flash chromatography on silica gel (15-40 μm, 24 g, CH₂Cl₂/CH₃OH/NH₄OH 99/1/0.1). The pure fractions were combined and evaporated to dryness to give, after solidification in Et₂O/heptane, 755 mg of Enantiomer 2B.

Compound 2:
$^1$H NMR (500 MHz, DMSO-$d_6$) δ ppm 3.61 (s, 3H) 3.64 (q, J=4.9 Hz, 2H) 3.77-3.87 (m, 2H) 3.89 (s, 3H) 3.95 (s, 3H) 4.79 (br t, J=5.4 Hz, 1H) 5.72 (s, 1H) 5.93 (d, J=1.6 Hz, 2H) 6.14 (d, J=8.2 Hz, 1H) 6.37 (d, J=8.2 Hz, 1H) 6.73 (td, J=8.5, 2.5 Hz, 1H) 6.93 (dd, J=11.3, 2.2 Hz, 1H) 7.20 (s, 1H) 7.37 (dd, J=8.5, 7.3 Hz, 1H) 8.37 (s, 1H) 8.43 (s, 1H) 12.14 (br s, 1H)

LC/MS (method LC-C): $R_t$ 2.99 min, MH⁺ 563

Melting point: 174° C.

Enantiomer 2A:
$^1$H NMR (500 MHz, DMSO-$d_6$) δ ppm 3.61 (s, 3H) 3.64 (q, J=5.4 Hz, 2H) 3.77-3.87 (m, 2H) 3.89 (s, 3H) 3.95 (s, 3H) 4.79 (t, J=5.5 Hz, 1H) 5.72 (t, J=2.2 Hz, 1H) 5.93 (d, J=1.9 Hz, 2H) 6.14 (d, J=7.9 Hz, 1H) 6.37 (d, J=8.2 Hz, 1H) 6.73 (td, J=8.5, 2.5 Hz, 1H) 6.94 (dd, J=11.3, 2.5 Hz, 1H) 7.21 (s, 1H) 7.37 (dd, J=8.5, 6.9 Hz, 1H) 8.37 (s, 1H) 8.43 (s, 1H) 12.14 (br s, 1H)

LC/MS (method LC-C): $R_t$ 2.97 min, MH⁺ 563

$[α]_D^{20}$: +92.3° (c 0.26, DMF)

Chiral SFC (method SFC-B): $R_t$ 2.34 min, MH⁺ 563, chiral purity 100%.

Enantiomer 2B:
$^1$H NMR (500 MHz, DMSO-$d_6$) δ ppm 3.61 (s, 3H) 3.64 (q, J=5.4 Hz, 2H) 3.77-3.87 (m, 2H) 3.89 (s, 3H) 3.95 (s, 3H) 4.79 (t, J=5.5 Hz, 1H) 5.72 (t, J=2.0 Hz, 1H) 5.93 (d, J=2.2 Hz, 2H) 6.14 (d, J=8.2 Hz, 1H) 6.37 (d, J=7.9 Hz, 1H) 6.73 (td, J=8.5, 2.5 Hz, 1H) 6.93 (dd, J=11.3, 2.5 Hz, 1H) 7.21 (s, 1H) 7.37 (dd, J=8.5, 6.9 Hz, 1H) 8.37 (s, 1H) 8.43 (s, 1H) 12.14 (br s, 1H)

LC/MS (method LC-C): $R_t$ 2.97 min, MH⁺ 563

$[α]_D^{20}$: −88.4° (c 0.25, DMF)

Chiral SFC (method SFC-B): $R_t$ 3.25 min, MH⁺ 563, chiral purity 99.6%.

Example 3: synthesis of 2-(4-fluoro-2-methoxyphenyl)-1-(6-fluoro-5-(trifluoromethyl)-1H-indol-3-yl)-2-((3-(2-hydroxyethoxy)-5-methoxyphenyl)amino) ethanone (Compound 3) and Chiral Separation into Enantiomers 3A and 3B

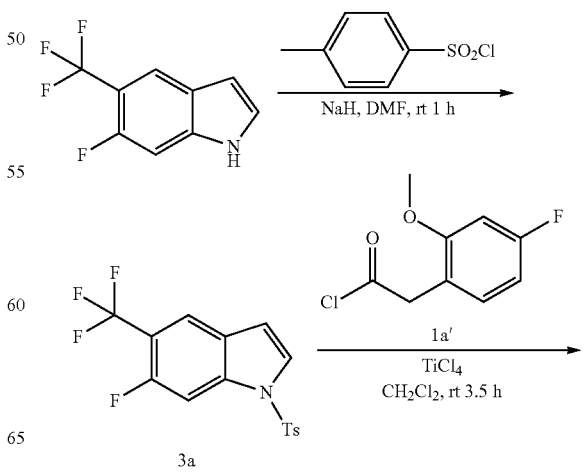

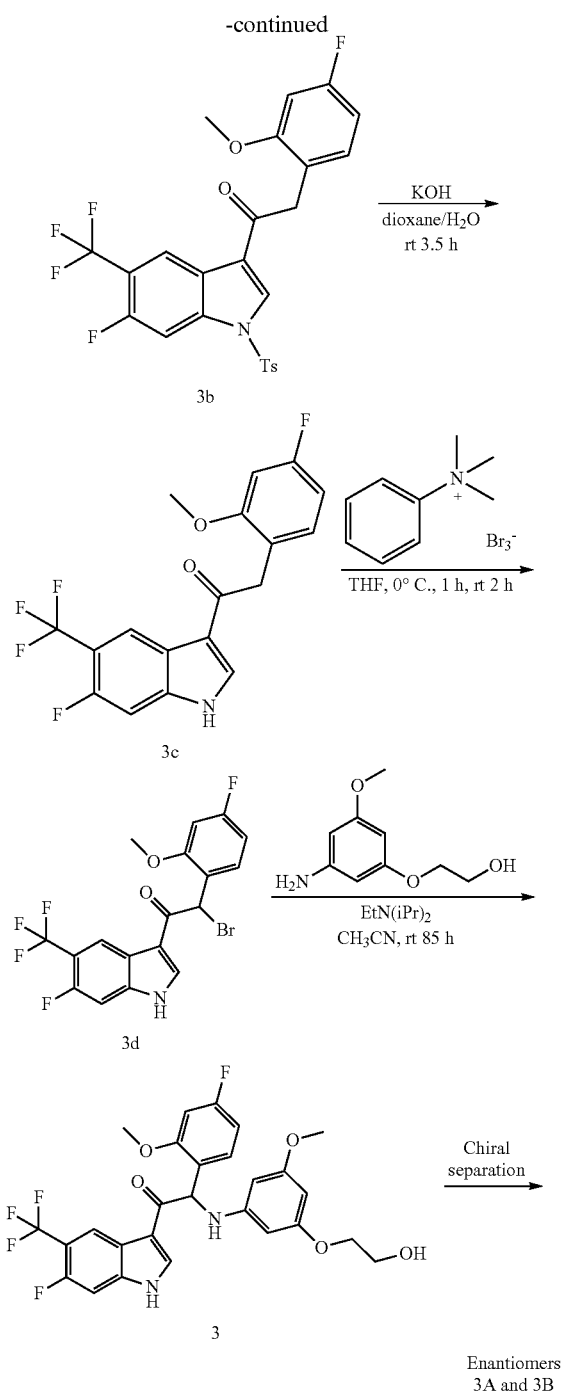

Synthesis of Intermediate 3b:

Titanium(IV) chloride (1.23 mL, 11.2 mmol) was added dropwise at room temperature to a stirred solution of 6-fluoro-1-tosyl-5-(trifluoromethyl)-1H-indole 3a (2 g, 5.6 mmol) and 2-(4-fluoro-2-methoxyphenyl)acetyl chloride 1a' (2.27 g, 11.2 mmol) in dichloromethane (50 mL). The reaction was stirred at room temperature for 3.5 h. The reaction was quenched by the addition of crushed ice (40 g). After stirring for 1 h, the layers were separated. The organic layer was dried over $MgSO_4$, filtered, and the solvent was concentrated under reduced pressure. The residue was stirred up in boiling $CH_2Cl_2$ (15 mL). The solids were filtered off, washed with $CH_2Cl_2$ (3×) and dried under vacuum at 50° C. to provide 1-(6-fluoro-1-tosyl-5-(trifluoromethyl)-1H-indol-3-yl)-2-(4-fluoro-2-methoxyphenyl)ethanone 3b (315 mg). The filtrate was left standing overnight, allowing for a second crop to precipitate from the solution. The product was filtered off, washed with $CH_2Cl_2$ (3×), and dried under vacuum at 50° C. to provide a second crop of intermediate 3b (505 mg). The filtrate was evaporated. The residue was purified by flash chromatography (stationary phase: Biotage® Snap Ultra silica 50 g, Mobile phase: heptane/$CH_2Cl_2$ gradient 100/0 to 0/100). The desired fractions were combined and concentrated under reduced pressure to a residual volume of 25 mL. A precipitate was formed, filtered off, washed with heptane (3×), and dried under vacuum at 50° C. to provide a third crop of intermediate 3b (922 mg).

Synthesis of Intermediate 3c:

Potassium hydroxide (0.65 g, 11.6 mmol) was added to a solution of 1-(6-fluoro-1-tosyl-5-(trifluoromethyl)-1H-indol-3-yl)-2-(4-fluoro-2-methoxyphenyl)ethanone 3b (1.74 g, 3.33 mmol) in dioxane (30 mL) and water (10 mL). The mixture was stirred at room temperature for 3.5 h. The reaction mixture was poured out slowly into a stirring mixture of cold water (100 mL) and 1N HCl (15 mL). After stirring for 30 minutes, the product was extracted with 2-MeTHF (2×). The combined organic layers were washed with brine, dried over $MgSO_4$, filtered off, and evaporated under reduced pressure. The residue was stirred up in $CH_2Cl_2$ (15 mL), filtered off, washed with $CH_2Cl_2$ (3×), and dried under vacuum at 50° C. to provide 2-(4-fluoro-2-methoxyphenyl)-1-(6-fluoro-5-(trifluoromethyl)-1H-indol-3-yl)ethanone 3c (1.13 g).

Synthesis of Intermediate 3d:

A solution of 2-(4-fluoro-2-methoxyphenyl)-1-(6-fluoro-5-(trifluoromethyl)-1H-indol-3-yl)ethanone 3c (1.13 g, 3.06 mmol) in THF (40 mL) was cooled to 0° C., under $N_2$ atmosphere. Phenyltrimethylammonium tribromide [CAS 4207-56-1] (1.21 g, 3.22 mmol) was added. The mixture was stirred at 0° C. for 1 h and at room temperature for 2 h. The precipitate was filtered off and washed with THF (2×). The combined filtrates were concentrated under reduced pressure to give 2-bromo-2-(4-fluoro-2-methoxyphenyl)-1-(6-fluoro-5-(trifluoromethyl)-1H-indol-3-yl)ethanone 3d (1.37 g), which was used as such in the next step without further purification.

Synthesis of Compound 3 and Chiral Separation into Enantiomers 3A and 3B:

A mixture of 2-bromo-2-(4-fluoro-2-methoxyphenyl)-1-(6-fluoro-5-(trifluoromethyl)-1H-indol-3-yl)ethanone 3d (1.37 g, 3.06 mmol), 2-(3-amino-5-methoxyphenoxy)ethanol [CAS 725237-16-1] (1.22 g, 6.13 mmol) and diisopropylethylamine (1.06 mL, 6.13 mmol) in $CH_3CN$ (60 mL) was stirred at room temperature for 85 h. The reaction mixture was poured out into water (250 mL) and the product was extracted with $Et_2O$ (2×). The combined organic layers Synthesis of Intermediate 3a:

A solution of 6-fluoro-5-(trifluoromethyl)-1H-indole [CAS 875306-79-9] (4.8 g, 24.6 mmol) in DMF (100 mL) was cooled to 0° C. Under a $N_2$ flow, sodium hydride (1.09 g, 28.4 mmol) was added portionwise. The mixture was stirred at 0° C. for 20 min. A solution of tosyl chloride (4.96 g, 26 mmol) in DMF (20 mL) was added dropwise and the resulting mixture was stirred at 0° C. for 30 min and at room temperature for 1 h. The mixture was poured out into ice-water (600 mL) and vigorously stirred for 40 min. The precipitate was filtered off, washed with water (6×) and dried at 50° C. under reduced pressure to give 6-fluoro-1-tosyl-5-(trifluoromethyl)-1H-indole 3a (7.2 g).

were dried over MgSO₄, filtered, and the solvent was evaporated under reduced pressure. The residue was purified by flash chromatography (Stationary phase: Grace Reveleris® silica 40 g, Mobile phase: heptane/EtOAc/EtOH gradient 100/0/0 to 40/45/15). The fractions containing Compound 3 were combined and the solvent was evaporated under reduced pressure. The residue was further purified via preparative HPLC (Stationary phase: RP XBridge C18 OBD—10 μm, 50×150 mm, Mobile phase: 0.25% NH₄HCO₃ solution in water, MeOH). The desired fractions were combined and concentrated very slowly under reduced pressure using a rotary evaporator with a bath temperature of 45° C., to a residual volume of 10 mL. The resulting solution was kept standing for 18 h to allow precipitation of the product. The product was filtered off, washed with H₂O (5×), and dried under vacuum at 45° C. to provide 2-(4-fluoro-2-methoxyphenyl)-1-(6-fluoro-5-(trifluoromethyl)-1H-indol-3-yl)-2-((3-(2-hydroxyethoxy)-5-methoxyphenyl) amino)ethanone (Compound 3, 501 mg) as a racemic mixture.

The enantiomers of Compound 3 (473 mg) were separated via Normal Phase Chiral separation (Stationary phase: AS 20 μm, Mobile phase: 50% ethanol, 50% heptane) to give enantiomer 3A as the first eluted product and enantiomer 3B as the second eluted enantiomer. Both enantiomers were stirred up in a mixture of MeOH/water 4/1 (5 mL). The resulting solids were filtered off, washed with water and dried under vacuum at 45° C. to provide 152 mg of Enantiomer 3A and 163 mg of Enantiomer 3B.

Compound 3:

¹H NMR (400 MHz, DMSO-d₆) δ ppm 3.61 (s, 3H) 3.64 (q, J=5.2 Hz, 2H) 3.77-3.90 (m, 2H) 3.94 (s, 3H) 4.76 (t, J=5.5 Hz, 1H) 5.73 (t, J=2.1 Hz, 1H) 5.94 (d, J=2.2 Hz, 2H) 6.17 (d, J=8.1 Hz, 1H) 6.37 (d, J=8.1 Hz, 1H) 6.74 (td, J=8.5, 2.4 Hz, 1H) 6.93 (dd, J=11.3, 2.5 Hz, 1H) 7.38 (dd, J=8.6, 6.8 Hz, 1H) 7.58 (d, J=11.4 Hz, 1H) 8.47 (d, J=7.0 Hz, 1H) 8.57 (s, 1H) 12.42 (br s, 1H)

LC/MS (method LC-A): R$_t$ 1.11 min, MH⁺ 551

Enantiomer 3A:

¹H NMR (400 MHz, DMSO-d₆) δ ppm 3.61 (s, 3H) 3.64 (q, J=5.3 Hz, 2H) 3.77-3.89 (m, 2H) 3.94 (s, 3H) 4.77 (t, J=5.5 Hz, 1H) 5.73 (t, J=2.1 Hz, 1H) 5.94 (d, J=2.2 Hz, 2H) 6.17 (d, J=8.1 Hz, 1H) 6.38 (d, J=8.1 Hz, 1H) 6.74 (td, J=8.5, 2.5 Hz, 1H) 6.93 (dd, J=11.2, 2.4 Hz, 1H) 7.37 (dd, J=8.6, 6.8 Hz, 1H) 7.58 (d, J=11.3 Hz, 1H) 8.46 (d, J=6.9 Hz, 1H) 8.57 (s, 1H) 12.42 (br s, 1H)

LC/MS (method LC-A): R$_t$ 1.10 min, MH⁺ 551

$[\alpha]_D^{20}$: +91.0° (c 0.435, DMF)

Chiral SFC (method SFC-D): R$_t$ 2.93 min, MH⁺ 551, chiral purity 100%.

Enantiomer 3B:

¹H NMR (400 MHz, DMSO-d₆) δ ppm 3.61 (s, 3H) 3.62-3.67 (m, 2H) 3.76-3.89 (m, 2H) 3.94 (s, 3H) 4.76 (br t, J=5.3 Hz, 1H) 5.73 (t, J=2.1 Hz, 1H) 5.94 (d, J=2.0 Hz, 2H) 6.17 (d, J=8.1 Hz, 1H) 6.37 (d, J=8.1 Hz, 1H) 6.74 (td, J=8.5, 2.4 Hz, 1H) 6.93 (dd, J=11.4, 2.4 Hz, 1H) 7.38 (dd, J=8.6, 7.0 Hz, 1H) 7.58 (d, J=11.4 Hz, 1H) 8.47 (d, J=7.3 Hz, 1H) 8.57 (s, 1H) 12.43 (br s, 1H)

LC/MS (method LC-A): R$_t$ 1.10 min, MH⁺ 551

$[\alpha]_D^{20}$: −82.7° (c 0.475, DMF)

Chiral SFC (method SFC-D): R$_t$ 3.15 min, MH⁺ 551, chiral purity 99.4%.

Example 4: synthesis of 2-(4-fluoro-2-methoxyphenyl)-2-((3-(2-hydroxyethoxy)-5-methoxyphenyl) amino)-1-(7-methyl-5-(trifluoromethyl)-1H-indol-3-yl)ethanone (Compound 4) and Chiral Separation into Enantiomers 4A and 4B

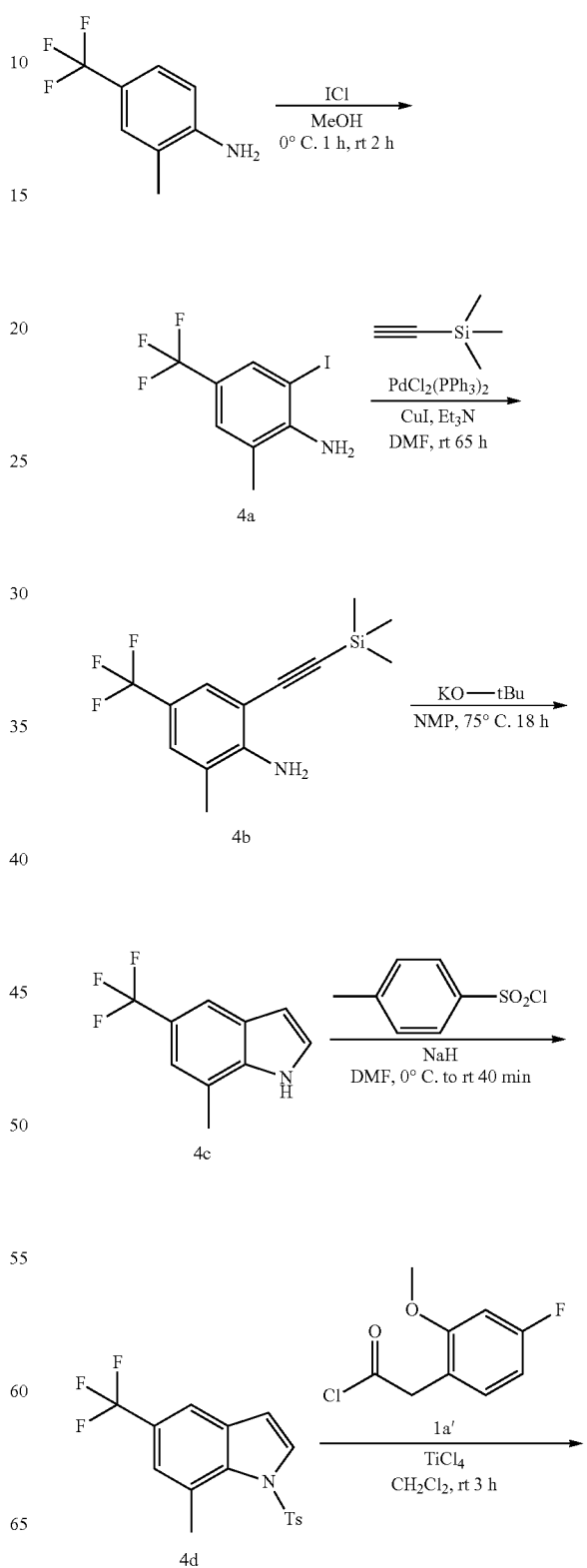

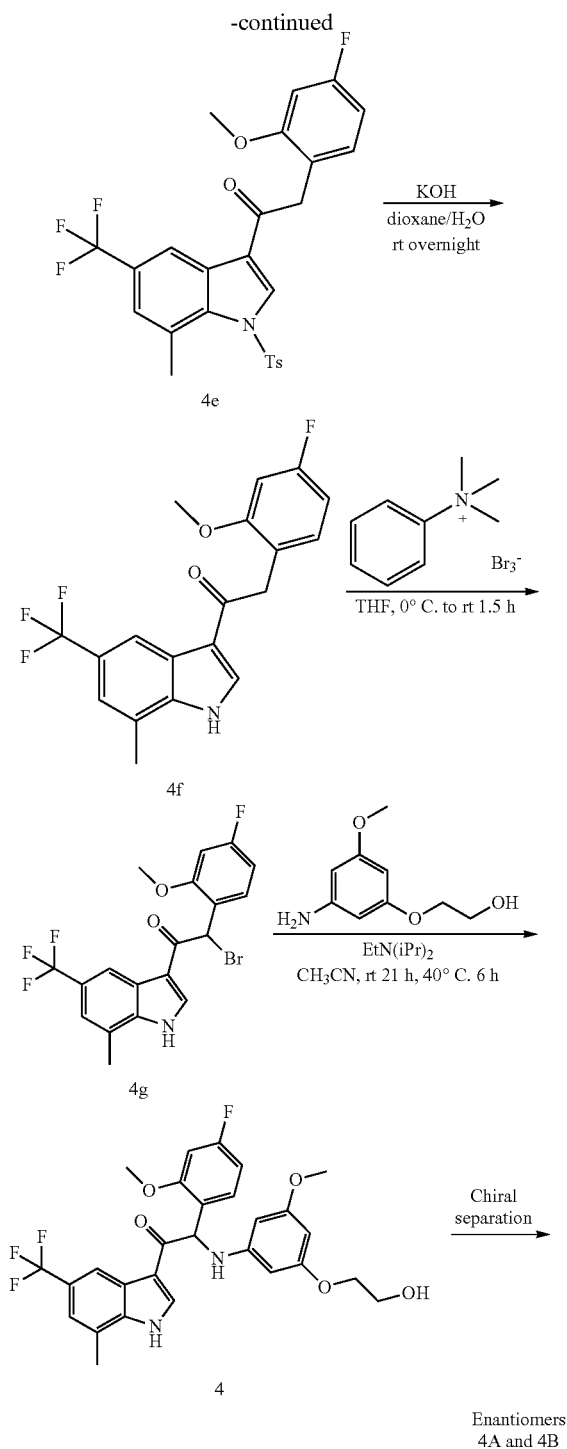

Synthesis of Intermediate 4a:

A solution of 2-methyl-4-(trifluoromethyl)aniline [CAS 67169-22-6] (9.85 g, 56.2 mmol) in MeOH (60 mL) was stirred on an ice-bath. A solution of iodine chloride [CAS 7790-99-0] 1M in CH$_2$Cl$_2$ (61.9 mL, 61.9 mmol) was added dropwise. The reaction mixture was stirred at 0° C. for 1 h and at room temperature for 2 h. The solvents were evaporated under reduced pressure. The residue was stirred up in DIPE (10 mL), the precipitate was filtered off, washed with DIPE (5×), and dried under vacuum at 45° C. to give 2-iodo-6-methyl-4-(trifluoromethyl)aniline 4a (2.47 g). The filtrate was evaporated under reduced pressure. The residue was purified by flash chromatography (Stationary phase: Biotage® Snap Ultra silica 100 g, Mobile phase: heptane/EtOAc gradient 100/0 to 20/80). The desired fractions were combined, evaporated under reduced pressure, and co-evaporated with toluene (3×) to provide a second batch of 4a (6.8 g).

Synthesis of Intermediate 4b:

A stirred solution of 2-iodo-6-methyl-4-(trifluoromethyl)aniline 4a (6.7 g, 22.3 mmol) in DMF (75 mL) was degassed using a N$_2$-flow bubbling through the solution for 15 min. Copper(I) iodide (848 mg, 4.45 mmol), triethylamine (9.28 mL, 66.8 mmol), dichlorobis(triphenylphosphine)palladium(II) (1.56 g, 2.23 mmol) and trimethylsilylacetylene (9.24 mL, 66.8 mmol) were added, and the reaction mixture was stirred at room temperature under N$_2$-atmosphere for 65 h. The reaction mixture was poured out into ice-water (300 mL), and the product was extracted with Et$_2$O (2×). The combined organic layers were washed with brine, dried over MgSO$_4$, filtered, and evaporated under reduced pressure. The residue was purified by flash chromatography (Stationary phase: Biotage® Snap Ultra silica 100 g, Mobile phase: heptane/EtOAc gradient 100/0 to 90/10). The desired fractions were combined, evaporated under reduced pressure, and co-evaporated with heptane to give 2-methyl-4-(trifluoromethyl)-6-((trimethylsilyl)ethynyl)aniline 4b (5.5 g).

Synthesis of Intermediate 4c:

2-Methyl-4-(trifluoromethyl)-6-((trimethylsilyl)ethynyl)aniline 4b (5.5 g, 20.3 mmol) was dissolved in NMP (80 mL). Potassium tert-butoxide (6.82 g, 60.8 mmol) was added and the reaction mixture was stirred at 75° C. for 18 h under N$_2$-atm. The reaction was cooled to room temperature and poured out into ice-water (400 mL). The product was extracted with 2-MeTHF (2×). The combined organic layers were washed with brine, dried over MgSO$_4$, filtered, and evaporated under reduced pressure. The residue was purified by flash chromatography (Stationary phase: Biotage® Snap Ultra silica 100 g, Mobile phase: heptane/EtOAc gradient 100/0 to 80/20). The desired fractions were combined, evaporated under reduced pressure, and co-evaporated with toluene. The residue was dried under vacuum at 50° C. to give 7-methyl-5-(trifluoromethyl)-1H-indole 4c (0.95 g)

Synthesis of Intermediate 4d:

A solution of 7-methyl-5-(trifluoromethyl)-1H-indole 4c (0.95 g, 4.77 mmol) in DMF (15 mL) was cooled to 0° C. Under a N$_2$ flow, sodium hydride (1.09 g, 28.4 mmol) was added portionwise. The mixture was stirred at 0° C. for 20 min. A solution of tosyl chloride (1.0 g, 5.25 mmol) in DMF (10 mL) was added dropwise and the resulting mixture was stirred at 0° C. for 20 min and at room temperature for 40 min. The mixture was poured out into ice-water (100 mL) and vigorously stirred for 1 h. The precipitate was filtered off, washed with water (4×) and dried at 50° C. under vacuum to give 7-methyl-1-tosyl-5-(trifluoromethyl)-1H-indole 4d (1.64 g).

Synthesis of Intermediate 4e:

Titanium(IV) chloride (1.02 mL, 9.28 mmol) was added dropwise at room temperature to a stirred solution of 7-methyl-1-tosyl-5-(trifluoromethyl)-1H-indole 4d (1.64 g, 4.64 mmol) and 2-(4-fluoro-2-methoxyphenyl)acetyl chloride 1a' (1.88 g, 9.28 mmol) in dichloromethane (50 mL). The reaction was stirred at room temperature for 3 h. The reaction was quenched by the addition of crushed ice (40 g). After stirring for 1 h, the layers were separated. The organic layer was dried over MgSO$_4$, filtered, and the solvent was concentrated under reduced pressure. The residue was purified by flash chromatography (stationary phase: Biotage® Snap Ultra silica 50 g, Mobile phase: heptane/CH$_2$Cl$_2$ gradient 100/0 to 0/100). The desired fractions were combined, concentrated under reduced pressure, and co-evaporated with dioxane. The residue was dried under vacuum at 50° C. to provide 2-(4-fluoro-2-methoxyphenyl)-1-(7-methyl-1-tosyl-5-(trifluoromethyl)-1H-indol-3-yl)ethanone 4e (1.57 g).

Synthesis of Intermediate 4f:

Potassium hydroxide (0.52 g, 9.27 mmol) was added to a solution of 2-(4-fluoro-2-methoxyphenyl)-1-(7-methyl-1-tosyl-5-(trifluoromethyl)-1H-indol-3-yl)ethanone 4e (1.38 g, 2.66 mmol) in dioxane (30 mL) and water (10 mL). The mixture was stirred overnight at room temperature. The reaction mixture was poured out slowly into a stirring mixture of ice-water (50 mL) and 1N HCl (11 mL). After stirring for 5 minutes, the product was extracted with 2-MeTHF (2×). The combined organic layers were washed with brine, dried over MgSO$_4$, filtered off, and evaporated under reduced pressure. The residue was stirred up in CH$_2$Cl$_2$ (4 mL), filtered off, washed with CH$_2$Cl$_2$ (4×1 mL), and dried under vacuum at 50° C. to provide 2-(4-fluoro-2-methoxyphenyl)-1-(7-methyl-5-(trifluoromethyl)-1H-indol-3-yl)ethanone 4f (0.51 g).

Synthesis of Intermediate 4g:

A solution of 2-(4-fluoro-2-methoxyphenyl)-1-(7-methyl-5-(trifluoromethyl)-1H-indol-3-yl)ethanone 4f (0.51 g, 1.4 mmol) in THF (20 mL) was cooled to 0° C., under N$_2$ atmosphere. Phenyltrimethylammonium tribromide [CAS 4207-56-1] (0.55 g, 1.47 mmol) was added. The mixture was stirred at 0° C. for 40 min, and at room temperature for 90 min. The precipitate was filtered off and washed with THF(2×). The combined filtrates were concentrated under reduced pressure to give 2-bromo-2-(4-fluoro-2-methoxyphenyl)-1-(7-methyl-5-(trifluoromethyl)-1H-indol-3-yl)ethanone 4g (0.62 g), which was used as such in the next step without further purification.

Synthesis of Compound 4 and Chiral Separation into Enantiomers 4A and 4B:

A mixture of 2-bromo-2-(4-fluoro-2-methoxyphenyl)-1-(7-methyl-5-(trifluoromethyl)-1H-indol-3-yl)ethanone 4g (0.62 g, 1.4 mmol), 2-(3-amino-5-methoxyphenoxy)ethanol [CAS 725237-16-1] (0.511 g, 2.8 mmol) and diisopropylethylamine (481 µL, 2.8 mmol) in CH$_3$CN (30 mL) was stirred at room temperature for 21 h and at 40° C. for 6 h. The reaction mixture was poured out into water (125 mL) and the product was extracted with Et$_2$O (2×). The combined organic layers were dried over MgSO$_4$, filtered, and the solvent was evaporated under reduced pressure. The residue was purified by flash chromatography (stationary phase: Grace Reveleris® silica 12 g, Mobile phase: heptane/EtOAc/EtOH gradient 100/0/0 to 40/45/15). The fractions containing Compound 4 were combined and the solvent was evaporated under reduced pressure. The residue was further purified via preparative HPLC (Stationary phase: RP XBridge® C18 OBD—10 µm, 50×150 mm, Mobile phase: 0.25% NH$_4$HCO$_3$ solution in water, CH$_3$CN). The desired fractions were combined and concentrated under reduced pressure to a residual volume of ~5 mL. The resulting solution was kept standing for 70 h to allow precipitation of the product. The product was filtered off, washed with H$_2$O (4×), and dried under vacuum at 45° C. to provide 2-(4-fluoro-2-methoxyphenyl)-2-((3-(2-hydroxyethoxy)-5-methoxyphenyl)amino)-1-(7-methyl-5-(trifluoromethyl)-1H-indol-3-yl)ethanone (Compound 4, 340 mg) as a racemic mixture.

The enantiomers of Compound 4 (297 mg) were separated via Normal Phase Chiral separation (Stationary phase: Whelk-O1 (R,R), Mobile phase: 80% heptane, 20% ethanol) to give Enantiomer 4A as the first eluted product and Enantiomer 4B as the second eluted product. Both Enantiomers were further purified by flash chromatography (stationary phase: Grace Reveleris® silica 12 g, mobile phase: heptane/EtOAc/EtOH gradient 100/0/0 to 40/45/15). The desired fractions were combined and evaporated under reduced pressure. The residue was stirred up in H$_2$O (5 mL)+MeOH (1.25 mL), filtered off, washed 4× with H$_2$O/MeOH 4/1, and dried under vacuum at 45° C. to provide Enantiomer 4A (79 mg) and Enantiomer 4B (60 mg).

Compound 4:

$^1$H NMR (400 MHz, DMSO-d$_6$) δ ppm 2.55 (s, 3H) 3.61 (s, 3H) 3.64 (q, J=5.2 Hz, 2H) 3.77-3.89 (m, 2H) 3.95 (s, 3H) 4.76 (t, J=5.5 Hz, 1H) 5.72 (t, J=2.1 Hz, 1H) 5.95 (d, J=2.2 Hz, 2H) 6.19 (d, J=7.9 Hz, 1H) 6.35 (d, J=8.1 Hz, 1H) 6.73 (td, J=8.5, 2.4 Hz, 1H) 6.93 (dd, J=11.4, 2.4 Hz, 1H) 7.35 (br s, 1H) 7.38 (dd, J=8.7, 6.9 Hz, 1H) 8.32 (br s, 1H) 8.56 (d, J=3.3 Hz, 1H) 12.46 (br d, J=2.6 Hz, 1H)

LC/MS (method LC-B): R$_t$ 2.11 min, MH$^+$ 547

Enantiomer 4A:

$^1$H NMR (400 MHz, DMSO-d$_6$) δ ppm 2.55 (s, 3H) 3.61 (s, 3H) 3.64 (q, J=5.3 Hz, 2H) 3.76-3.90 (m, 2H) 3.96 (s, 3H) 4.77 (t, J=5.5 Hz, 1H) 5.72 (t, J=2.1 Hz, 1H) 5.95 (d, J=2.0 Hz, 2H) 6.20 (d, J=8.1 Hz, 1H) 6.35 (d, J=8.1 Hz, 1H) 6.73 (td, J=8.5, 2.5 Hz, 1H) 6.93 (dd, J=11.3, 2.5 Hz, 1H) 7.35 (br s, 1H) 7.38 (dd, J=8.6, 7.0 Hz, 1H) 8.33 (br s, 1H) 8.56 (s, 1H) 12.46 (br s, 1H)

LC/MS (method LC-B): R$_t$ 2.09 min, MH$^+$ 547

[α]$_D^{20}$: −80.4° (c 0.495, DMF)

Chiral SFC (method SFC-D): R$_t$ 3.20 min, MH$^+$ 547, chiral purity 99.6%.

Enantiomer 4B:

$^1$H NMR (400 MHz, DMSO-d$_6$) δ ppm 2.55 (s, 3H) 3.61 (s, 3H) 3.64 (q, J=5.3 Hz, 2H) 3.77-3.90 (m, 2H) 3.95 (s, 3H) 4.76 (t, J=5.5 Hz, 1H) 5.72 (t, J=2.1 Hz, 1H) 5.95 (d, J=2.0 Hz, 2H) 6.20 (d, J=8.1 Hz, 1H) 6.35 (d, J=7.9 Hz, 1H) 6.73 (td, J=8.5, 2.4 Hz, 1H) 6.93 (dd, J=11.4, 2.4 Hz, 1H) 7.35 (br s, 1H) 7.38 (dd, J=8.6, 7.0 Hz, 1H) 8.32 (br s, 1H) 8.56 (s, 1H) 12.46 (s, 1H)

LC/MS (method LC-B): R$_t$ 2.09 min, MH$^+$ 547

[α]$_D^{20}$: +74.1° (c 0.425, DMF)

Chiral SFC (method SFC-D): R$_t$ 2.91 min, MH$^+$ 547, chiral purity 96.9%.

Example 5: synthesis 2-(4-fluoro-2-methoxyphenyl)-2-((3-(2-hydroxyethoxy)-5-methoxyphenyl)amino)-1-(5-(trifluoromethoxy)-1H-indol-3-yl)ethanone (Compound 5) and Chiral Separation into Enantiomers 5A and 5B

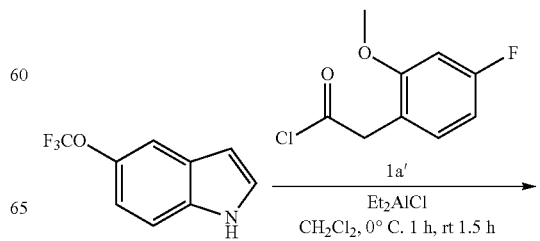

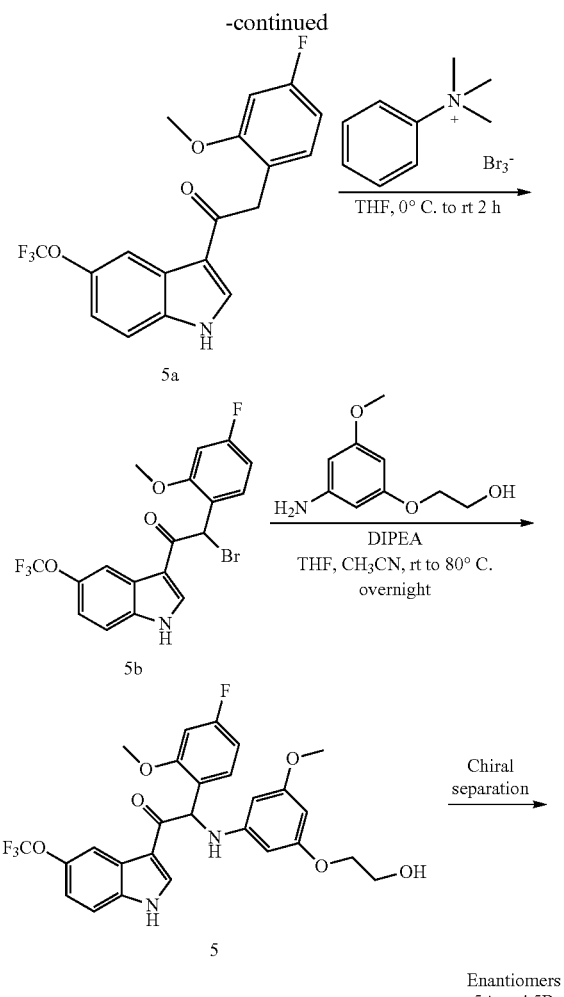

Synthesis of Intermediate 5a:

A solution of 5-(trifluoromethoxy)-1H-indole [CAS 262593-63-5] (5 g, 24.9 mmol) in CH$_2$Cl$_2$ (150 mL) was cooled to 0° C. under N$_2$-atmosphere. A solution of diethylaluminum chloride 1M in hexane (37.3 mL, 37.3 mmol) was added dropwise and the resulting mixture was kept at 0° C. for 15 min. A solution of 2-(4-fluoro-2-methoxyphenyl) acetyl chloride 1a' (7.05 g, 34.8 mmol) in CH$_2$Cl$_2$ (50 mL) was added dropwise. Stirring was continued at 0° C. for 1 h and at room temperature for 1.5 h. The reaction mixture was poured out in a stirring ice/Rochelle salt solution. After the ice had melted, the mixture was filtered over Dicalite® and the filter cake was washed several times with THF. The filtrates were combined. The layers were separated and the organic layer washed with brine, dried over MgSO$_4$, filtered and evaporated under reduced pressure. The residue was triturated with CH$_2$Cl$_2$ (50 mL) and the precipitate was filtered off to provide 2-(4-fluoro-2-methoxyphenyl)-1-(5-(trifluoromethoxy)-1H-indol-3-yl)ethanone 5a (7.36 g). The filtrate was concentrated under vacuum and the solid residue was stirred up in CH$_2$Cl$_2$ (10 mL). Filtration of the solids provided a second crop of 5a (431 mg).

Synthesis of Intermediate 5b:

A stirred solution of 2-(4-fluoro-2-methoxyphenyl)-1-(5-(trifluoromethoxy)-1H-indol-3-yl)ethanone 5a (7.35 g, 20.0 mmol) in THF (200 mL) was cooled to 0° C. A solution of phenyltrimethylammonium tribromide [CAS 4207-56-1] (8.28 g, 22.0 mmol) in THF (100 mL) was added dropwise. The resulting suspension was stirred at room temperature for 2 h. The solids were removed by filtration and washed with THF. The combined filtrates were evaporated under reduced pressure. The residue was mixed with EtOAc (30 mL). The solids were isolated by filtration, washed with a small amount of EtOAc and dried under vacuum at 50° C. to provide 2-bromo-2-(4-fluoro-2-methoxyphenyl)-1-(5-(trifluoromethoxy)-1H-indol-3-yl)ethanone 5b (7.8 g), which was used without further purification in the next step.

Synthesis of Compound 5 and Chiral Separation of Enantiomers 5A and 5B

A mixture of 2-bromo-2-(4-fluoro-2-methoxyphenyl)-1-(5-(trifluoromethoxy)-1H-indol-3-yl)ethanone 5b (3 g, 6.72 mmol), 2-(3-amino-5-methoxyphenoxy)ethanol [CAS 725237-16-1] (1.85 g, 10.1 mmol) and diisopropylethylamine (1.16 mL, 6.72 mmol) in THF (150 mL) and CH$_3$CN (150 mL) was stirred at room temperature overnight. The reaction temperature was increased to 60° C. for 6 h and subsequently to 80° C. overnight. The reaction mixture was concentrated under reduced pressure. The residue was dissolved in CH$_2$Cl$_2$, washed with 1N HCl (100 mL) and water (100 mL), dried over MgSO$_4$, filtered and evaporated under reduced pressure. The residue was purified by flash chromatography (Stationary phase: Grace Reveleris® silica 120 g, Mobile phase: EtOAc:EtOH(3:1)/heptane gradient 0/100 to 50/50). The desired fractions were combined and evaporated under reduced pressure. The residue was further purified via preparative HPLC (Stationary phase: RP XBridge® Prep C18 OBD~10 μm, 50×150 mm, Mobile phase: 0.25% NH$_4$HCO$_3$ solution in water, CH$_3$CN). The desired fractions were combined and evaporated under reduced pressure to give 2-(4-fluoro-2-methoxyphenyl)-2-((3-(2-hydroxyethoxy)-5-methoxyphenyl)amino)-1-(5-(trifluoromethoxy)-1H-indol-3-yl)ethanone (Compound 5, 1.18 g) as a racemic mixture.

The chiral separation of the enantiomers of Compound 5 (1.18 g) was performed via preparative SFC (Stationary phase: Chiralcel® Diacel OD 20×250 mm, Mobile phase: CO$_2$, EtOH+0.4% iPrNH$_2$). The product fractions were combined and evaporated to provide Enantiomer 5A as the first eluted product and Enantiomer 5B as the second eluted product.

Enantiomer 5A (0.46 g) was purified by flash chromatography (Stationary phase Grace Reveleris® silica 12 g, Mobile phase: heptane/EtOAc/EtOH gradient 100/0/0 to 40/45/15). The desired fractions were combined and evaporated under reduced pressure and co-evaporated with a mixture of Et$_2$O and heptane. The residual foam was triturated with H$_2$O (7.5 mL) and MeOH (2.5 mL). The solids were filtered off, washed (4×) with a mixture of H$_2$O/MeOH 3/1, and dried at under vacuum at 45° C. to provide Enantiomer 5A (291 mg).

Enantiomer 5B (0.46 g) was purified by flash chromatography (stationary phase Grace Reveleris® silica 12 g, mobile phase: heptane/EtOAc/EtOH gradient 100/0/0 to 40/45/15). The desired fractions were combined and evaporated under reduced pressure and co-evaporated twice with MeOH. The residue was triturated with H$_2$O (7.5 mL) and MeOH (2.5 mL). The solids were filtered off, washed (4×) with a mixture of H$_2$O/MeOH 3/1, and dried at under vacuum at 45° C. to provide Enantiomer 5B (351 mg).

Compound 5:

$^1$H NMR (360 MHz, DMSO-d$_6$) δ ppm 3.60 (s, 3H) 3.64 (q, J=5.0 Hz, 2H) 3.75-3.89 (m, 2H) 3.94 (s, 3H) 4.80 (t, J=5.5 Hz, 1H) 5.72 (t, J=2.0 Hz, 1H) 5.93 (d, J=1.8 Hz, 2H) 6.15 (d, J=8.1 Hz, 1H) 6.40 (d, J=8.1 Hz, 1H) 6.74 (td, J=8.5, 2.4 Hz, 1H) 6.93 (dd, J=11.3, 2.6 Hz, 1H) 7.21 (dd, J=8.8, 2.2 Hz, 1H) 7.38 (dd, J=8.4, 7.0 Hz, 1H) 7.58 (d, J=8.8 Hz, 1H) 8.06 (br s, 1H) 8.55 (s, 1H) 12.23 (br s, 1H)

LC/MS (method LC-A): $R_t$ 1.20 min, MH$^+$ 549

Enantiomer 5A:

$^1$H NMR (400 MHz, DMSO-d$_6$) δ ppm 3.61 (s, 3H) 3.64 (q, J=5.3 Hz, 2H) 3.76-3.89 (m, 2H) 3.94 (s, 3H) 4.77 (t, J=5.5 Hz, 1H) 5.72 (t, J=2.1 Hz, 1H) 5.93 (d, J=2.0 Hz, 2H) 6.15 (d, J=8.1 Hz, 1H) 6.37 (d, J=7.9 Hz, 1H) 6.73 (td, J=8.5, 2.5 Hz, 1H) 6.93 (dd, J=11.2, 2.4 Hz, 1H) 7.20 (dd, J=8.8, 1.8 Hz, 1H) 7.38 (dd, J=8.6, 7.0 Hz, 1H) 7.58 (d, J=8.8 Hz, 1H) 8.06 (d, J=0.9 Hz, 1H) 8.53 (s, 1H) 12.26 (br s, 1H)

LC/MS (method LC-A): $R_t$ 1.12 min, MH$^+$ 549

$[\alpha]_D^{20}$: −93.5° (c 0.445, DMF)

Chiral SFC (method SFC-D): $R_t$ 3.16 min, MH$^+$ 549, chiral purity 100%.

Enantiomer 5B:

$^1$H NMR (400 MHz, DMSO-d$_6$) δ ppm 3.61 (s, 3H) 3.64 (q, J=5.2 Hz, 2H) 3.77-3.90 (m, 2H) 3.95 (s, 3H) 4.77 (t, J=5.6 Hz, 1H) 5.72 (t, J=2.1 Hz, 1H) 5.94 (d, J=2.0 Hz, 2H) 6.15 (d, J=8.1 Hz, 1H) 6.37 (d, J=8.1 Hz, 1H) 6.73 (td, J=8.5, 2.4 Hz, 1H) 6.93 (dd, J=11.4, 2.4 Hz, 1H) 7.21 (dd, J=8.7, 1.9 Hz, 1H) 7.38 (dd, J=8.6, 7.0 Hz, 1H) 7.58 (d, J=8.8 Hz, 1H) 8.07 (d, J=0.9 Hz, 1H) 8.53 (s, 1H) 12.26 (br s, 1H)

LC/MS (method LC-A): $R_t$ 1.12 min, MH$^+$ 549

$[\alpha]_D^{20}$: +95.1° (c 0.465, DMF)

Chiral SFC (method SFC-D): $R_t$ 2.86 min, MH$^+$ 549, chiral purity 100%.

Example 6: 2-(4-fluoro-2-methoxyphenyl)-2-((3-(2-hydroxyethoxy)-5-methoxyphenyl)amino)-1-(6-methoxy-5-(trifluoromethoxy)-1H-indol-3-yl)ethanone (Compound 6) and Chiral Separation into Enantiomers 6A and 6B

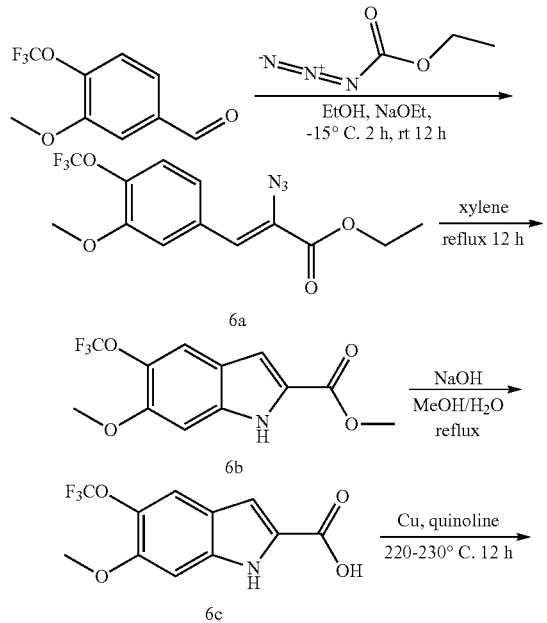

Synthesis of Intermediate 6a:

To a cooled (−15° C.) solution of 3-methoxy-4-(trifluoromethoxy)benzaldehyde [CAS 853771-90-1] (50 g, 230 mmol) and ethyl azidoacetate (89 g, 690 mmol) in EtOH (400 mL) was added dropwise, over a period of 2 h, a solution of NaOEt (0.69 mol, prepared from 15.9 g Na and 700 mL of EtOH). The reaction mixture was stirred at room temperature overnight. After cooling on an ice-bath, the reaction was quenched with a saturated NH$_4$Cl solution (1.2 L), and stirred for 10 min. The precipitate was filtered off, washed with water, and dried to give (Z)-ethyl 2-azido-3-(3-methoxy-4-(trifluoromethoxy)phenyl)acrylate 6a (32 g) as a yellowish solid.

Synthesis of Intermediate 6b:

A solution of (Z)-ethyl 2-azido-3-(3-methoxy-4-(trifluoromethoxy)phenyl)acrylate 6a (3 g, 10 mmol) in xylene (40 mL) was heated under reflux overnight. After cooling to room temperature, the solvent was evaporated to dryness. The residue was triturated with hexane (50 mL) and the precipitate was filtered off to afford methyl 6-methoxy-5-(trifluoromethoxy)-1H-indole-2-carboxylate 6b (yield: 1.4-1.6 g) as a yellow solid.

Synthesis of Intermediate 6c:

To a mixture of methyl 6-methoxy-5-(trifluoromethoxy)-1H-indole-2-carboxylate 6b (25 g, 87 mmol) in MeOH/H$_2$O (2/1, 300 mL) was added NaOH (7 g, 175 mmol) and the mixture was heated under reflux until a clear solution was obtained. After cooling to room temperature, most of the methanol was removed under reduced pressure and the remaining aqueous solution was acidified with conc. HCl to pH 3-4. The product was extracted with EtOAc (2×250 mL). The combined organic layers were washed with brine, dried, and evaporated under reduced pressure to give 6-methoxy-5-(trifluoromethoxy)-1H-indole-2-carboxylic acid 6c (22.7 g) as a grey solid.

Synthesis of Intermediate 6d:

A suspension of 6-methoxy-5-(trifluoromethoxy)-1H-indole-2-carboxylic acid 6c (7.5 g, 27 mmol) and Cu (1.22 g, 0.7 equiv.) in quinoline (150 mL) was heated to 220-230° C. under inert atmosphere for 12 h. After cooling to room temperature, the mixture was diluted with methyl tert-butyl ether (MTBE, 400 mL) and washed with a saturated aqueous NaHSO$_4$ solution (2×500 mL). The organic layer was dried over MgSO$_4$, filtered through short pad of silica gel, and evaporated under reduced pressure. The residue was purified by column chromatography to afford 6-methoxy-5-(trifluoromethoxy)-1H-indole 6d (3.75 g) as a yellow solid.

Synthesis of Intermediate 6e:

Under a N$_2$ flow, diethylaluminum chloride 1M in hexane (8.45 mL, 8.45 mmol) was added dropwise to a cooled (0° C.) solution of 6-methoxy-5-(trifluoromethoxy)-1H-indole 6d (1.3 g, 5.62 mmol) in CH$_2$Cl$_2$ (25 mL). After 30 min of stirring at 0° C., a solution of 2-(4-fluoro-2-methoxyphenyl) acetyl chloride 1a' (1.71 g, 8.45 mmol) in CH$_2$Cl$_2$ (15 mL) was added dropwise. The mixture was stirred at 0° C. for 3 h. Ice-water was added. The precipitate was filtered off and dried under vacuum to give 2-(4-fluoro-2-methoxyphenyl)-1-(6-methoxy-5-(trifluoromethoxy)-1H-indol-3-yl)ethanone 6e (2 g).

Synthesis of Intermediate 6f:

At 0° C., a solution of phenyltrimethylammonium tribromide [CAS 4207-56-1] (1.7 g, 4.28 mmol) in THF (60 mL) was added dropwise to a mixture of 2-(4-fluoro-2-methoxyphenyl)-1-(6-methoxy-5-(trifluoromethoxy)-1H-indol-3-yl) ethanone 6e (1.6 g, 4.28 mmol) in THF (60 mL). The mixture was stirred at 0° C. for 1 h and at room temperature for 4 h. The precipitate was filtered off and washed with EtOAc. The combined filtrates were concentrated under reduced pressure. The residue was dissolved in EtOAc. The organic layer was washed with water, dried over MgSO$_4$, filtered, and evaporated under reduced pressure. The residue was taken up with diisopropyl ether. The precipitate was filtered off and dried to give 2-bromo-2-(4-fluoro-2-methoxyphenyl)-1-(6-methoxy-5-(trifluoromethoxy)-1H-indol-3-yl)ethanone 6f (1.9 g).

Synthesis of Compound 6 and Chiral Separation into Enantiomers 6A and 6B:

A mixture of 2-bromo-2-(4-fluoro-2-methoxyphenyl)-1-(6-methoxy-5-(trifluoromethoxy)-1H-indol-3-yl)ethanone 6f (2.08 g, 4.37 mmol), 2-(3-amino-5-methoxyphenoxy) ethanol [CAS 725237-16-1] (0.96 g, 5.24 mmol) and diisopropylethylamine (1.13 mL, 6.55 mmol) in CH$_3$CN (100 mL) was stirred at 70° C. for 6 h and then concentrated under reduced pressure. The residue was diluted with CH$_2$Cl$_2$ and washed with 1N HCl. The organic layer was separated, dried over MgSO$_4$, filtered, and the solvent was evaporated under reduced pressure. The residue was purified by column chromatography on silica gel (15-40 µm, 80 g, CH$_2$Cl$_2$/MeOH 99/1). The fractions containing Compound 6 were combined and the solvent was evaporated under reduced pressure. The residue (1 g) was purified again via achiral SFC (Stationary phase: Diethylaminopropyl 5 µm 150×21.2 mm, Mobile phase: 60% CO$_2$, 40% MeOH+0.3% iPrNH$_2$) to give, after crystallization from diisopropyl ether/petroleum ether, 2-(4-fluoro-2-methoxyphenyl)-2-((3-(2-hydroxyethoxy)-5-methoxyphenyl)amino)-1-(6-methoxy-5-(trifluoromethoxy)-1H-indol-3-yl)ethanone (Compound 6, 650 mg) as a racemic mixture.

The enantiomers of Compound 6 were separated via Preparative Chiral SFC (Stationary phase: Chiralpack® IC 5 µm 250×2 0 mm, Mobile phase: 70% CO$_2$, 30% iPrOH+0.3% iPrNH$_2$) to give, after solidification from heptane/diisopropyl ether, 244 mg of the first eluted Enantiomer 6A and 254 mg of the second eluted Enantiomer 6B.

Compound 6:

$^1$H NMR (400 MHz, DMSO-d$_6$) δ ppm 3.54-3.69 (m, 5H) 3.76-3.90 (m, 5H) 3.95 (s, 3H) 4.75 (br t, J=5.3 Hz, 1H) 5.72 (s, 1H) 5.92 (d, J=2.0 Hz, 2H) 6.12 (d, J=8.1 Hz, 1H) 6.33 (d, J=8.1 Hz, 1H) 6.73 (td, J=8.5, 2.3 Hz, 1H) 6.92 (dd, J=11.4, 2.3 Hz, 1H) 7.20 (s, 1H) 7.37 (dd, J=8.1, 7.1 Hz, 1H) 8.02 (s, 1H) 8.38 (s, 1H) 12.03 (br s, 1H)

LC/MS (method LC-C): R$_t$ 3.02 min, MH$^+$ 579

Melting point: 178° C.

Enantiomer 6A:

$^1$H NMR (500 MHz, DMSO-d$_6$) δ ppm 3.57-3.68 (m, 5H) 3.77-3.89 (m, 5H) 3.95 (s, 3H) 4.77 (t, J=5.5 Hz, 1H) 5.71 (t, J=2.1 Hz, 1H) 5.92 (d, J=1.9 Hz, 2H) 6.12 (d, J=7.9 Hz, 1H) 6.36 (d, J=7.9 Hz, 1H) 6.73 (td, J=8.4, 2.4 Hz, 1H) 6.93 (dd, J=11.4, 2.5 Hz, 1H) 7.21 (s, 1H) 7.37 (dd, J=8.5, 6.9 Hz, 1H) 8.02 (d, J=1.3 Hz, 1H) 8.39 (s, 1H) 11.97 (br s, 1H)

LC/MS (method LC-C): R$_t$ 3.00 min, MH$^+$ 579

[α]$_D^{20}$: +73.9° (c 0.2367, DMF)

Chiral SFC (method SFC-B): R$_t$ 2.09 min, MH$^+$ 579, chiral purity 100%.

Enantiomer 6B:

$^1$H NMR (500 MHz, DMSO-d$_6$) δ ppm 3.56-3.68 (m, 5H) 3.78-3.87 (m, 5H) 3.95 (s, 3H) 4.78 (t, J=5.5 Hz, 1H) 5.71 (t, J=2.1 Hz, 1H) 5.92 (d, J=1.9 Hz, 2H) 6.12 (d, J=8.2 Hz, 1H) 6.36 (d, J=7.9 Hz, 1H) 6.73 (td, J=8.5, 2.5 Hz, 1H) 6.93 (dd, J=11.2, 2.4 Hz, 1H) 7.21 (s, 1H) 7.37 (dd, J=8.5, 6.9 Hz, 1H) 8.02 (d, J=1.3 Hz, 1 H) 8.39 (s, 1H) 11.98 (br s, 1H)

LC/MS (method LC-C): R$_t$ 3.00 min, MH$^+$ 579

[α]$_D^{20}$: −73.7° (c 0.2658, DMF)

Chiral SFC (method SFC-B): R$_t$ 4.41 min, MH$^+$ 579, chiral purity 100%.

Example 7: synthesis of 2-(4-fluoro-2-methoxyphenyl)-1-(6-fluoro-5-(trifluoromethoxy)-1H-indol-3-yl)-2-((3-(2-hydroxyethoxy)-5-methoxyphenyl) amino)ethanone (Compound 7) and Chiral Separation into Enantiomers 7A and 7B

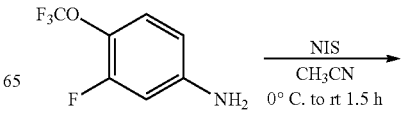

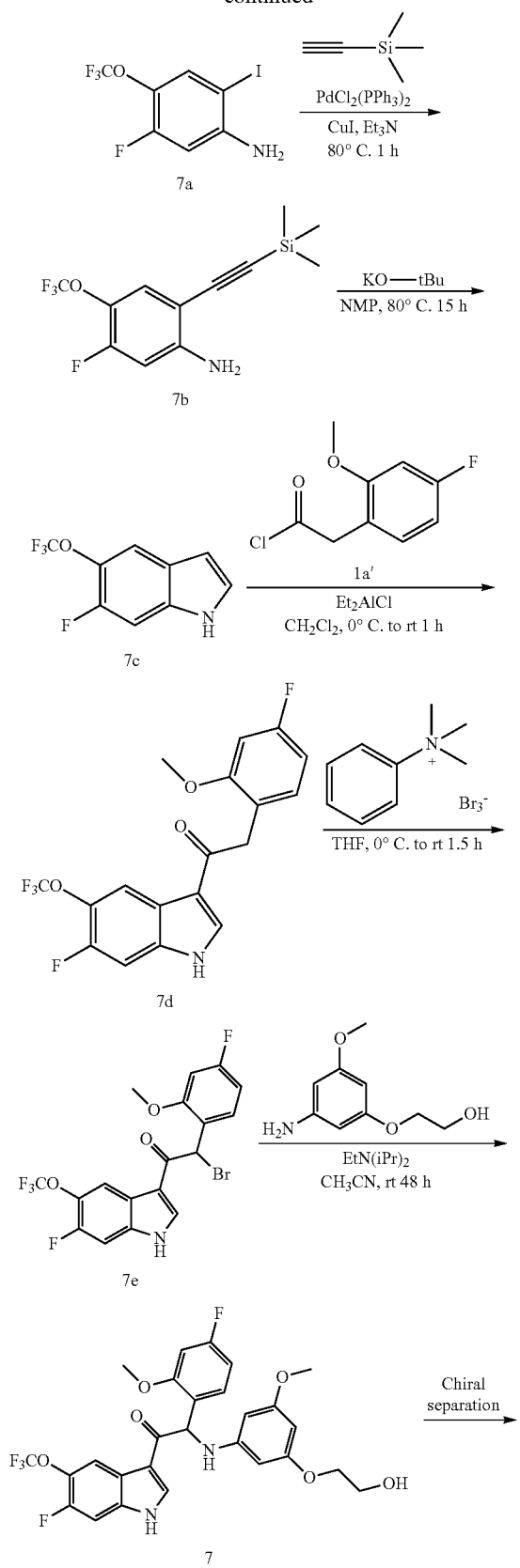

Synthesis of Intermediate 7a:

A solution of 3-fluoro-4-(trifluoromethoxy)aniline [CAS 1017779-69-9] (32.0 g, 164 mmol) in $CH_3CN$ (600 mL) was stirred on an ice-bath. N-iodo-succinimide (40.59 g, 180.4 mmol) was added and the reaction mixture was allowed to slowly reach room temperature while stirring overnight. The solvent was concentrated under reduced pressure. Water was added and the product was extracted with EtOAc (2×300 mL). The combined organic layers were washed with and an aqueous solution of $Na_2S_2O_3$ (500 mL), brine (500 mL), dried over $MgSO_4$, filtered, and concentrated under reduced pressure. The residue was purified by column chromatography on silica gel (eluent: petroleum ether/EtOAc gradient 50/1 to 30/1). The desired fractions were combined and evaporated under reduced pressure to provide 5-fluoro-2-iodo-4-(trifluoromethoxy)aniline 7a (45 g).

Synthesis of Intermediate 7b:

To a solution of 5-fluoro-2-iodo-4-(trifluoromethoxy)aniline 7a (43.0 g, 134 mmol) and trimethylsilylacetylene (39.5 g, 401.9 mmol) in triethylamine (650 mL) were added dichlorobis(triphenylphosphine)palladium(II) (3.76 g, 5.36 mmol) and copper(I) iodide (2.55 g, 13.4 mmol) and the reaction mixture was stirred at 80° C. for 1 h. The reaction mixture was concentrated under reduced pressure. The residue was purified by column chromatography on silica gel (eluent: petroleum ether/EtOAc gradient 50/1 to 30/1). The desired fractions were combined and evaporated under reduced pressure to give 5-fluoro-4-(trifluoromethoxy)-2-((trimethylsilyl)ethynyl)aniline 7b (36.5 g).

Synthesis of Intermediate 7c:

5-fluoro-4-(trifluoromethoxy)-2-((trimethylsilyl)ethynyl)aniline 7b (36.0 g, 123.6 mmol) was dissolved in NMP (500 mL). Potassium tert-butoxide (41.6 g, 370.7 mmol) was added and the reaction mixture was stirred at 80° C. for 15 h. The reaction was cooled to room temperature and quenched with water. The product was extracted with MTBE (3×500 mL). The combined organic layers were washed with brine (2×1 L), dried over $MgSO_4$, filtered, and evaporated under reduced pressure. The residue was purified by flash chromatography (Stationary phase: SepaFlash® silica 330 g, Mobile phase: gradient 0 to 2% EtOAc in petroleum ether). The desired fractions were combined and evaporated under reduced pressure. The residue was further purified by distillation under reduced pressure to give 6-fluoro-5-(trifluoromethoxy)-1H-indole 7c (18.2 g) as a pale yellow oil.

Synthesis of Intermediate 7d:

A solution of 6-fluoro-5-(trifluoromethoxy)-1H-indole 7c (1.59 g, 7.26 mmol) in $CH_2Cl_2$ (150 mL) was cooled to 0° C. under $N_2$-atmosphere. A solution of diethylaluminum chloride 1M in hexane (10.9 mL, 10.9 mmol) was added dropwise and the resulting mixture was kept at 0° C. for 30 min. A solution of 2-(4-fluoro-2-methoxyphenyl)acetyl chloride 1a' (2.2 g, 10.9 mmol) in $CH_2Cl_2$ (75 mL) was added dropwise. Stirring was continued at 0° C. for 1 h and at room temperature for 1 h. The reaction mixture was cooled to 0° C. and a solution of potassium sodium tartrate tetrahydrate (Rochelle salt, 4.1 g, 14.5 mmol) in water (6 mL) was added dropwise and the mixture was stirred for 30 min at 0° C. The reaction mixture was allowed to warm to room temperature and THF (200 mL) and $Na_2SO_4$ (25 g) were added. After overnight stirring, the mixture was filtered over Dicalite® and the filter cake was washed several times with THF (4×150 mL). The filtrates were combined and evaporated under reduced pressure. The solid residue was stirred up in a solvent mixture of DIPE (25 mL) and EtOAc (2 mL). The solids were filtered off, washed with DIPE (3×)

and dried at 50° C. under vacuum to provide 2-(4-fluoro-2-methoxyphenyl)-1-(6-fluoro-5-(trifluoromethoxy)-1H-indol-3-yl)ethanone 7d (2.6 g).

Synthesis of Intermediate 7e:

A solution of 2-(4-fluoro-2-methoxyphenyl)-1-(6-fluoro-5-(trifluoromethoxy)-1H-indol-3-yl)ethanone 7d (2.60 g, 6.75 mmol) in THF (130 mL) was cooled to 0° C., under N$_2$ atmosphere. Phenyltrimethylammonium tribromide [CAS 4207-56-1] (2.66 g, 7.09 mmol) was added. The mixture was stirred at 0° C. for 45 min, and at room temperature for 90 min. The precipitate was filtered off and washed with THF (2×). The combined filtrates were concentrated under reduced pressure to give 2-bromo-2-(4-fluoro-2-methoxyphenyl)-1-(6-fluoro-5-(trifluoromethoxy)-1H-indol-3-yl)ethanone 7e (3.6 g), which was used as such in the next step without further purification.

Synthesis of Compound 7 and Chiral Separation into Enantiomers 7A and 7B:

A mixture of 2-bromo-2-(4-fluoro-2-methoxyphenyl)-1-(6-fluoro-5-(trifluoromethoxy)-1H-indol-3-yl)ethanone 7e (3.59 g, 7.73 mmol), 2-(3-amino-5-methoxyphenoxy)ethanol [CAS 725237-16-1] (2.83 g, 15.5 mmol) and diisopropylethylamine (2.67 mL, 15.5 mmol) in CH$_3$CN was stirred at room temperature for 48 h. The reaction mixture was poured out into water (250 mL) and the product was extracted with Et20 (2×). The combined organic layers were dried over MgSO$_4$, filtered, and the solvent was evaporated under reduced pressure. The residue was purified by flash chromatography (Stationary phase: Grace Reveleris® silica 100 g, Mobile phase: heptane/EtOAc/EtOH gradient 100/0/0 to 40/45/15). The product fractions were combined and the solvent was evaporated under reduced pressure. The residue was further purified via preparative HPLC (Stationary phase: Uptisphere® C18 ODB—10 µm, 200 g, 5 cm, Mobile phase: 0.25% NH$_4$HCO$_3$ solution in water, CH$_3$CN). The desired fractions were combined and concentrated under reduced pressure. The residue, containing racemic 2-(4-fluoro-2-methoxyphenyl)-1-(6-fluoro-5-(trifluoromethoxy)-1H-indol-3-yl)-2-((3-(2-hydroxyethoxy)-5-methoxyphenyl)amino)ethanone (Compound 7, 1.29 g) was submitted to chiral separation using preparative SFC (Stationary phase: Chiralcel® Diacel OD 20×250 mm, Mobile phase: CO$_2$, EtOH+0.4% iPrNH$_2$) to give Enantiomer 7A as the first eluted product and Enantiomer 7B as the second eluted product. Both enantiomers were further purified by column chromatography (Stationary phase: Grace Reveleris® Silica 12 g, Mobile phase: EtOAc:EtOH(3:1)/heptane gradient 0/100 to 40/60) and subsequently by preparative HPLC (Stationary phase: RP XBridge® Prep C18 OBD—10 µm, 30×150 mm, Mobile phase: 0.25% NH$_4$HCO$_3$ solution in water, MeOH). The desired fractions were combined and evaporated under reduced pressure. Both enantiomers were precipitated from a solution in MeOH, by slow addition of water. The solids were filtered off and dried at 50° C. under vacuum to provide Enantiomer 7A (42 mg) and Enantiomer 7B (278 mg).

Enantiomer 7A:

$^1$H NMR (360 MHz, DMSO-d$_6$) δ ppm 3.60 (s, 3H) 3.63 (q, J=5.4 Hz, 2H) 3.76-3.88 (m, 2H) 3.93 (s, 3H) 4.80 (t, J=5.5 Hz, 1H) 5.71 (t, J=2.0 Hz, 1H) 5.92 (d, J=2.2 Hz, 2H) 6.14 (d, J=8.1 Hz, 1H) 6.40 (d, J=8.1 Hz, 1H) 6.74 (td, J=8.5, 2.4 Hz, 1H) 6.93 (dd, J=11.5, 2.4 Hz, 1H) 7.36 (dd, J=8.4, 7.0 Hz, 1H) 7.60 (d, J=10.6 Hz, 1H) 8.16 (dd, J=8.1, 1.1 Hz, 1H) 8.54 (s, 1H) 12.32 (br s, 1H)

LC/MS (method LC-A): R$_t$ 1.16 min, MH$^+$ 567

[α]$_D^{20}$: −77.1° (c 0.305, DMF)

Chiral SFC (method SFC-D): R$_t$ 3.00 min, MH$^+$ 567, chiral purity 100%.

Enantiomer 7B:

$^1$H NMR (360 MHz, DMSO-d$_6$) δ ppm 3.60 (s, 3H) 3.63 (q, J=5.4 Hz, 2H) 3.76-3.88 (m, 2H) 3.93 (s, 3H) 4.80 (t, J=5.5 Hz, 1H) 5.71 (t, J=2.0 Hz, 1H) 5.92 (d, J=2.2 Hz, 2H) 6.14 (d, J=8.1 Hz, 1H) 6.41 (d, J=8.1 Hz, 1H) 6.74 (td, J=8.4, 2.6 Hz, 1H) 6.93 (dd, J=11.3, 2.6 Hz, 1H) 7.37 (dd, J=8.4, 7.0 Hz, 1H) 7.60 (d, J=10.4 Hz, 1H) 8.16 (dd, J=7.7, 1.1 Hz, 1H) 8.54 (s, 1H) 12.33 (br s, 1H) LC/MS (method LC-A): R$_t$ 1.16 min, MH$^+$ 567

[α]$_D^{20}$: +84.0° (c 0.455, DMF)

Chiral SFC (method SFC-D): R$_t$ 2.73 min, MH$^+$ 567, chiral purity 100%.

Example 8: synthesis 2-(4-fluoro-2-methoxyphenyl)-2-((3-(2-hydroxyethoxy)-5-methoxyphenyl)amino)-1-(7-methyl-5-(trifluoromethoxy)-1H-indol-3-yl)ethanone (Compound 8) and Chiral Separation into Enantiomers 8A and 8B

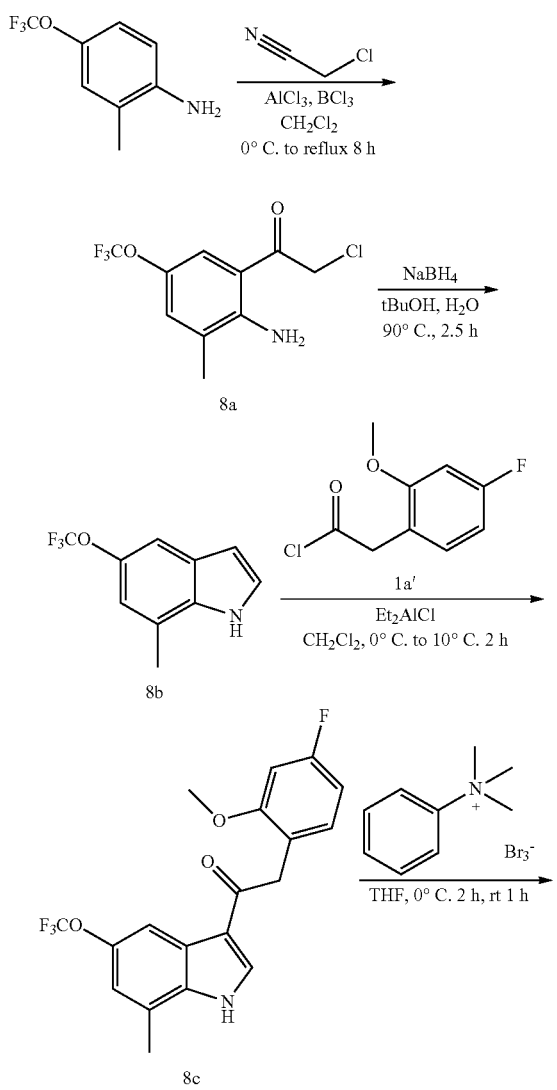

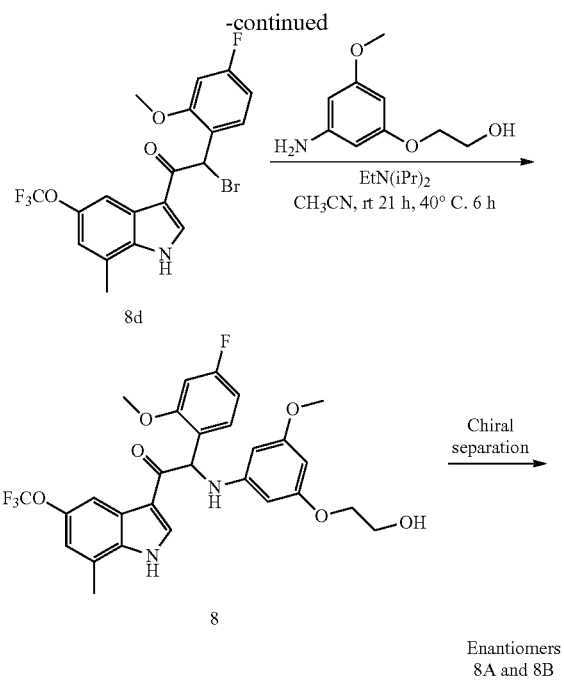

Synthesis of Intermediate 8a:

A mixture of boron(III) chloride 1M in CH$_2$Cl$_2$ (25.5 mL, 25.5 mmol) and aluminum(III) chloride (3.40 g, 25.5 mmol) was diluted with CH$_2$Cl$_2$ (20 mL) and cooled on an ice-bath under N$_2$-atmosphere. A solution of 2-methyl-4-(trifluoromethoxy)aniline [CAS 86256-59-9] (4.88 g, 25.5 mmol) and chloroacetonitrile (3.24 mL, 51.0 mmol) in CH$_2$Cl$_2$ (7.5 mL) was added dropwise. After addition, the ice-bath was removed and the mixture was heated under reflux for 8 h. The mixture was cooled again to 0° C. using an ice-bath. 2N HCl (75 mL) was added dropwise, causing heavy precipitation. The resulting suspension was heated under reflux for 90 min, and cooled to room temperature. The solids were removed by filtration. The filter cake was washed with CH$_2$Cl$_2$ (4×). The filtrates were combined and the phases were separated. The organic layer was isolated, washed with an aqueous NaHCO$_3$ solution, dried over MgSO$_4$, filtered and evaporated under reduced pressure. The residue was purified by flash chromatography (Stationary phase: Biotage® SNAP Ultra Silica 100 g, Mobile phase: heptane/CH$_2$Cl$_2$ gradient 100/0 to 0/100). The desired fractions were combined and concentrated to a residual volume of 30 mL. The precipitate was filtered off, washed with heptane and CH$_2$Cl$_2$, and dried under vacuum at 50° C. to provide 1-(2-amino-3-methyl-5-(trifluoromethoxy)phenyl)-2-chloroethanone 8a (1.37 g). The filtrate was concentrated under reduced pressure. The solid residue was stirred up in a mixture of heptane (20 mL) and diisopropyl ether (3 mL), filtered off, washed with heptane (3×) and dried under vacuum at 50° C. to provide a second fraction of 8a (0.24 g).

Synthesis of Intermediate 8b:

Sodium borohydride (326 mg, 8.61 mmol) was added to a stirred solution of 1-(2-amino-3-methyl-5-(trifluoromethoxy)phenyl)-2-chloroethanone 8a (1.92 g, 7.17 mmol) in tert-butanol (50 mL) and water (5 mL). The reaction mixture was stirred at room temperature of 30 min and at 90° C. for 2.5 h. Water (50 mL) was added and the product was extracted with diethyl ether (2×). The combined organic layers were washed with brine, dried over MgSO$_4$, filtered and evaporated under reduced pressure. The residue was purified by flash chromatography (Stationary phase: Biotage® SNAP Ultra Silica 25 g, Mobile phase: heptane/EtOAc gradient 100/0 to 20/80). The desired fractions were combined, concentrated under reduced pressure, co-evaporated with heptane and dried under vacuum at 50° C. to provide 7-methyl-5-(trifluoromethoxy)-1H-indole 8b (1.2 g).

Synthesis of Intermediate 8c:

A solution of 7-methyl-5-(trifluoromethoxy)-1H-indole 8b (1.2 g, 5.58 mmol) in CH$_2$Cl$_2$ (75 mL) was cooled to 0° C. under N$_2$-atmosphere. A solution of diethylaluminum chloride 1M in hexane (8.36 mL, 8.36 mmol) was added dropwise over 1 min to the stirred solution and the resulting mixture was kept at 0° C. for 10 min. A solution of 2-(4-fluoro-2-methoxyphenyl)acetyl chloride 1a' (1.69 g, 8.36 mmol) in CH$_2$Cl$_2$ (25 mL) was added dropwise while keeping the internal temperature of the reaction mixture below 5° C. The reaction mixture was stirred at 0° C. for 2 h and at 10° C. for 2 h. The reaction mixture was cooled again to 0° C. and the reaction was quenched by the slow addition of a solution of potassium sodium tartrate tetrahydrate (Rochelle salt) [CAS 6100-16-9] (3.15 g, 11.2 mmol) in water (3.5 mL). After stirring for an additional 10 min at 0° C., the ice-bath was removed and the resulting mixture was diluted with THF (75 mL). Na$_2$SO$_4$ (10 g) was added and after overnight stirring, the mixture was filtered over Dicalite®. The filter cake was washed with THF. The combined filtrates were evaporated under reduced pressure. The solid residue was stirred up in a small amount of CH$_3$CN, filtered off, washed with CH$_3$CN (2×) and dried under vacuum at 50° C. to provide 2-(4-fluoro-2-methoxyphenyl)-1-(7-methyl-5-(trifluoromethoxy)-1H-indol-3-yl)ethanone 8c (1.82 g).

Synthesis of Intermediate 8d:

A stirred solution of 2-(4-fluoro-2-methoxyphenyl)-1-(7-methyl-5-(trifluoromethoxy)-1H-indol-3-yl)ethanone 8c (1.82 g, 4.77 mmol) in THF (40 mL) was cooled to 0° C. under N$_2$-atmosphere. Phenyltrimethylammonium tribromide [CAS 4207-56-1] (1.88 g, 5.01 mmol) was added. The resulting suspension was stirred at 0° C. for 2 h and at room temperature for 1 h. The solids were removed by filtration and washed with THF (3×). The combined filtrates were evaporated under reduced pressure to provide 2-bromo-2-(4-fluoro-2-methoxyphenyl)-1-(7-methyl-5-(trifluoromethoxy)-1H-indol-3-yl)ethanone 8d (2.20 g), which was used without further purification in the next step.

Synthesis of Compound 8 and Chiral Separation of Enantiomers 8A and 8B:

A mixture of 2-bromo-2-(4-fluoro-2-methoxyphenyl)-1-(7-methyl-5-(trifluoromethoxy)-1H-indol-3-yl)ethanone 8d (2.20 g, 4.77 mmol), 2-(3-amino-5-methoxyphenoxy)ethanol [CAS 725237-16-1] (1.75 g, 9.55 mmol) and diisopropylethylamine (1.65 mL, 9.55 mmol) in THF (40 mL) and CH$_3$CN (60 mL) was stirred at room temperature for 5 days. The reaction mixture was concentrated under reduced pressure. The residue was purified by flash chromatography (Stationary phase: Grace Reveleris® silica 120 g, Mobile phase: heptane/EtOAc/EtOH gradient 100/0/0 to 40/45/15). The desired fractions were combined and evaporated under reduced pressure. The residue was further purified via preparative HPLC (Stationary phase: Uptisphere® C18 ODB—10 μm, 200 g, 5 cm, Mobile phase: 0.25% NH$_4$HCO$_3$ solution in water, CH$_3$CN). The desired fractions were combined and evaporated under reduced pressure to a residual volume of 300 mL. The precipitate that was formed during the evaporation was filtered off, washed with H$_2$O (5×), and dried under vacuum at 50° C. to provide 2-(4-fluoro-2-methoxyphenyl)-2-((3-(2-hydroxyethoxy)-5-methoxyphenyl)amino)-1-(7-methyl-5-(trifluoromethoxy)-1H-indol-3-yl)ethanone (Compound 8, 1.28 g) as a racemic mixture.

The chiral separation of the enantiomers of Compound 8 (1.2 g) was performed via normal phase chiral separation (Stationary phase: AS 20 µm, Mobile phase: 100% methanol). The product fractions were combined and evaporated to provide Enantiomer 8A as the first eluted product and Enantiomer 8B as the second eluted product. Enantiomer 8A (0.54 g) was further purified by flash chromatography (stationary phase Grace Reveleris® silica 12 g, Mobile phase: heptane/EtOAc/EtOH gradient 100/0/0 to 40/45/15). The desired fractions were combined and evaporated under reduced pressure. The residue was stirred up in H$_2$O (2.5 mL) and MeOH (0.75 mL). After stirring for 15 minutes, the product was filtered off, washed (3×) with a mixture of H$_2$O/MeOH 3/1, and dried under vacuum at 50° C. to provide Enantiomer 8A (425 mg). Enantiomer 8B (0.45 g) was further purified by flash chromatography (Stationary phase Grace Reveleris® silica 12 g, Mobile phase: heptane/EtOAc/EtOH gradient 100/0/0 to 40/45/15]. The desired fractions were combined and evaporated under reduced pressure. The residue was stirred up in H$_2$O (2.5 mL) and MeOH (0.75 mL). After stirring for 15 minutes, the product was filtered off, washed (3×) with a mixture of H$_2$O/MeOH 3/1, and dried under vacuum at 50° C. to provide Enantiomer 8B (275 mg).

Compound 8:

$^1$H NMR (400 MHz, DMSO-d$_6$) δ ppm 2.50 (s, 3H) 3.61 (s, 3H) 3.64 (q, J=5.4 Hz, 2H) 3.83 (qt, J=10.1, 5.1 Hz, 2H) 3.95 (s, 3H) 4.76 (t, J=5.5 Hz, 1H) 5.72 (t, J=2.1 Hz, 1H) 5.94 (d, J=2.0 Hz, 2H) 6.17 (d, J=7.9 Hz, 1H) 6.35 (d, J=7.9 Hz, 1H) 6.73 (td, J=8.5, 2.4 Hz, 1H) 6.93 (dd, J=11.3, 2.5 Hz, 1H) 7.04 (br s, 1H) 7.37 (dd, J=8.6, 7.0 Hz, 1H) 7.90 (br s, 1H) 8.51 (d, J=2.9 Hz, 1H) 12.33 (br s, 1H)

LC/MS (method LC-B): R$_t$ 2.13 min, MH$^+$ 563

Enantiomer 8A:

$^1$H NMR (400 MHz, DMSO-d$_6$) δ ppm 2.50 (s, 3H) 3.61 (s, 3H) 3.64 (q, J=5.2 Hz, 2H) 3.77-3.89 (m, 2H) 3.95 (s, 3H) 4.78 (t, J=5.5 Hz, 1H) 5.72 (t, J=2.1 Hz, 1H) 5.94 (d, J=2.2 Hz, 2H) 6.17 (d, J=8.1 Hz, 1H) 6.37 (d, J=8.1 Hz, 1H) 6.73 (td, J=8.5, 2.4 Hz, 1H) 6.93 (dd, J=11.3, 2.5 Hz, 1H) 7.04 (br s, 1H) 7.37 (dd, J=8.6, 7.0 Hz, 1H) 7.90 (br s, 1H) 8.51 (d, J=3.3 Hz, 1H) 12.35 (d, J=2.6 Hz, 1H)

LC/MS (method LC-A): R$_t$ 1.16 min, MH$^+$ 563

[α]$_D^{20}$: +77.8° (c 0.445, DMF)

Chiral SFC (method SFC-D): R$_t$ 2.82 min, MH$^+$ 563, chiral purity 100%.

Enantiomer 8B:

$^1$H NMR (400 MHz, DMSO-d$_6$) δ ppm 2.50 (s, 3H) 3.61 (s, 3H) 3.64 (q, J=5.4 Hz, 2H) 3.83 (qt, J=10.2, 5.1 Hz, 2H) 3.95 (s, 3H) 4.76 (t, J=5.5 Hz, 1H) 5.72 (t, J=2.1 Hz, 1H) 5.94 (d, J=2.0 Hz, 2H) 6.17 (d, J=7.9 Hz, 1H) 6.35 (d, J=7.9 Hz, 1H) 6.73 (td, J=8.5, 2.5 Hz, 1H) 6.93 (dd, J=11.4, 2.4 Hz, 1H) 7.04 (br s, 1H) 7.37 (dd, J=8.6, 7.0 Hz, 1H) 7.90 (br s, 1H) 8.51 (d, J=3.1 Hz, 1H) 12.33 (br d, J=2.2 Hz, 1H)

LC/MS (method LC-A): R$_t$ 1.16 min, MH$^+$ 563

[α]$_D^{20}$: −77.9° (c 0.465, DMF)

Chiral SFC (method SFC-D): R$_t$ 3.19 min, MW 563, chiral purity 100%.

Example 9: synthesis of 2-(4-chloro-2-methoxyphenyl)-2-((3-(2-hydroxyethoxy)-5-methoxyphenyl)amino)-1-(5-(trifluoromethyl)-1H-indol-3-yl)ethanone (Compound 9) and Chiral Separation into Enantiomers 9A and 9B

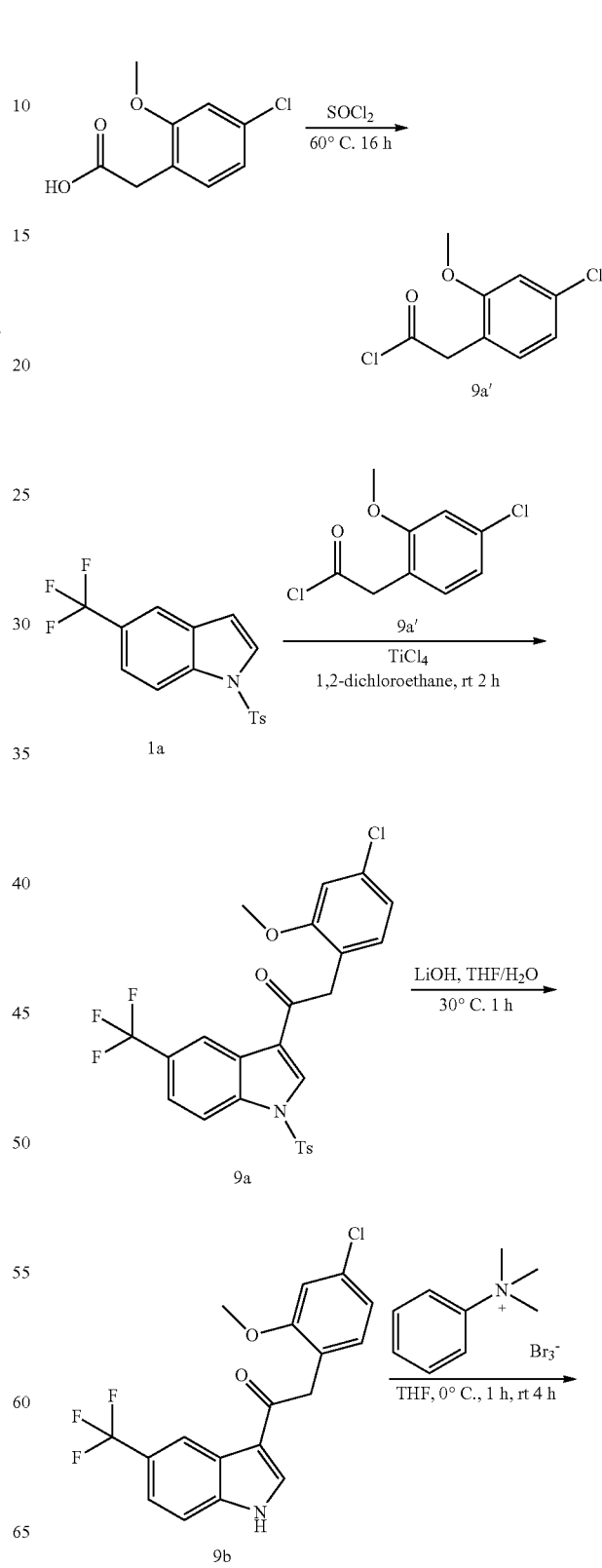

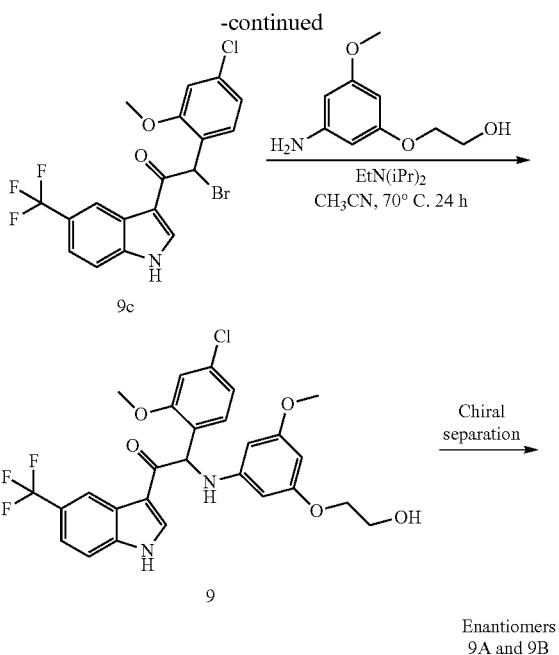

Synthesis of Intermediate 9a':

2-(4-Chloro-2-methoxyphenyl)acetic acid [CAS 170737-95-8] (5.8 g, 28.9 mmol) was added in small portions to thionyl chloride (50 mL) and the resulting solution was stirred overnight at 60° C. The solvent was concentrated under reduced pressure and co-evaporated with toluene to give 2-(4-chloro-2-methoxyphenyl)-acetyl chloride 9a' (6.5 g) as an oily residue that was used without further purification in the next step.

Synthesis of Intermediate 9a:

Titanium(IV) chloride (2.32 mL, 21.2 mmol) was added dropwise at room temperature to a solution of 1-tosyl-5-(trifluoromethyl)-1H-indole 1a (3.7 g, 10.95 mmol) and 2-(4-chloro-2-methoxyphenyl)acetyl chloride 9a' (4.8 g, 21.9 mmol) in 1,2-dichloroethane (120 mL). The reaction was stirred at room temperature for 2 h. Ice-water was added. The reaction mixture was extracted with EtOAc. The organic layer was dried over MgSO$_4$, filtered, and the solvent was concentrated under reduced pressure. The residue was purified by column chromatography on silica gel (15-40 μm, 80 g, CH$_2$Cl$_2$/MeOH 99.5/0.5). The fractions containing Compound 9a were combined and the solvent was evaporated under reduced pressure. The compound was taken up with CH$_3$CN/diisopropyl ether. The precipitate was filtered off and dried to give 2-(4-chloro-2-methoxyphenyl)-1-(1-tosyl-5-(trifluoromethyl)-1H-indol-3-yl)ethanone 9a (2.8 g).

Synthesis of Intermediate 9b:

Lithium hydroxide (0.64 g, 15.3 mmol) was added to a solution of 2-(4-chloro-2-methoxyphenyl)-1-(1-tosyl-5-(trifluoromethyl)-1H-indol-3-yl)ethanone 9a (3.2 g, 6.13 mmol) in THF (18 mL) and water (6 mL). The mixture was stirred at 30° C. for 1 h. Water and EtOAc were added. The organic layer was separated, dried over MgSO$_4$, filtered, and the solvent was evaporated under reduced pressure. The solid was taken up with diisopropyl ether. The precipitate was filtered off and dried to give 2-(4-chloro-2-methoxyphenyl)-1-(5-(trifluoromethyl)-1H-indol-3-yl)ethanone 9b (2.1 g).

Synthesis of Intermediate 9c:

At 0° C., a solution of phenyltrimethylammonium tribromide [CAS 4207-56-1] (2.1 g, 5.7 mmol) in THF (60 mL) was added dropwise to a mixture of 2-(4-chloro-2-methoxyphenyl)-1-(5-(trifluoromethyl)-1H-indol-3-yl)ethanone 9b (2.15 g, 5.7 mmol) in THF (50 mL). The mixture was stirred at 0° C. for 1 h and at room temperature for 4 h. The precipitate was filtered off and washed with EtOAc. The filtrate was concentrated under reduced pressure. The residue was dissolved in EtOAc. The organic layer was washed with water, dried over MgSO$_4$, filtered, and evaporated under reduced pressure. The residue was taken up with DIPE. The precipitate was filtered off and dried to give 2-bromo-2-(4-chloro-2-methoxyphenyl)-1-(5-(trifluoromethyl)-1H-indol-3-yl)ethanone 9c (2.5 g).

Synthesis of Compound 9 and Chiral Separation into Enantiomers 9A and 9B:

A mixture of 2-bromo-2-(4-chloro-2-methoxyphenyl)-1-(5-(trifluoromethyl)-1H-indol-3-yl)ethanone 9c (1.5 g, 3.36 mmol), 2-(3-amino-5-methoxyphenoxy)ethanol [CAS 725237-16-1] (0.61 g, 3.36 mmol) and diisopropylethylamine (0.87 mL, 5.04 mmol) in CH$_3$CN (100 mL) was stirred at 70° C. for 24 h. The residue was diluted with CH$_2$Cl$_2$ and 1N HCl. The organic layer was separated, dried over MgSO$_4$, filtered, and the solvent was evaporated under reduced pressure. The residue was purified by column chromatography on silica gel (15-40 μm, 80 g, CH$_2$Cl$_2$/MeOH 99/1). The fractions containing Compound 9 were combined and the solvent was evaporated under reduced pressure. The residue (680 mg) was solidified from diisopropyl ether/CH$_3$CN to give 2-(4-chloro-2-methoxyphenyl)-2-((3-(2-hydroxyethoxy)-5-methoxyphenyl)amino)-1-(5-(trifluoromethyl)-1H-indol-3-yl)ethanone (Compound 9, 610 mg) as a racemic mixture. The enantiomers were separated via Preparative Chiral SFC (Stationary phase: Chiralcel® OD-H 5 μm 250×20 mm, Mobile phase: 70% CO$_2$, 30% EtOH) to give, after solidification in petroleum ether/diisopropyl ether, 255 mg of the first eluted Enantiomer 9A and 237 mg of the second eluted Enantiomer 9B.

Compound 9:

$^1$H NMR (500 MHz, DMSO-d$_6$) δ ppm 3.61 (s, 3H) 3.64 (q, J=5.3 Hz, 2H) 3.78-3.88 (m, 2H) 3.95 (s, 3H) 4.78 (t, J=5.5 Hz, 1H) 5.73 (t, J=2.0 Hz, 1H) 5.94 (d, J=2.2 Hz, 2H) 6.19 (d, J=8.2 Hz, 1H) 6.42 (d, J=8.2 Hz, 1H) 6.97 (dd, J=8.4, 2.0 Hz, 1H) 7.10 (d, J=1.9 Hz, 1H) 7.37 (d, J=8.5 Hz, 1H) 7.53 (dd, J=8.7, 1.7 Hz, 1H) 7.69 (d, J=8.5 Hz, 1H) 8.48 (s, 1H) 8.60 (s, 1H) 12.42 (br s, 1H)

LC/MS (method LC-C): R$_t$ 3.10 min, MH$^+$ 549

Enantiomer 9A:

$^1$H NMR (400 MHz, DMSO-d$_6$) δ ppm 3.58-3.68 (m, 5H) 3.77-3.89 (m, 2H) 3.95 (s, 3H) 4.77 (t, J=5.6 Hz, 1H) 5.73 (s, 1H) 5.94 (d, J=1.5 Hz, 2H) 6.19 (d, J=8.1 Hz, 1H) 6.41 (d, J=8.1 Hz, 1H) 6.97 (dd, J=8.3, 1.8 Hz, 1H) 7.10 (d, J=2.0 Hz, 1H) 7.37 (d, J=8.1 Hz, 1H) 7.53 (dd, J=8.3, 1.3 Hz, 1H) 7.68 (d, J=8.1 Hz, 1H) 8.48 (s, 1H) 8.59 (s, 1H) 12.40 (br s, 1H)

LC/MS (method LC-C): R$_t$ 3.15 min, MH$^+$ 549

$[α]_D^{20}$: −102.7° (c 0.2727, DMF)

Chiral SFC (method SFC-A): R$_t$ 2.35 min, MH$^+$ 549, chiral purity 100%.

Enantiomer 9B:

$^1$H NMR (400 MHz, DMSO-d$_6$) δ ppm 3.59-3.68 (m, 5H) 3.78-3.89 (m, 2H) 3.95 (s, 3H) 4.77 (t, J=5.3 Hz, 1H) 5.73 (s, 1H) 5.94 (d, J=2.0 Hz, 2H) 6.19 (d, J=8.1 Hz, 1H) 6.41 (d, J=8.1 Hz, 1H) 6.97 (dd, J=8.3, 1.8 Hz, 1H) 7.10 (d, J=1.5 Hz, 1H) 7.37 (d, J=8.1 Hz, 1H) 7.53 (dd, J=8.6, 1.0 Hz, 1H) 7.68 (d, J=8.6 Hz, 1H) 8.48 (s, 1H) 8.59 (s, 1H) 12.33 (br s, 1H)

LC/MS (method LC-C): R$_t$ 3.15 min, MH$^+$ 549

[α]$_D^{20}$: +124.7° (c 0.2727, DMF)

Chiral SFC (method SFC-A): R$_t$ 3.88 min, MH$^+$ 549, chiral purity 100%.

Example 10: 2-(4-chloro-2-methoxyphenyl)-2-((3-(2-hydroxyethoxy)-5-methoxyphenyl)amino)-1-(6-methoxy-5-(trifluoromethyl)-1H-indol-3-yl)ethanone (Compound 10)

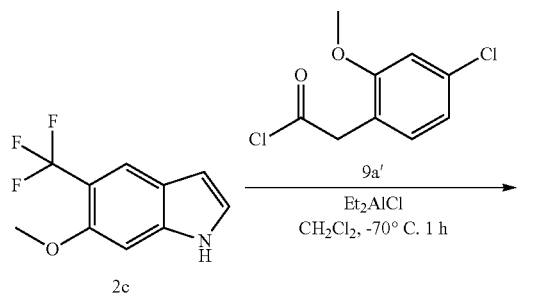

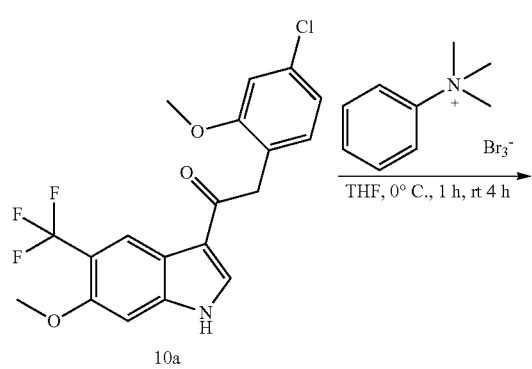

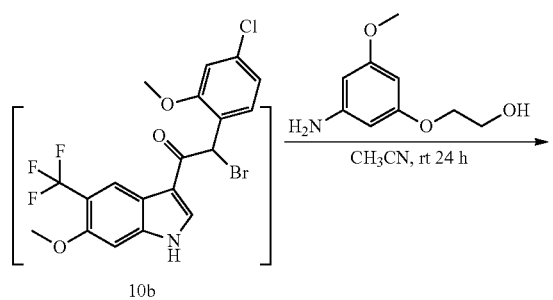

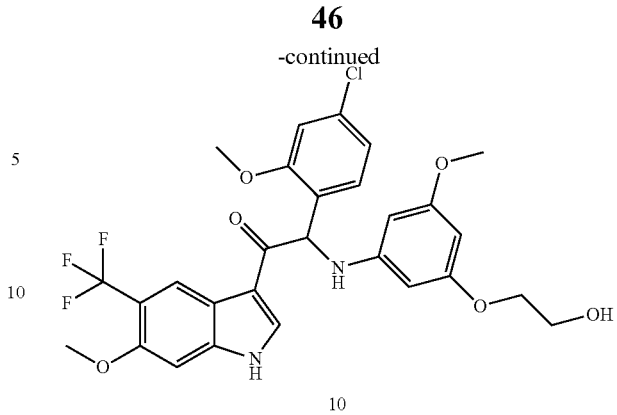

Synthesis of Intermediate 10a:

Under N$_2$-flow, diethylaluminum chloride 1M in hexane (19.17 mL, 19.17 mmol) was added dropwise at −70° C. to a solution of 6-methoxy-5-(trifluoromethyl)-1H-indole 2c (2.75 g, 12.8 mmol) in CH$_2$Cl$_2$ (30 mL). After 5 min of stirring at −70° C., 2-(4-chloro-2-methoxyphenyl)acetyl chloride 9a' (4.2 g, 19.17 mmol) in CH$_2$Cl$_2$ (30 mL) was added dropwise. The mixture was stirred at −70° C. for 1 h. Ice-water was added. The mixture was extracted with EtOAc. The organic layer was dried over MgSO$_4$, filtered and the solvent was evaporated under reduced pressure. The residue was crystallized from CH$_2$Cl$_2$, and the precipitate was filtered off. The crude product was purified by flash chromatography on silica gel (15-40 μm, 120 g, heptane/EtOAc 50/50). The pure fractions were combined and evaporated to dryness to afford, after solidification from diisopropyl ether/CH$_3$CN, 250 mg of 2-(4-chloro-2-methoxyphenyl)-1-(6-methoxy-5-(trifluoromethyl)-1H-indol-3-yl)ethanone 10a.

Synthesis of Compound 10:

At 0° C., a solution of phenyltrimethylammonium tribromide [CAS 4207-56-1] (236 mg, 0.628 mmol) in THF (5 mL) was added dropwise to a mixture of 2-(4-chloro-2-methoxyphenyl)-1-(6-methoxy-5-(trifluoromethyl)-1H-indol-3-yl)ethanone 10a (250 mg, 0.628 mmol) in THF (5 mL). The mixture was stirred at 0° C. for 1 h and at room temperature for 4 h. A solution of 2-(3-amino-5-methoxyphenoxy)ethanol [CAS 725237-16-1] (345 mg, 1.88 mmol) in CH$_3$CN (5 mL) was added dropwise and stirring was continued at room temperature for 24 h. The mixture was concentrated under reduced pressure. The residue was taken up with EtOAc and was washed with 1N HCl and water. The organic layer was dried over MgSO$_4$, filtered, and the solvent was evaporated under reduced pressure. Purification was done by flash chromatography on silica gel (15-40 μm, 24 g, CH$_2$Cl$_2$/CH$_3$OH 99.5/0.5). The pure fractions were combined and evaporated to dryness to give, after crystallization in CH$_2$Cl$_2$/MeOH, 2-(4-chloro-2-methoxyphenyl)-2-((3-(2-hydroxyethoxy)-5-methoxyphenyl)amino)-1-(6-methoxy-5-(trifluoromethyl)-1H-indol-3-yl)ethanone (Compound 10) as a racemate.

Compound 10:

$^1$H NMR (500 MHz, DMSO-d$_6$) δ ppm 3.58-3.69 (m, 5H) 3.76-3.91 (m, 5H) 3.96 (s, 3H) 4.80 (br t, J=5.4 Hz, 1H) 5.73 (s, 1H) 5.93 (s, 2H) 6.16 (br d, J=7.9 Hz, 1H) 6.41 (br d, J=7.9 Hz, 1H) 6.98 (br d, J=7.9 Hz, 1H) 7.11 (s, 1H) 7.21 (s, 1H) 7.36 (d, J=8.2 Hz, 1H) 8.37 (s, 1H) 8.45 (s, 1H) 12.16 (br s, 1H)

LC/MS (method LC-C): R$_t$ 3.11 min, MH$^+$ 579

Melting point: 133° C.

Example 11: synthesis of 2-(4-chloro-2-methoxyphenyl)-1-(6-fluoro-5-(trifluoromethyl)-1H-indol-3-yl)-2-((3-(2-hydroxyethoxy)-5-methoxyphenyl)amino)ethanone (Compound 11) and Chiral Separation into Enantiomers 11A and 11B

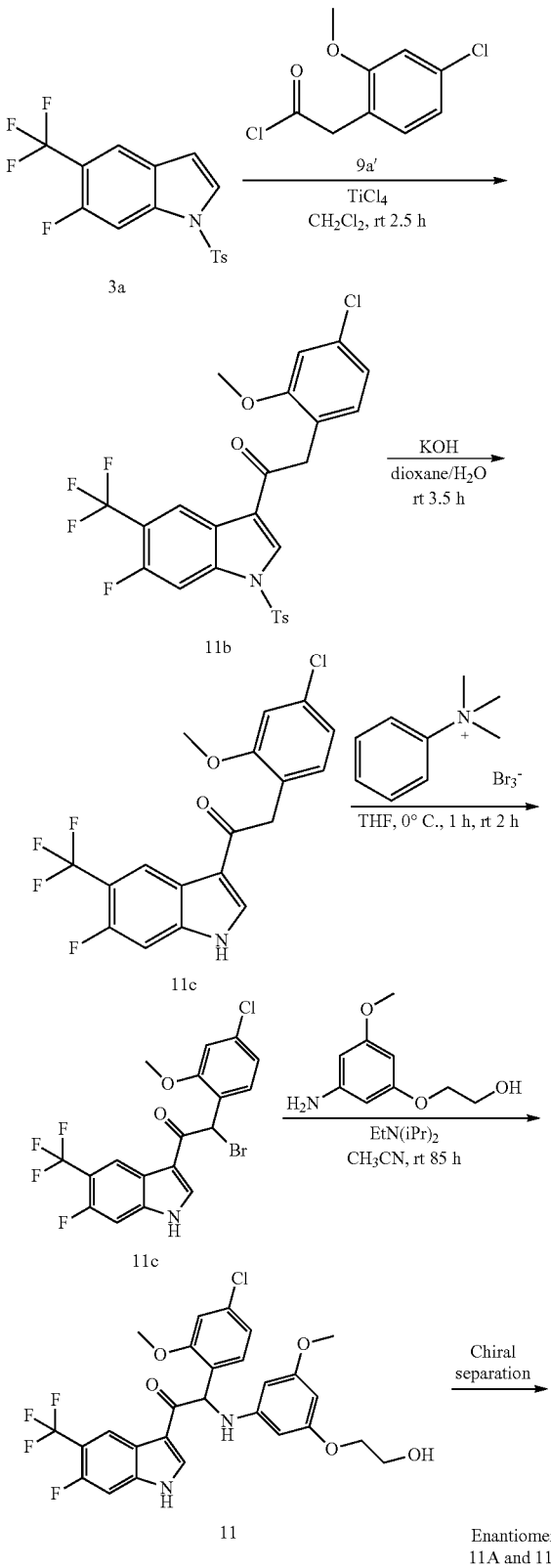

Synthesis of Intermediate 11a:

Titanium(IV) chloride (1.23 mL, 11.2 mmol) was added dropwise at room temperature to a stirred solution of 6-fluoro-1-tosyl-5-(trifluoromethyl)-1H-indole 3a (2 g, 5.6 mmol) and 2-(4-chloro-2-methoxyphenyl)acetyl chloride 9a' (2.45 g, 11.2 mmol) in dichloromethane (50 mL). The reaction was stirred at room temperature for 2.5 h. The reaction was quenched by the addition of crushed ice (40 g). After stirring for 20 min, the layers were separated. The organic layer was dried over MgSO₄, filtered, and the solvent was concentrated under reduced pressure. The residue was stirred up in diisopropyl ether (25 mL). The solids were filtered off, washed with diisopropyl ether (3×) and dried under vacuum at 50° C. to provide 2-(4-chloro-2-methoxyphenyl)-1-(6-fluoro-1-tosyl-5-(trifluoromethyl)-1H-indol-3-yl)ethanone 11a (1.82 g).

Synthesis of Intermediate 11 b:

Potassium hydroxide (0.66 g, 11.7 mmol) was added to a solution of 2-(4-chloro-2-methoxyphenyl)-1-(6-fluoro-1-tosyl-5-(trifluoromethyl)-1H-indol-3-yl)ethanone 11a (1.81 g, 3.35 mmol) in dioxane (30 mL) and water (10 mL). The mixture was stirred at room temperature for 3.5 h. The reaction mixture was poured out slowly into a stirring mixture of cold water (100 mL) and 1N HCl (15 mL). After stirring for 30 minutes, the solids were filtered off, washed with water (3×), and dried under vacuum at 50° C. to provide 2-(4-chloro-2-methoxyphenyl)-1-(6-fluoro-5-(trifluoromethyl)-1H-indol-3-yl)ethanone 11 b (1.14 g).

Synthesis of Intermediate 11c:

A solution of 2-(4-chloro-2-methoxyphenyl)-1-(6-fluoro-5-(trifluoromethyl)-1H-indol-3-yl)ethanone 11b (1.14 g, 2.95 mmol) in THF (40 mL) was cooled to 0° C., under N₂ atmosphere. Phenyltrimethylammonium tribromide [CAS 4207-56-1] (1.16 g, 3.1 mmol) was added. The mixture was stirred at 0° C. for 1 h and at room temperature for 2 h. The precipitate was filtered off and washed with THF (2×). The combined filtrates were concentrated under reduced pressure to give 2-bromo-2-(4-chloro-2-methoxyphenyl)-1-(6-fluoro-5-(trifluoromethyl)-1H-indol-3-yl)ethanone 11c (1.37 g), which was used as such in the next step without further purification.

Synthesis of Compound 11 and Chiral Separation into Enantiomers 11A and 11B:

A mixture of 2-bromo-2-(4-chloro-2-methoxyphenyl)-1-(6-fluoro-5-(trifluoromethyl)-1H-indol-3-yl)ethanone 11c (1.37 g, 2.95 mmol), 2-(3-amino-5-methoxyphenoxy)ethanol [CAS 725237-16-1] (1.08 g, 5.9 mmol) and diisopropylethylamine (1.02 mL, 5.9 mmol) in CH₃CN (60 mL) was stirred at room temperature for 85 h. The reaction mixture was poured out into water (250 mL) and the product was extracted with Et₂O (2×). The combined organic layers were dried over MgSO₄, filtered, and the solvent was evaporated under reduced pressure. The residue was purified by flash chromatography (stationary phase: Grace Reveleris® silica 12 g, Mobile phase: heptane/EtOAc/EtOH gradient 100/0/0 to 40/45/15). The fractions containing Compound 11 were combined and the solvent was evaporated under reduced pressure. The residue was further purified via preparative HPLC (Stationary phase: RP XBridge® C18 OBD—10 μm, 50×150 mm, Mobile phase: 0.25% NH₄HCO₃ solution in water, CH₃CN). The desired fractions were combined and concentrated under reduced pressure. The residue was dried under vacuum at 45° C. to provide 2-(4-chloro-2-methoxyphenyl)-1-(6-fluoro-5-(trifluoromethyl)-1H-indol-3-yl)-2-((3-(2-hydroxyethoxy)-5-methoxyphenyl)amino)ethanone (Compound 11, 151 mg) as a racemic mixture.

The chiral separation of Compound 11 (151 mg) was performed by preparative SFC (Stationary phase: Chiralcel® Diacel OD 20×250 mm, Mobile phase: $CO_2$, EtOH+ 0.4% $iPrNH_2$) to give Enantiomer 11A as the first eluted product and Enantiomer 11B as the second eluted product. Both enantiomers were solidified by precipitation from a solvent mixture of MeOH and water. The solids were filtered off, and dried under vacuum at 50° C. to provide 22 mg of Enantiomer 11A and 16 mg of Enantiomer 11B.

Enantiomer 11A:
$^1$H NMR (360 MHz, DMSO-$d_6$) δ ppm 3.61 (s, 3H) 3.62-3.67 (m, 2H) 3.76-3.89 (m, 2H) 3.94 (s, 3H) 4.80 (t, J=5.5 Hz, 1H) 5.72 (t, J=1.8 Hz, 1H) 5.93 (d, J=1.8 Hz, 2H) 6.18 (d, J=8.1 Hz, 1H) 6.43 (d, J=8.1 Hz, 1H) 6.98 (dd, J=8.2, 2.0 Hz, 1H) 7.10 (d, J=1.8 Hz, 1H) 7.36 (d, J=8.4 Hz, 1H) 7.58 (d, J=11.7 Hz, 1H) 8.45 (d, J=7.0 Hz, 1H) 8.58 (s, 1H) 12.35 (br s, 1H)

LC/MS (method LC-A): $R_t$ 1.19 min, MH$^+$ 567
$[α]_D^{20}$: +87.4° (c 0.2735, DMF)
Chiral SFC (method SFC-D): $R_t$ 3.12 min, MH$^+$ 567, chiral purity 100%.

Enantiomer 11B:
$^1$H NMR (360 MHz, DMSO-$d_6$) δ ppm 3.61 (s, 3H) 3.62-3.67 (m, 2H) 3.73-3.88 (m, 2H) 3.94 (s, 3H) 4.80 (t, J=5.5 Hz, 1H) 5.73 (br t, J=2.2 Hz, 1H) 5.93 (br d, J=2.2 Hz, 2H) 6.18 (br d, J=8.1 Hz, 1H) 6.44 (br d, J=8.4 Hz, 1H) 6.98 (br dd, J=8.1, 1.5 Hz, 1H) 7.10 (br d, J=1.1 Hz, 1H) 7.36 (d, J=8.1 Hz, 1H) 7.59 (br d, J=11.0 Hz, 1H) 8.45 (br d, J=7.3 Hz, 1H) 8.59 (s, 1H) 12.47 (br s, 1H)

LC/MS (method LC-A): $R_t$ 1.19 min, MH$^+$ 567
$[α]_D^{20}$: −86.6° (c 0.276, DMF)
Chiral SFC (method SFC-D): $R_t$ 3.43 min, MH$^+$ 567, chiral purity 99.7%.

Example 12: synthesis of 2-(4-chloro-2-methoxyphenyl)-2-((3-(2-hydroxyethoxy)-5-methoxyphenyl)amino)-1-(7-methyl-5-(trifluoromethyl)-1H-indol-3-yl)ethanone (Compound 12) and Chiral Separation into Enantiomers 12A and 12B

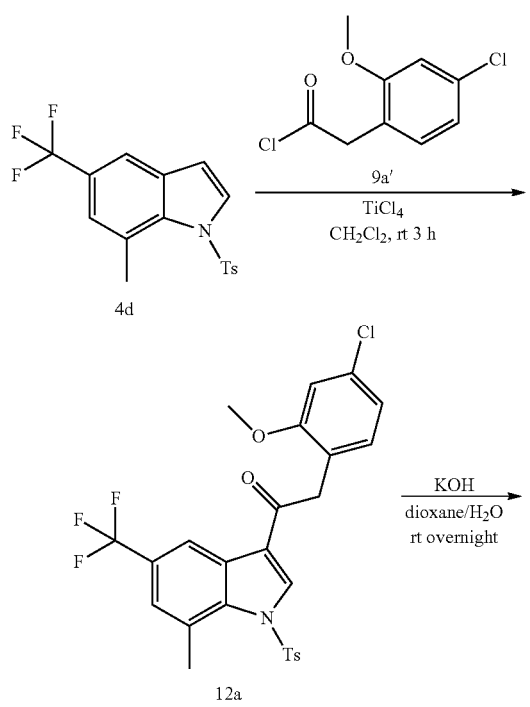

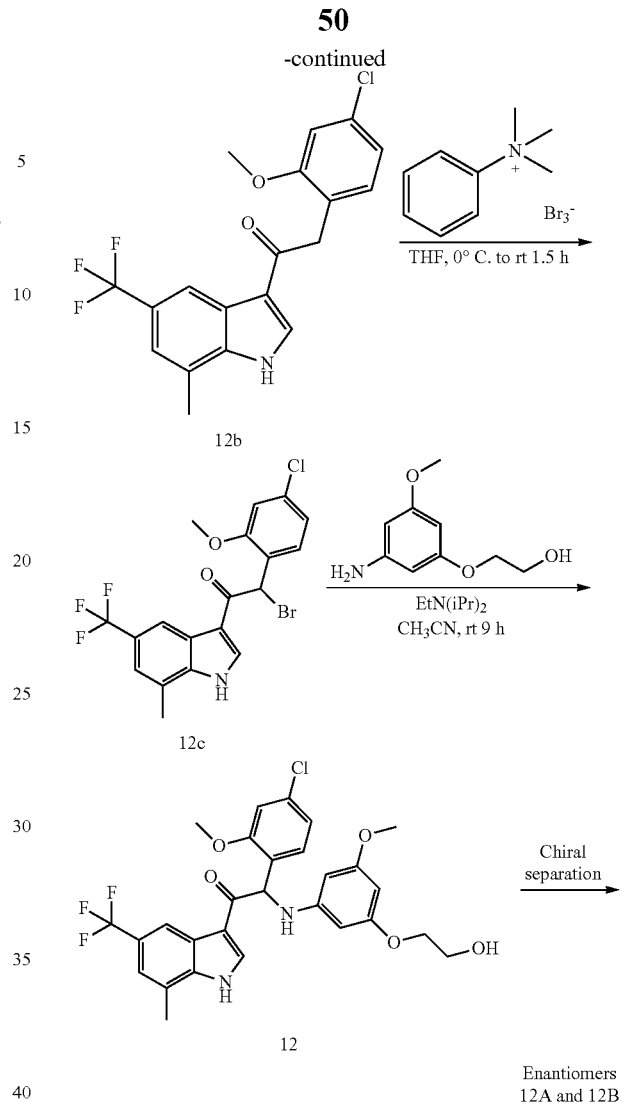

Synthesis of Intermediate 12a:
Titanium(IV) chloride (2.15 mL, 19.6 mmol) was added dropwise at room temperature to a stirred solution of 7-methyl-1-tosyl-5-(trifluoromethyl)-1H-indole 4d (3.47 g, 9.81 mmol) and 2-(4-chloro-2-methoxyphenyl)acetyl chloride 9a' (4.30 g, 19.6 mmol) in dichloromethane (50 mL). The reaction was stirred at room temperature for 3 h. The reaction was quenched by the addition of crushed ice (40 g). After stirring for 45 min, the layers were separated. The organic layer was dried over $MgSO_4$, filtered, and the solvent was concentrated under reduced pressure. The residue was purified by flash chromatography (Stationary phase: grace Reveleris® silica 120 g, Mobile phase: heptane/$CH_2Cl_2$ gradient 100/0 to 0/100). The desired fractions were combined, concentrated under reduced pressure. The residue was dried under vacuum at 50° C. to provide 2-(4-chloro-2-methoxyphenyl)-1-(7-methyl-1-tosyl-5-(trifluoromethyl)-1H-indol-3-yl)ethanone 12a (2.46 g).

Synthesis of Intermediate 12b:
Potassium hydroxide (0.90 g, 16.0 mmol) was added to a solution of 2-(4-chloro-2-methoxyphenyl)-1-(7-methyl-1-tosyl-5-(trifluoromethyl)-1H-indol-3-yl)ethanone 12a (2.46 g, 4.60 mmol) in dioxane (18 mL) and water (6 mL). The mixture was stirred overnight at room temperature. The reaction mixture was poured out slowly into a stirring mixture of ice-water (50 mL) and 1N HCl (11 mL). After stirring for 5 minutes, the product was extracted with 2-MeTHF (2×). The combined organic layers were washed with brine, dried over MgSO$_4$, filtered off, and evaporated under reduced pressure. The residue was purified by flash chromatography (Stationary phase: Biotage® Snap Ultra silica 25 g, Mobile phase: heptane/CH$_2$Cl$_2$ gradient 100/0 to 0/100). The fractions containing product were concentrated under reduced pressure and dried under vacuum at 50° C. to provide 2-(4-chloro-2-methoxyphenyl)-1-(7-methyl-5-(trifluoromethyl)-1H-indol-3-yl)ethanone 12b (0.791 mg).

Synthesis of Intermediate 12c:

A solution of 2-(4-chloro-2-methoxyphenyl)-1-(7-methyl-5-(trifluoromethyl)-1H-indol-3-yl)ethanone 12b (0.539 g, 1.4 mmol) in THF (20 mL) was cooled to 0° C., under N$_2$ atmosphere. Phenyltrimethylammonium tribromide [CAS 4207-56-1] (0.55 g, 1.47 mmol) was added. The mixture was stirred at 0° C. for 40 min, and at room temperature for 90 min. The precipitate was filtered off and washed with THF (2×). The combined filtrates were concentrated under reduced pressure to give 2-bromo-2-(4-chloro-2-methoxyphenyl)-1-(7-methyl-5-(trifluoromethyl)-1H-indol-3-yl)ethanone 12c (650 mg), which was used as such in the next step without further purification.

Synthesis of Compound 12 and Chiral Separation into Enantiomers 12A and 12B:

A mixture of 2-bromo-2-(4-chloro-2-methoxyphenyl)-1-(7-methyl-5-(trifluoromethyl)-1H-indol-3-yl)ethanone 12c (0.791 g, 1.58 mmol), 2-(3-amino-5-methoxyphenoxy)ethanol [CAS 725237-16-1] (0.579 g, 3.16 mmol) and diisopropylethylamine (544 µL, 3.16 mmol) in CH$_3$CN (30 mL) was stirred at room temperature for 9 h. The reaction mixture was poured out into water (125 mL) and the product was extracted with Et$_2$O (2×). The combined organic layers were dried over MgSO$_4$, filtered, and the solvent was evaporated under reduced pressure. The residue was purified by flash chromatography (Stationary phase: Biotage® SNAP Ultra silica 25 g, Mobile phase: heptane/EtOAc/EtOH gradient 100/0/0 to 40/45/15). The fractions containing Compound 12 were combined and the solvent was evaporated under reduced pressure to provide 2-(4-chloro-2-methoxyphenyl)-2-((3-(2-hydroxyethoxy)-5-methoxyphenyl)amino)-1-(7-methyl-5-(trifluoromethyl)-1H-indol-3-yl)ethanone (Compound 12, 604 mg) as a racemic mixture.

The enantiomers of Compound 12 (604 mg) were separated via preparative SFC (Stationary phase: Chiralcel® Diacel OD 20×250 mm, Mobile phase: CO$_2$, EtOH+0.4% iPrNH$_2$) to give Enantiomer 12A as the first eluted product and Enantiomer 12B as the second eluted product. Both enantiomers were solidified by precipitation from a solvent mixture of MeOH and water. The solids were filtered off and dried under vacuum at 50° C. to provide 199 mg of Enantiomer 12A and 185 mg of Enantiomer 12B.

Enantiomer 12A:

$^1$H NMR (360 MHz, DMSO-d$_6$) δ ppm 2.53-2.57 (m, 3H) 3.61 (s, 3H) 3.62-3.67 (m, 2H) 3.76-3.90 (m, 2H) 3.96 (s, 3H) 4.80 (t, J=5.5 Hz, 1H) 5.72 (t, J=2.2 Hz, 1H) 5.95 (d, J=1.8 Hz, 2H) 6.21 (d, J=8.1 Hz, 1H) 6.42 (d, J=8.1 Hz, 1H) 6.97 (dd, J=8.2, 2.0 Hz, 1H) 7.10 (d, J=2.2 Hz, 1H) 7.33-7.38 (m, 2H) 8.31 (br s, 1H) 8.58 (s, 1H) 12.50 (br s, 1H)

LC/MS (method LC-A): R$_t$ 1.21 min, MH$^+$ 563

[α]$_D^{20}$: +58.5° (c 0.4135, DMF)

Chiral SFC (method SFC-D): R$_t$ 3.19 min, MH$^+$ 563, chiral purity 100%.

Enantiomer 12B:

$^1$H NMR (360 MHz, DMSO-d$_6$) δ ppm 2.55 (s, 3H) 3.61 (s, 3H) 3.62-3.67 (m, 2H) 3.77-3.89 (m, 2H) 3.96 (s, 3H) 4.80 (t, J=5.5 Hz, 1H) 5.72 (t, J=2.2 Hz, 1H) 5.95 (d, J=2.2 Hz, 2H) 6.21 (d, J=8.1 Hz, 1H) 6.41 (d, J=8.4 Hz, 1H) 6.97 (dd, J=8.2, 2.0 Hz, 1H) 7.10 (d, J=1.8 Hz, 1H) 7.33-7.38 (m, 2H) 8.31 (br s, 1H) 8.58 (s, 1H) 12.48 (br s, 1H)

LC/MS (method LC-A): R$_t$ 1.21 min, MH$^+$ 563

[α]$_D^{20}$: −55.7° (c 0.469, DMF)

Chiral SFC (method SFC-D): R$_t$ 3.49 min, MH$^+$ 563, chiral purity 100%.

Example 13: synthesis 2-(4-chloro-2-methoxyphenyl)-2-((3-(2-hydroxyethoxy)-5-methoxyphenyl)amino)-1-(5-(trifluoromethoxy)-1H-indol-3-yl)ethanone (Compound 13) and Chiral Separation into Enantiomers 13A and 13B

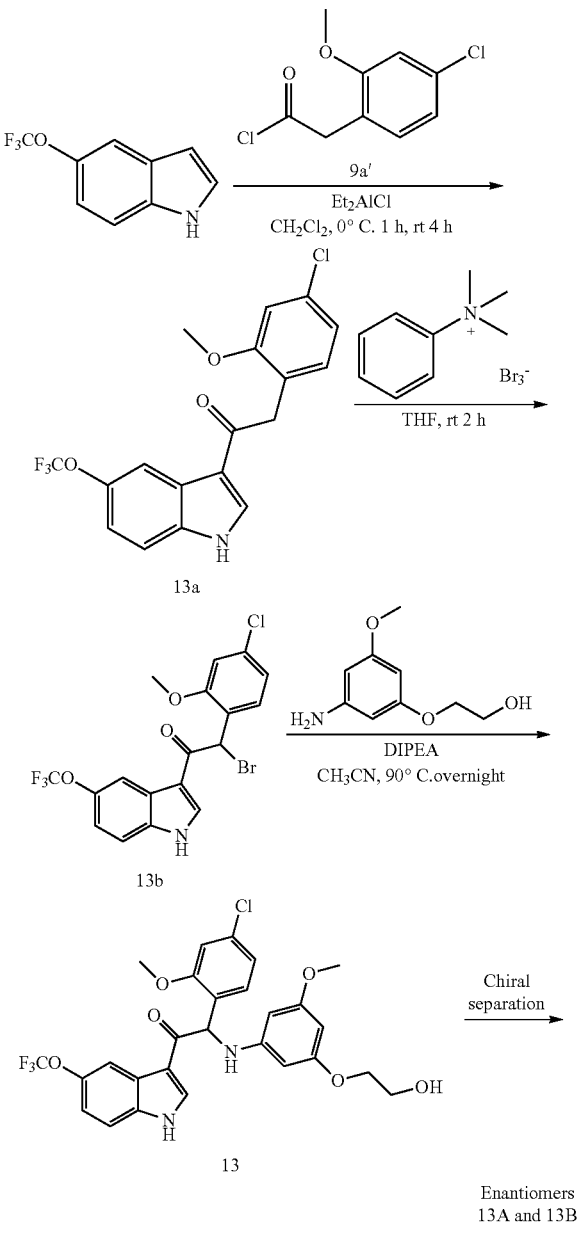

Synthesis of Intermediate 13a:

A solution of 5-(trifluoromethoxy)-1H-indole [CAS 262593-63-5] (3 g, 14.9 mmol) in CH$_2$Cl$_2$ (150 mL) was cooled to 0° C. under N₂-atmosphere. A solution of diethylaluminum chloride 1M in hexane (22.4 mL, 22.4 mmol) was added dropwise and the resulting mixture was kept at 0° C. for 15 min. A solution of 2-(4-chloro-2-methoxyphenyl)acetyl chloride 9a' (4.57 g, 20.9 mmol) in CH$_2$Cl$_2$ (100 mL) was added dropwise. Stirring was continued at 0° C. for 1 h and the reaction mixture was subsequently stirred at room temperature for 4 h. The reaction mixture was poured out in a stirring ice/Rochelle salt solution. After the ice had melted, the mixture was filtered over Dicalite® and the filter cake was washed several times with THF. The filtrates were combined. The layers were separated and the organic layer washed with brine, dried over MgSO$_4$, filtered and evaporated under reduced pressure. The residue was triturated with CH$_2$Cl$_2$ (50 mL) and the resulting precipitate was filtered off and dried under vacuum at 50° C. to provide 2-(4-chloro-2-methoxyphenyl)-1-(5-(trifluoromethoxy)-1H-indol-3-yl)ethanone 13a (4.39 g).

Synthesis of Intermediate 13b:

A stirred solution of 2-(4-chloro-2-methoxyphenyl)-1-(5-(trifluoromethoxy)-1H-indol-3-yl)ethanone 13a (4.39 g, 11.4 mmol) in THF (200 mL) was cooled to 0° C. A solution of phenyltrimethylammonium tribromide [CAS 4207-56-1] (4.73 g, 12.6 mmol) in THF (100 mL) was added dropwise. The resulting suspension was stirred at room temperature for 2 h. The solids were removed by filtration and washed with THF. The combined filtrates were evaporated under reduced pressure. The residue was mixed with EtOAc (30 mL). The solids were isolated by filtration, washed with a small amount of EtOAc and dried under vacuum at 50° C. to provide 2-bromo-2-(4-chloro-2-methoxyphenyl)-1-(5-(trifluoromethoxy)-1H-indol-3-yl)ethanone 13b (5.0 g) as a white solid, which was used without further purification in the next step.

Synthesis of Compound 13 and Chiral Separation of Enantiomers 13A and 13B:

A mixture of 2-bromo-2-(4-chloro-2-methoxyphenyl)-1-(5-(trifluoromethoxy)-1H-indol-3-yl)ethanone 13b (2.3 g, 4.97 mmol), 2-(3-amino-5-methoxyphenoxy)ethanol [CAS 725237-16-1] (1.37 g, 7.46 mmol) and diisopropylethylamine (857 μL, 4.97 mmol) in CH$_3$CN (550 mL) was stirred at 90° C. overnight. The reaction mixture was concentrated under reduced pressure. The residue was dissolved in CH$_2$Cl$_2$ (100 mL), washed with 1N HCl (100 mL) and water (100 mL), dried over MgSO$_4$, filtered and evaporated under reduced pressure. The residue was purified by column chromatography (Stationary phase: Grace Reveleris® silica 120 g, Mobile phase: EtOAc:EtOH(3:1)/heptane gradient 0/100 to 50/50). The desired fractions were combined and evaporated under reduced pressure. The residue was further purified via preparative HPLC (Stationary phase: Uptisphere® C18 ODB~10 μm, 200 g, 5 cm, Mobile phase: 0.25% NH$_4$HCO$_3$ solution in water, CH$_3$CN). The desired fractions were combined and evaporated under reduced pressure to give 2-(4-chloro-2-methoxyphenyl)-2-((3-(2-hydroxyethoxy)-5-methoxyphenyl)amino)-1-(5-(trifluoromethoxy)-1H-indol-3-yl)ethanone (Compound 13, 1.46 g) as a racemic mixture.

The chiral separation of the enantiomers of Compound 13 (1.46 g) was performed via Normal Phase Chiral separation (Stationary phase: AS 20 μm, Mobile phase: 100% methanol). The product fractions were combined and evaporated to provide Enantiomer 13A as the first eluted product and Enantiomer 13B as the second eluted product.

Enantiomer 13A (0.43 g) was purified by flash chromatography (Stationary phase: Grace Reveleris® silica 12 g, Mobile phase: heptane/EtOAc/EtOH gradient 100/0/0 to 40/45/15). The desired fractions were combined, evaporated under reduced pressure and co-evaporated with MeOH and then with MeOH/H$_2$O 3/1. The residue was stirred up in H$_2$O (4 mL) at 45° C., MeOH (125 μL) was added dropwise, and after stirring for 5 min, the solids were filtered off, washed (4×) with a mixture of H$_2$O/MeOH (4/1), and dried under vacuum at 45° C. to provide Enantiomer 13A (389 mg).

Enantiomer 13B (0.45 g) was purified by flash chromatography (Stationary phase Grace Reveleris® silica 12 g, Mobile phase: heptane/EtOAc/EtOH gradient 100/0/0 to 40/45/15). The desired fractions were combined and evaporated under reduced pressure and co-evaporated with MeOH and then with MeOH/H$_2$O (1/4). The residue was stirred up in H$_2$O (4 mL) at 45° C. MeOH (125 μL) was added dropwise and after stirring for 5 min, the solids were filtered off, washed (4×) with a mixture of H$_2$O/MeOH 4/1, and dried under vacuum at 45° C. to provide Enantiomer 13B (423 mg).

Compound 13:

$^1$H NMR (400 MHz, DMSO-d$_6$) δ ppm 3.61 (s, 3H) 3.65 (t, J=5.1 Hz, 2H) 3.75-3.90 (m, 2H) 3.96 (s, 3H) 4.77 (br s, 1H) 5.73 (t, J=2.0 Hz, 1H) 5.94 (d, J=2.0 Hz, 2H) 6.17 (d, J=8.1 Hz, 1H) 6.41 (d, J=8.1 Hz, 1H) 6.97 (dd, J=8.1, 2.0 Hz, 1H) 7.10 (d, J=2.0 Hz, 1H) 7.21 (dd, J=8.8, 2.2 Hz, 1H) 7.37 (d, J=8.1 Hz, 1H) 7.59 (d, J=8.8 Hz, 1H) 8.06 (br s, 1H) 8.54 (s, 1H) 12.26 (br s, 1H)

LC/MS (method LC-B): R$_t$ 2.14 min, MH$^+$ 565

Enantiomer 13A:

$^1$H NMR (400 MHz, DMSO-d$_6$) δ ppm 3.61 (s, 3H) 3.64 (q, J=5.3 Hz, 2H) 3.75-3.89 (m, 2H) 3.95 (s, 3H) 4.77 (t, J=5.6 Hz, 1H) 5.72 (t, J=2.1 Hz, 1H) 5.93 (d, J=2.2 Hz, 2H) 6.16 (d, J=8.1 Hz, 1H) 6.40 (d, J=7.9 Hz, 1H) 6.97 (dd, J=8.1, 2.0 Hz, 1H) 7.09 (d, J=2.0 Hz, 1H) 7.21 (dd, J=8.7, 2.1 Hz, 1H) 7.36 (d, J=8.1 Hz, 1H) 7.58 (d, J=9.0 Hz, 1H) 8.05 (br s, 1H) 8.54 (s, 1H) 12.27 (br s, 1H)

LC/MS (method LC-A): R$_t$ 1.17 min, MH$^+$ 565

$[α]_D^{20}$: +108.5° (c 0.52, DMF)

Chiral SFC (method SFC-D): R$_t$ 3.11 min, MH$^+$ 565, chiral purity 100%.

Enantiomer 13B:

$^1$H NMR (400 MHz, DMSO-d$_6$) δ ppm 3.61 (s, 3H) 3.64 (q, J=5.2 Hz, 2H) 3.76-3.90 (m, 2H) 3.95 (s, 3H) 4.77 (t, J=5.6 Hz, 1H) 5.73 (t, J=2.1 Hz, 1H) 5.93 (d, J=2.0 Hz, 2H) 6.17 (d, J=8.1 Hz, 1H) 6.41 (d, J=8.1 Hz, 1H) 6.98 (dd, J=8.1, 2.0 Hz, 1H) 7.10 (d, J=2.2 Hz, 1H) 7.21 (dd, J=8.8, 1.8 Hz, 1H) 7.37 (d, J=8.4 Hz, 1H) 7.59 (d, J=9.0 Hz, 1H) 8.06 (br s, 1H) 8.54 (s, 1H) 12.28 (br s, 1H)

LC/MS (method LC-A): R$_t$ 1.17 min, MH$^+$ 565

$[α]_D^{20}$: -107.4° (c 0.485, DMF)

Chiral SFC (method SFC-D): R$_t$ 3.50 min, MH$^+$ 565, chiral purity 100%.

Example 14: 2-(4-chloro-2-methoxyphenyl)-2-((3-(2-hydroxyethoxy)-5-methoxyphenyl)amino)-1-(6-methoxy-5-(trifluoromethoxy)-1H-indol-3-yl)ethanone (Compound 14) and Chiral Separation into Enantiomers 14A and 14B

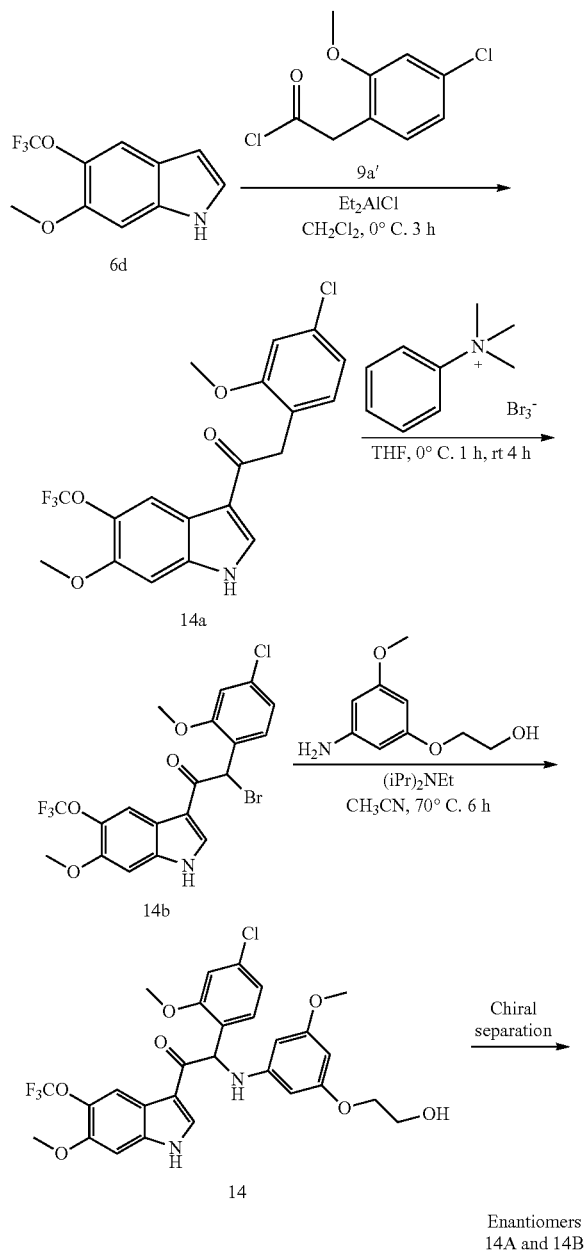

Synthesis of Intermediate 14a:
Under N$_2$-flow, diethylaluminum chloride 1M in hexane (9.73 mL, 9.73 mmol) was added dropwise at 0° C. to a solution of 6-methoxy-5-(trifluoromethoxy)-1H-indole 6d (1.5 g, 6.49 mmol) in CH$_2$Cl$_2$ (35 mL). After stirring for 30 min at 0° C., 2-(4-chloro-2-methoxyphenyl)acetyl chloride 9a' (2.1 g, 9.73 mmol) in CH$_2$Cl$_2$ (15 mL) was added dropwise. The mixture was stirred at 0° C. for 3 h. Ice-water was added. The precipitate was filtered off, washed with water and dried under vacuum to give 2-(4-chloro-2-methoxyphenyl)-1-(6-methoxy-5-(trifluoromethoxy)-1H-indol-3-yl)ethanone 14a (1.9 g).

Synthesis of Intermediate 14b:
At 0° C., a solution of phenyltrimethylammonium tribromide [CAS 4207-56-1] (1.9 g, 4.59 mmol) in THF (60 mL) was added dropwise to a mixture of 2-(4-chloro-2-methoxyphenyl)-1-(6-methoxy-5-(trifluoromethoxy)-1H-indol-3-yl)ethanone 14a (1.73 g, 4.59 mmol) in THF (60 mL). The mixture was stirred at 0° C. for 1 h and at room temperature for 4 h. The precipitate was filtered off and washed with EtOAc.

The filtrate was concentrated under reduced pressure. The residue was dissolved in EtOAc. The organic layer was washed with water, dried over MgSO$_4$, filtered, and the solvent was evaporated under reduced pressure. The residue was taken up with diisopropyl ether. The precipitate was filtered off and dried to give 2-bromo-2-(4-chloro-2-methoxyphenyl)-1-(6-methoxy-5-(trifluoromethoxy)-1H-indol-3-yl)ethanone 14b (2.1 g).

Synthesis of Compound 14 and Chiral Separation into Enantiomers 14A and 14B:
A mixture of 2-bromo-2-(4-chloro-2-methoxyphenyl)-1-(6-methoxy-5-(trifluoromethoxy)-1H-indol-3-yl)ethanone 14b (2.1 g, 4.26 mmol), 2-(3-amino-5-methoxyphenoxy)ethanol [CAS 725237-16-1] (0.937 g, 5.11 mmol) and diisopropylethylamine (1.1 mL, 6.4 mmol) in CH$_3$CN (100 mL) was stirred at 70° C. for 24 h and then concentrated under reduced pressure. The residue was diluted with CH$_2$Cl$_2$ and washed with 1N HCl. The organic layer was separated, dried over MgSO$_4$, filtered, and the solvent was evaporated under reduced pressure. The residue was purified by column chromatography on silica gel (15-40 μm, 80 g, CH$_2$Cl$_2$/MeOH 99/1). The fractions containing Compound 14 were combined and the solvent was evaporated under reduced pressure. The product (1.9 g) was further purified via achiral SFC (Stationary phase: 2-ethylpyridine 5 μm 150×30 mm, Mobile phase: 70% CO$_2$, 30% MeOH+0.3% iPrNH$_2$) to give, after solidification in diisopropyl ether/petroleum ether, 2-(4-chloro-2-methoxyphenyl)-2-((3-(2-hydroxyethoxy)-5-methoxyphenyl)amino)-1-(6-methoxy-5-(trifluoromethoxy)-1H-indol-3-yl)ethanone (Compound 14, 1.18 g) as a racemic mixture. The enantiomers of Compound 14 were separated via Preparative Chiral SFC (Stationary phase: Chiralpack® IC 5 μm 250×20 mm, Mobile phase: 70% CO$_2$, 30% iPrOH+0.3% iPrNH$_2$) to give, after solidification in heptane/diisopropyl ether/ether, 420 mg of the first eluted Enantiomer 14A and 408 mg of the second eluted Enantiomer 14B.

Compound 14:
$^1$H NMR (400 MHz, DMSO-d$_6$) δ ppm 3.59-3.68 (m, 5H) 3.77-3.89 (m, 5H) 3.95 (s, 3H) 4.75 (br t, J=5.1 Hz, 1H) 5.72 (br s, 1H) 5.92 (d, J=1.5 Hz, 2H) 6.13 (d, J=8.1 Hz, 1H) 6.37 (d, J=8.1 Hz, 1H) 6.97 (dd, J=8.3, 1.8 Hz, 1H) 7.09 (d, J=1.5 Hz, 1H) 7.21 (s, 1H) 7.36 (d, J=8.6 Hz, 1H) 8.01 (s, 1H) 8.39 (s, 1H) 11.99 (br s, 1H)
LC/MS (method LC-C): R$_t$ 3.14 min, MH$^+$ 595

Enantiomer 14A:
$^1$H NMR (500 MHz, DMSO-d$_6$) δ ppm 3.56-3.68 (m, 5H) 3.76-3.90 (m, 5H) 3.96 (s, 3H) 4.78 (t, J=5.5 Hz, 1H) 5.72 (t, J=2.1 Hz, 1H) 5.92 (d, J=1.9 Hz, 2H) 6.14 (d, J=8.2 Hz, 1H) 6.40 (d, J=7.9 Hz, 1H) 6.97 (dd, J=8.2, 1.9 Hz, 1H) 7.10 (d, J=1.9 Hz, 1H) 7.21 (s, 1H) 7.36 (d, J=8.2 Hz, 1H) 8.02 (d, J=1.3 Hz, 1H) 8.40 (s, 1H) 12.05 (br s, 1H)
LC/MS (method LC-C): R$_t$ 3.13 min, MH$^+$ 595
[α]$_D^{20}$: +81.7° (c 0.235, DMF)
Chiral SFC (method SFC-C): R$_t$ 1.58 min, MH$^+$ 595, chiral purity 100%.

Enantiomer 14B:
$^1$H NMR (500 MHz, DMSO-$d_6$) δ ppm 3.58-3.69 (m, 5H) 3.77-3.91 (m, 5H) 3.96 (s, 3H) 4.78 (t, J=5.5 Hz, 1H) 5.72 (t, J=2.1 Hz, 1H) 5.92 (d, J=1.9 Hz, 2H) 6.14 (d, J=8.2 Hz, 1H) 6.40 (d, J=7.9 Hz, 1H) 6.97 (dd, J=8.2, 1.9 Hz, 1H) 7.10 (d, J=1.9 Hz, 1H) 7.21 (s, 1H) 7.36 (d, J=8.2 Hz, 1H) 8.02 (d, J=1.3 Hz, 1H) 8.40 (s, 1H) 12.04 (br s, 1H)
LC/MS (method LC-C): $R_t$ 3.13 min, MH$^+$ 595
$[α]_D^{20}$: −82.5° (c 0.2267, DMF)
Chiral SFC (method SFC-C): $R_t$ 2.23 min, MH$^+$ 595, chiral purity 99.29%.

Example 15: synthesis 2-(4-chloro-2-methoxyphenyl)-1-(6-fluoro-5-(trifluoromethoxy)-1H-indol-3-yl)-2-((3-(2-hydroxyethoxy)-5-methoxyphenyl)amino)ethanone (Compound 15) and Chiral Separation into Enantiomers 15A and 15B

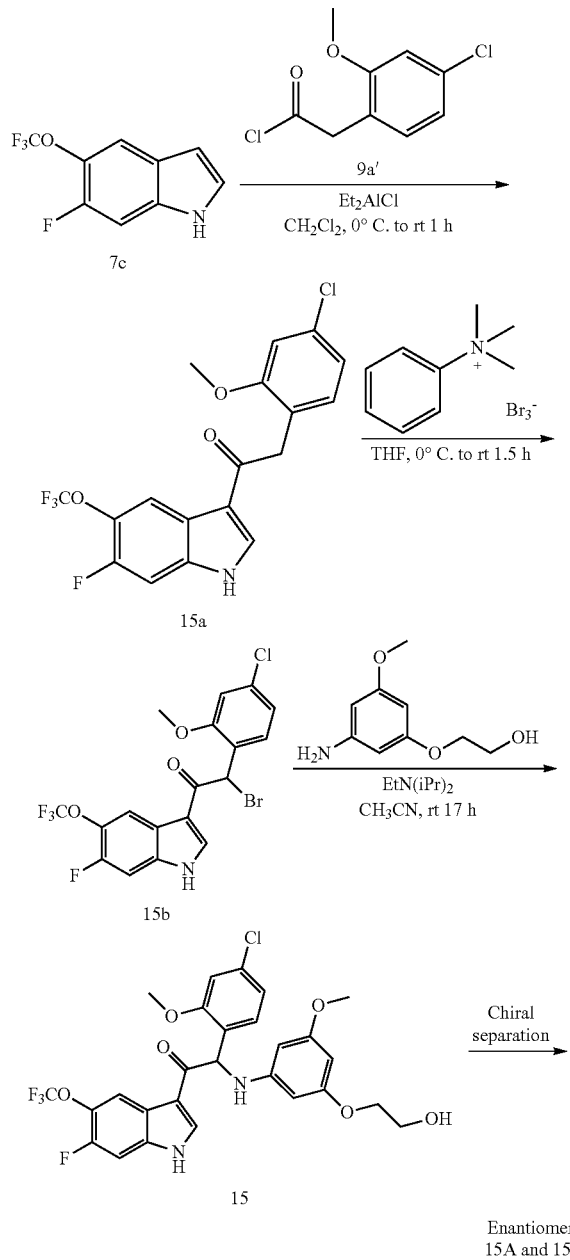

Synthesis of Intermediate 15a:
A mechanically stirred solution of 6-fluoro-5-(trifluoromethoxy)-1H-indole 7c (2.92 g, 13.3 mmol) in CH$_2$Cl$_2$ (150 mL) was cooled to 0° C. under N$_2$-atmosphere. A solution of diethylaluminum chloride 1M in hexane (20.0 mL, 20.0 mmol) was added dropwise and the resulting mixture was kept at 0° C. for 5 min. A solution of 2-(4-chloro-2-methoxyphenyl)acetyl chloride 9a' (4.37 g, 19.9 mmol) in CH$_2$Cl$_2$ (75 mL) was added dropwise while keeping the reaction temperature below 5° C. Stirring was continued at 0° C. for 1 h and the reaction mixture was subsequently stirred at room temperature for 1 h. The reaction mixture was cooled to 0° C. and a solution of Rochelle salt [CAS 6100-16-9] (7.53 g, 26.7 mmol) in water (8 mL) was added dropwise. The reaction mixture was stirred at 0° C. for 30 min and then allowed to reach room temperature. THF (200 mL) and Na$_2$SO$_4$ (25 g) were added. After overnight stirring, the reaction mixture was filtered over Dicalite® and the filter cake was washed with THF (4×100 mL). The combined filtrates were evaporated under reduced pressure. The residue was purified by flash chromatography (Stationary phase: Biotage® SNAP Ultra silica 100 g, Mobile phase: heptane/EtOAc/EtOH gradient 100/0/0 to 40/45/15). The fractions containing product were combined and evaporated under reduced pressure to provide 2-(4-chloro-2-methoxyphenyl)-1-(6-fluoro-5-(trifluoromethoxy)-1H-indol-3-yl)ethanone 15a (2.7 g).

Synthesis of Intermediate 15b:
A stirred solution of 2-(4-chloro-2-methoxyphenyl)-1-(6-fluoro-5-(trifluoromethoxy)-1H-indol-3-yl)ethanone 15a (1.37 g, 3.24 mmol) in THF (20 mL) was cooled to 0° C. under N$_2$-atmosphere. Phenyltrimethylammonium tribromide [CAS 4207-56-1] (1.28 g, 3.4 mmol) was added in one portion. The reaction mixture was stirred at 0° C. for 40 min and subsequently at room temperature for 1.5 h. The solids were removed by filtration and washed with THF (2×). The combined filtrates were evaporated under reduced pressure to provide 2-bromo-2-(4-chloro-2-methoxyphenyl)-1-(6-fluoro-5-(trifluoromethoxy)-1H-indol-3-yl)ethanone 15b (1.77 g), which was used without further purification in the next step.

Synthesis of Compound 15 and Chiral Separation of Enantiomers 15A and 15B:
A mixture 2-bromo-2-(4-chloro-2-methoxyphenyl)-1-(7-methyl-5-(trifluoromethoxy)-1H-indol-3-yl)ethanone 15b (1.77 g, 3.43 mmol), 2-(3-amino-5-methoxyphenoxy)ethanol [CAS 725237-16-1] (1.26 g, 6.86 mmol) and diisopropylethylamine (1.18 mL, 6.86 mmol) in CH$_3$CN (30 mL) was stirred at room temperature for 17 h. Water (125 mL) was added and the product was extracted with Et20 (2×). The combined organic layers were washed with brine, dried over MgSO$_4$, filtered, and evaporated under reduced pressure. The residue was purified by flash chromatography (Stationary phase: Biotage® SNAP Ultra silica 25 g, Mobile phase: heptane/EtOAc/EtOH gradient 100/0/0 to 40/45/15). The desired fractions were combined and evaporated under reduced pressure. The residue was further purified via preparative HPLC (Stationary phase: RP XBridge® Prep C18 OBD—10 μm, 30×150 mm, Mobile phase: 0.25% NH$_4$HCO$_3$ solution in water, CH$_3$CN). The product fractions were combined and evaporated under reduced pressure to provide racemic 2-(4-chloro-2-methoxyphenyl)-1-(6-fluoro-5-(trifluoromethoxy)-1H-indol-3-yl)-2-((3-(2-hydroxyethoxy)-5-methoxyphenyl)amino)ethanone (Compound 15, 589 mg).

The chiral separation of the enantiomers of Compound 15 (589 mg) was performed via preparative SFC (Stationary phase: Chiralcel® Diacel OD 20×250 mm, Mobile phase: CO$_2$, EtOH+0.4% iPrNH$_2$) to provide Enantiomer 15A as the first eluted enantiomer and Enantiomer 15B as the second eluted enantiomer. Both enantiomers were solidified by precipitation from a solvent mixture of MeOH and water. The solids were filtered off and dried under vacuum at 50° C. to provide Enantiomer 15A (101 mg) and Enantiomer 15B (73 mg).

Enantiomer 15A:
$^1$H NMR (360 MHz, DMSO-$d_6$) δ ppm 3.61 (s, 3H) 3.64 (q, J=5.4 Hz, 2H) 3.75-3.89 (m, 2H) 3.94 (s, 3H) 4.80 (t, J=5.5 Hz, 1H) 5.72 (t, J=2.0 Hz, 1H) 5.92 (d, J=2.2 Hz, 2H) 6.16 (d, J=8.1 Hz, 1H) 6.44 (d, J=8.1 Hz, 1H) 6.98 (dd, J=8.2, 2.0 Hz, 1H) 7.10 (d, J=1.8 Hz, 1H) 7.36 (d, J=8.4 Hz, 1H) 7.61 (d, J=10.6 Hz, 1H) 8.16 (dd, J=7.7, 1.1 Hz, 1H) 8.55 (s, 1H) 12.33 (br s, 1H)

LC/MS (method LC-A): $R_t$ 1.20 min, MH$^+$ 583

$[\alpha]_D^{20}$: −69.9° (c 0.261, DMF)

Chiral SFC (method SFC-D): $R_t$ 3.30 min, MH$^+$ 583, chiral purity 98.7%.

Melting point: 106° C.

Enantiomer 15B:
$^1$H NMR (360 MHz, DMSO-$d_6$) δ ppm 3.61 (s, 3H) 3.62-3.67 (m, 2H) 3.74-3.89 (m, 2H) 3.94 (s, 3H) 4.80 (t, J=5.5 Hz, 1H) 5.72 (t, J=2.0 Hz, 1H) 5.92 (d, J=1.8 Hz, 2H) 6.16 (d, J=8.4 Hz, 1H) 6.44 (d, J=8.1 Hz, 1H) 6.98 (dd, J=8.4, 1.8 Hz, 1H) 7.10 (d, J=1.8 Hz, 1H) 7.36 (d, J=8.4 Hz, 1H) 7.60 (d, J=10.6 Hz, 1H) 8.16 (dd, J=7.5, 0.9 Hz, 1H) 8.54 (s, 1H) 12.33 (br s, 1H)

LC/MS (method LC-A): $R_t$ 1.20 min, MH$^+$ 583

$[\alpha]_D^{20}$: +91.8° (c 0.282, DMF)

Chiral SFC (method SFC-D): $R_t$ 2.93 min, MH$^+$ 583, chiral purity 100%.

Melting point: 107° C.

Example 16: synthesis 2-(4-chloro-2-methoxyphenyl)-2-((3-(2-hydroxyethoxy)-5-methoxyphenyl)amino)-1-(7-methyl-5-(trifluoromethoxy)-1H-indol-3-yl)ethanone (Compound 16) and Chiral Separation into Enantiomers 16A and 16B

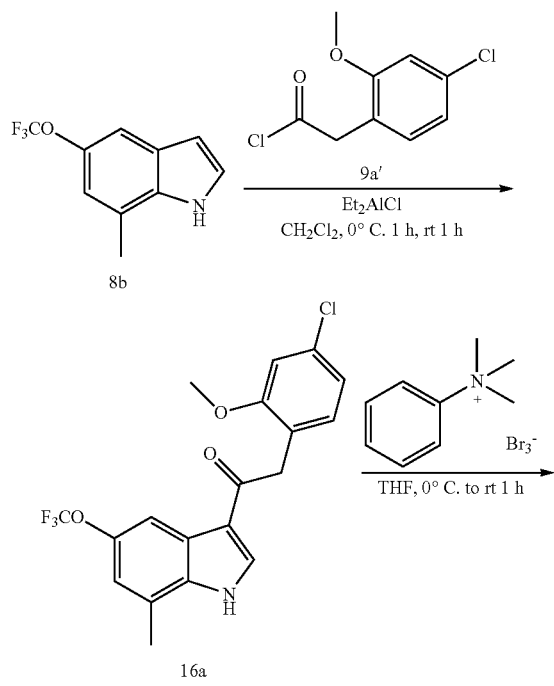

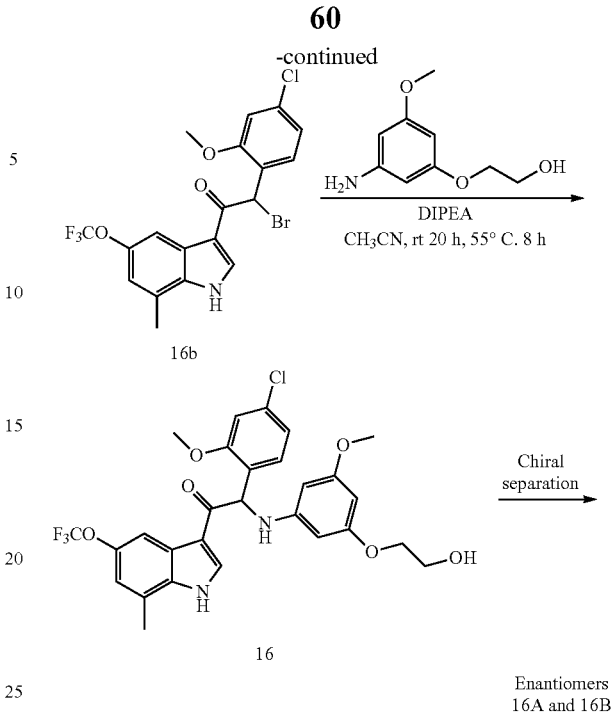

Synthesis of Intermediate 16a:
A mechanically stirred solution of 7-methyl-5-(trifluoromethoxy)-1H-indole 8b (1.5 g, 6.97 mmol) in CH$_2$Cl$_2$ (100 mL) was cooled to 0° C. under N$_2$-atmosphere. A solution of diethylaluminum chloride 1M in hexane (10.5 mL, 10.5 mmol) was added dropwise and the resulting mixture was kept at 0° C. for 25 min. A solution of 2-(4-chloro-2-methoxyphenyl)acetyl chloride 9a' (2.29 g, 10.5 mmol) in CH$_2$Cl$_2$ (40 mL) was added dropwise while keeping the reaction temperature below 6° C. Stirring was continued at 0° C. for 1 h and the reaction mixture was subsequently stirred at room temperature for 1 h. The reaction mixture was cooled to 0° C. and a solution of Rochelle salt [CAS 6100-16-9] (3.94 g, 13.9 mmol) in water (4 mL) was added dropwise. After addition, the mixture was stirred at 0° C. for 20 min, and at room temperature for 1 h. THF (125 mL) and Na$_2$SO$_4$ (15 g) were added. After stirring for 1 hour, the reaction mixture was filtered over Dicalite® and the filter cake was washed with THF (5×100 mL). The combined filtrates were evaporated under reduced pressure. The residue solidified upon standing overnight. The solids were stirred up in CH$_3$CN (5 mL), filtered off, washed with CH$_3$CN (3×1.5 mL) and dried under vacuum at 50° C. to provide 2-(4-chloro-2-methoxyphenyl)-1-(7-methyl-5-(trifluoromethoxy)-1H-indol-3-yl)ethanone 16a (1.9 g).

Synthesis of Intermediate 16b:
A stirred solution of 2-(4-chloro-2-methoxyphenyl)-1-(7-methyl-5-(trifluoromethoxy)-1H-indol-3-yl)ethanone 16a (1.90 g, 4.78 mmol) in THF (100 mL) was cooled to 0° C. under N$_2$-atmosphere. Phenyltrimethylammonium tribromide [CAS 4207-56-1] (1.89 g, 5.02 mmol) was added in one portion. The reaction mixture was stirred at 0° C. for 1.5 h and subsequently at room temperature for 1 h. The solids were removed by filtration and washed with THF (2×). The combined filtrates were evaporated under reduced pressure to provide 2-bromo-2-(4-chloro-2-methoxyphenyl)-1-(7-methyl-5-(trifluoromethoxy)-1H-indol-3-yl)ethanone 16b (2.28 g), which was used without further purification in the next step.

Synthesis of Compound 16 and Chiral Separation of Enantiomers 16A and 16B:

A mixture 2-bromo-2-(4-chloro-2-methoxyphenyl)-1-(7-methyl-5-(trifluoromethoxy)-1H-indol-3-yl)ethanone 16b (2.28 g, 4.78 mmol), 2-(3-amino-5-methoxyphenoxy)ethanol [CAS 725237-16-1] (1.75 g, 9.55 mmol) and diisopropylethylamine (1.65 mL, 9.55 mmol) in $CH_3CN$ (100 mL) was stirred at room temperature for 20 h, and subsequently at 55° C. for 8 h. After cooling to room temperature, the reaction mixture was poured out into stirring water (500 mL). The product was extracted with $Et_2O$ (2×). The combined organic layers were washed with brine, dried over $MgSO_4$, filtered, and evaporated under reduced pressure.

The residue was purified by flash chromatography (Stationary phase: Grace Reveleris® silica 80 g, Mobile phase: heptane/EtOAc/EtOH gradient 100/0/0 to 40/45/15). The desired fractions were combined and evaporated under reduced pressure to provide 2-(4-chloro-2-methoxyphenyl)-2-((3-(2-hydroxyethoxy)-5-methoxyphenyl)amino)-1-(7-methyl-5-(trifluoromethoxy)-1H-indol-3-yl)ethanone (Compound 16, 2.1 g) as a racemic mixture. A small fraction of Compound 16 (100 mg) was further purified via Preparative HPLC (Stationary phase: RP XBridge® Prep C18 OBD—10 μm, 30×150 mm, Mobile phase: 0.25% $NH_4HCO_3$ solution in water, $CH_3CN$). The desired fractions were combined, evaporated under reduced pressure, and co-evaporated from a mixture of $CH_3CN$ and MeOH. The residue was solidified by lyophilization from a solution in $CH_3CN$ (1.5 mL) and water (1 mL) to provide an analytical sample of racemic Compound 16 (51 mg).

The chiral separation of the enantiomers of Compound 16 (2.00 g) was performed via Normal Phase Chiral separation (Stationary phase: AS 20 μm, Mobile phase: 100% methanol) to provide Enantiomer 16A as the first eluted enantiomer and Enantiomer 16B as the second eluted enantiomer. Both enantiomers were re-purified by Reverse phase HPLC (Stationary phase: Kromasil® C18 100A 5 μm (Eka Nobel), Mobile phase: 0.25% $NH_4HCO_3$ in water/$CH_3CN$ gradient 50/50 to 0/100). The desired fractions were combined and evaporated under reduced pressure. Enantiomer 16A was precipitated from a mixture of MeOH (7 mL) and $H_2O$ (1.8 mL). The solids were filtered off, washed with a mixture of MeOH/water (1/1) (3×1 mL), and dried under vacuum at 45° C. to provide Enantiomer 16A (517 mg). Enantiomer 16B was precipitated from a mixture of MeOH (7 mL) and $H_2O$ (3 mL). The solids were filtered off, washed with a mixture of MeOH/water (1/1) (3×1 mL), and dried under vacuum at 45° C. to provide Enantiomer 16B (441 mg).

Compound 16:
$^1$H NMR (400 MHz, DMSO-$d_6$) δ ppm 2.50 (s, 3H) 3.61 (s, 3H) 3.64 (q, J=5.4 Hz, 2H) 3.76-3.90 (m, 2H) 3.96 (s, 3H) 4.78 (t, J=5.6 Hz, 1H) 5.72 (t, J=2.1 Hz, 1H) 5.94 (d, J=2.2 Hz, 2H) 6.18 (d, J=8.1 Hz, 1H) 6.40 (d, J=8.1 Hz, 1H) 6.97 (dd, J=8.4, 2.0 Hz, 1H) 7.02-7.06 (m, 1H) 7.10 (d, J=2.0 Hz, 1H) 7.36 (d, J=8.4 Hz, 1H) 7.89 (br s, 1H) 8.52 (s, 1H) 12.36 (br s, 1H)

LC/MS (method LC-B): $R_t$ 2.20 min, $MH^+$ 579

Enantiomer 16A:
$^1$H NMR (400 MHz, DMSO-$d_6$) δ ppm 2.51 (s, 3H) 3.61 (s, 3H) 3.64 (q, J=5.4 Hz, 2H) 3.78-3.89 (m, 2H) 3.96 (s, 3H) 4.77 (t, J=5.5 Hz, 1H) 5.72 (t, J=2.1 Hz, 1H) 5.94 (d, J=2.2 Hz, 2H) 6.18 (d, J=8.1 Hz, 1H) 6.38 (d, J=7.9 Hz, 1H) 6.97 (dd, J=8.4, 2.0 Hz, 1H) 7.04 (br s, 1H) 7.10 (d, J=2.0 Hz, 1H) 7.36 (d, J=8.4 Hz, 1H) 7.89 (br s, 1H) 8.51 (d, J=3.5 Hz, 1H) 12.35 (d, J=2.9 Hz, 1H)

LC/MS (method LC-A): $R_t$ 1.21 min, $MH^+$ 579
$[α]_D^{20}$: +82.4° (c 0.495, DMF)
Chiral SFC (method SFC-D): $R_t$ 2.97 min, $MH^+$ 579, chiral purity 100%.
Melting point: 106° C.

Enantiomer 16B:
$^1$H NMR (400 MHz, DMSO-$d_6$) δ ppm 2.51 (s, 3H) 3.61 (s, 3H) 3.64 (q, J=5.4 Hz, 2H) 3.75-3.90 (m, 2H) 3.96 (s, 3H) 4.77 (t, J=5.5 Hz, 1H) 5.72 (t, J=2.0 Hz, 1H) 5.94 (d, J=2.0 Hz, 2H) 6.18 (d, J=7.9 Hz, 1H) 6.39 (d, J=7.9 Hz, 1H) 6.97 (dd, J=8.4, 2.0 Hz, 1H) 7.05 (br s, 1H) 7.10 (d, J=2.0 Hz, 1H) 7.36 (d, J=8.1 Hz, 1H) 7.89 (br s, 1H) 8.52 (d, J=3.3 Hz, 1H) 12.36 (d, J=3.1 Hz, 1H)

LC/MS (method LC-A): $R_t$ 1.21 min, $MH^+$ 579
$[α]_D^{20}$: −82.0° (c 0.45, DMF)
Chiral SFC (method SFC-D): $R_t$ 3.36 min, $MH^+$ 579, chiral purity 100%.
Melting point: 105° C.

TABLE

| compounds prepared as described above | | |
|---|---|---|
| Compound | Structure | Optical rotation |
| 1 | (structure) | racemic |

TABLE-continued compounds prepared as described above

| Compound | Structure | Optical rotation |
|---|---|---|
| 1A | 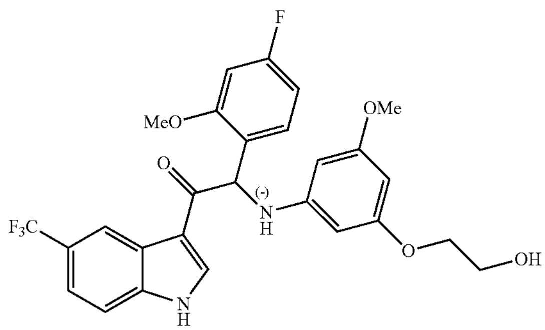 | $[\alpha]_D^{20} = -93.7°$ |
| 1B | 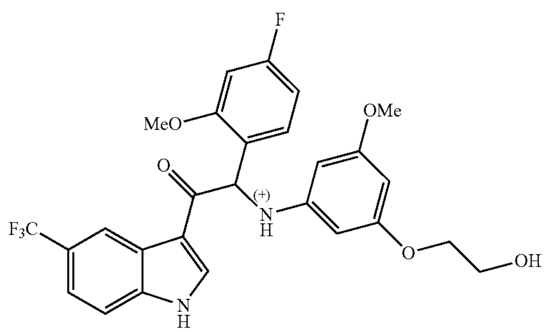 | $[\alpha]_D^{20} = +89.5°$ |
| 2 | 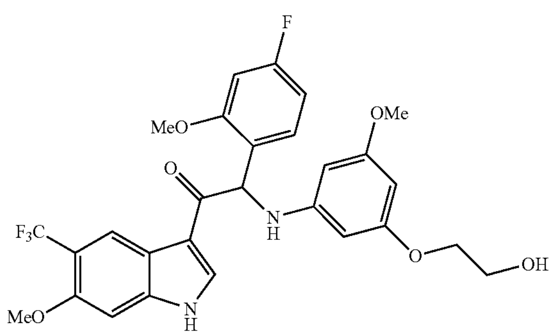 | racemic |
| 2A | 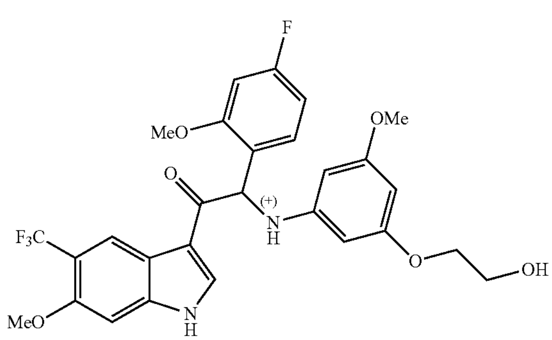 | $[\alpha]_D^{20} = +92.3°$ |

TABLE-continued compounds prepared as described above

| Compound | Structure | Optical rotation |
| --- | --- | --- |
| 2B | 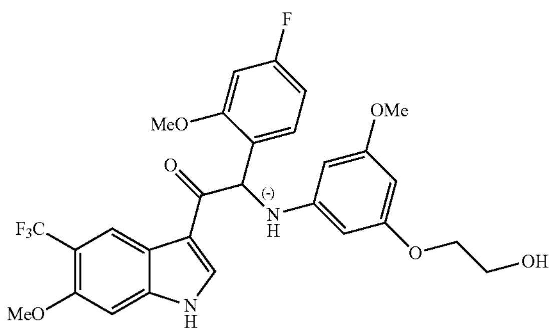 [SMILES: COc1cc(NC(C(=O)c2c[nH]c3cc(OC)c(C(F)(F)F)cc23)c2ccc(F)cc2OC)cc(OCCO)c1] | $[\alpha]_D^{20} = -88.4°$ |
| 3 | 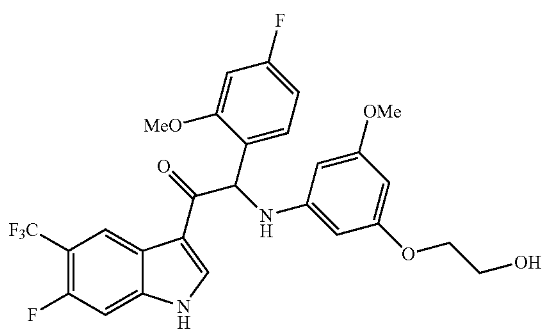 [SMILES: COc1cc(NC(C(=O)c2c[nH]c3cc(F)c(C(F)(F)F)cc23)c2ccc(F)cc2OC)cc(OCCO)c1] | racemic |
| 3A | 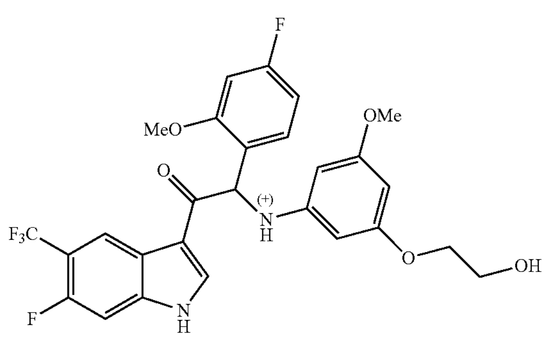 [SMILES: COc1cc(NC(C(=O)c2c[nH]c3cc(F)c(C(F)(F)F)cc23)c2ccc(F)cc2OC)cc(OCCO)c1] | $[\alpha]_D^{20} = +91.0°$ |
| 3B | 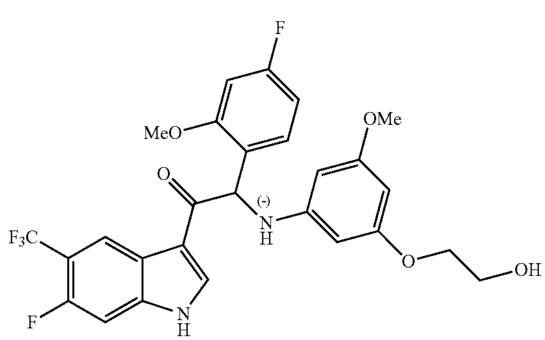 [SMILES: COc1cc(NC(C(=O)c2c[nH]c3cc(F)c(C(F)(F)F)cc23)c2ccc(F)cc2OC)cc(OCCO)c1] | $[\alpha]_D^{20} = -82.7°$ |

TABLE-continued compounds prepared as described above

| Compound | Structure | Optical rotation |
|---|---|---|
| 4 | (structure) | racemic |
| 4A | (structure) | $[\alpha]_D^{20} = -80.4°$ |
| 4B | (structure) | $[\alpha]_D^{20} = +74.1°$ |
| 5 | (structure) | racemic |

TABLE-continued compounds prepared as described above

| Compound | Structure | Optical rotation |
|---|---|---|
| 5A | (structure) | $[\alpha]_D^{20} = -93.5°$ |
| 5B | (structure) | $[\alpha]_D^{20} = +95.1°$ |
| 6 | (structure) | racemic |
| 6A | (structure) | $[\alpha]_D^{20} = +73.9°$ |

TABLE-continued compounds prepared as described above

| Compound | Structure | Optical rotation |
|---|---|---|
| 6B | 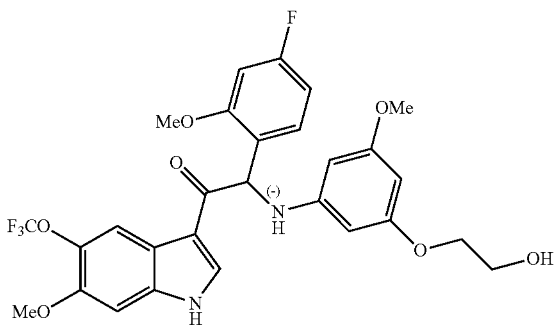 | $[\alpha]_D^{20} = -73.7°$ |
| 7 | 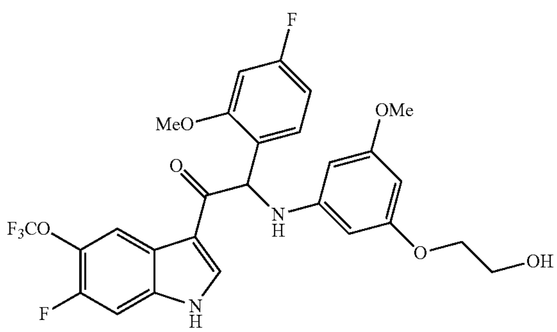 [SMILES: COc1cc(NC(C(=O)c2c[nH]c3cc(F)c(OC(F)(F)F)cc23)c2ccc(F)cc2OC)cc(OCCO)c1] | racemic |
| 7A | 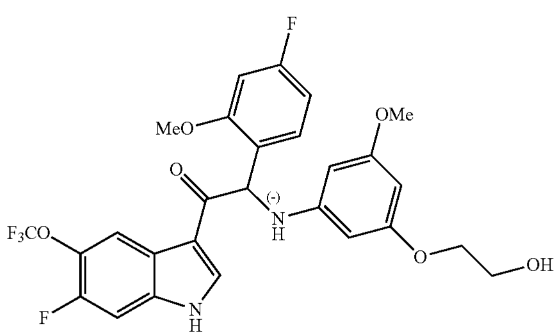 [SMILES: COc1cc(NC(C(=O)c2c[nH]c3cc(F)c(OC(F)(F)F)cc23)c2ccc(F)cc2OC)cc(OCCO)c1] | $[\alpha]_D^{20} = -77.1°$ |
| 7B | 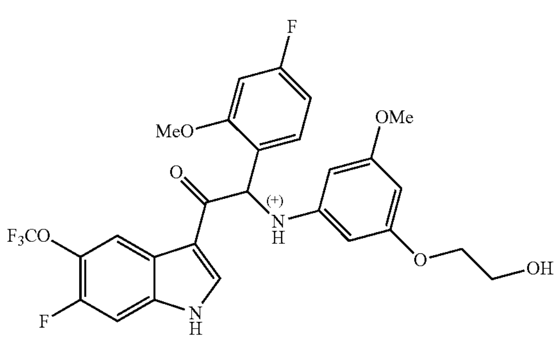 [SMILES: COc1cc(NC(C(=O)c2c[nH]c3cc(F)c(OC(F)(F)F)cc23)c2ccc(F)cc2OC)cc(OCCO)c1] | $[\alpha]_D^{20} = +84.0°$ |

TABLE-continued
compounds prepared as described above
| Compound | Structure | Optical rotation |
|---|---|---|
| 8 | 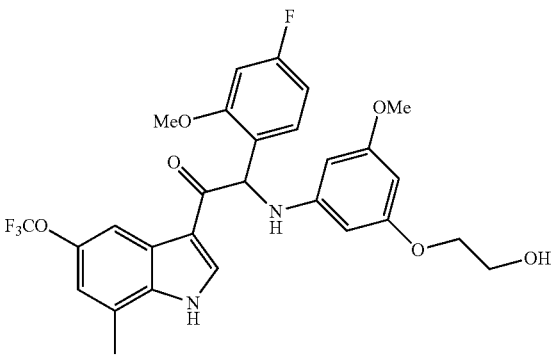 [SMILES: COc1cc(NC(C(=O)c2c[nH]c3c(C)cc(OC(F)(F)F)cc23)c2ccc(F)cc2OC)cc(OCCO)c1] | racemic |
| 8A | 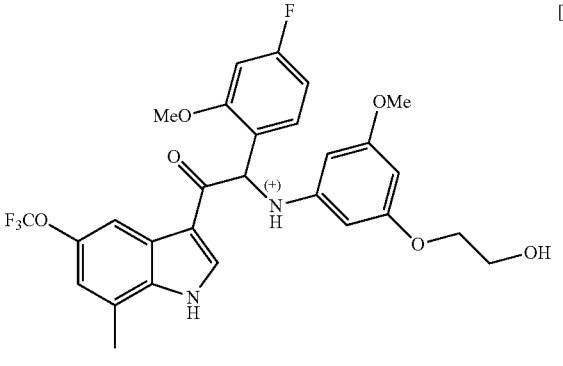 | $[\alpha]_D^{20} = +77.8°$ |
| 8B | 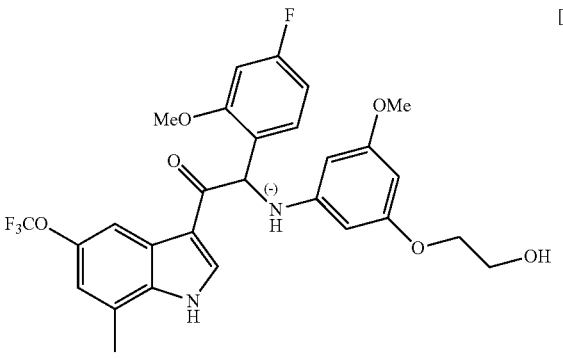 | $[\alpha]_D^{20} = -77.9°$ |
| 9 | 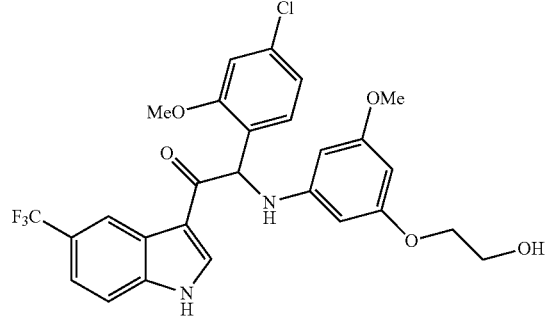 | racemic |

TABLE-continued compounds prepared as described above

| Compound | Structure | Optical rotation |
|---|---|---|
| 9A | 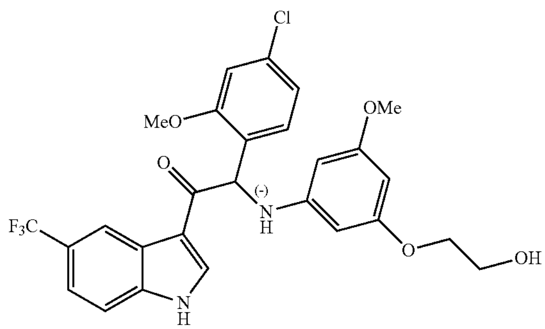 | $[\alpha]_D^{20} = -102.7°$ |
| 9B | 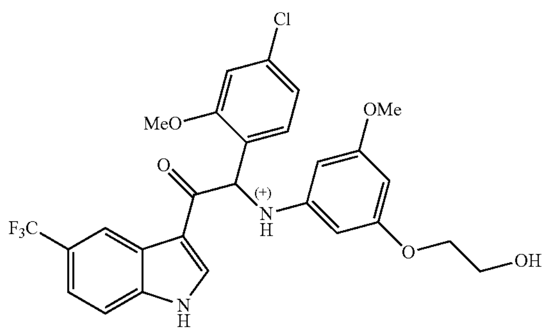 [SMILES: COc1cc(NC(C(=O)c2c[nH]c3ccc(C(F)(F)F)cc23)c2ccc(Cl)cc2OC)cc(OCCO)c1] | $[\alpha]_D^{20} = +124.7°$ |
| 10 | 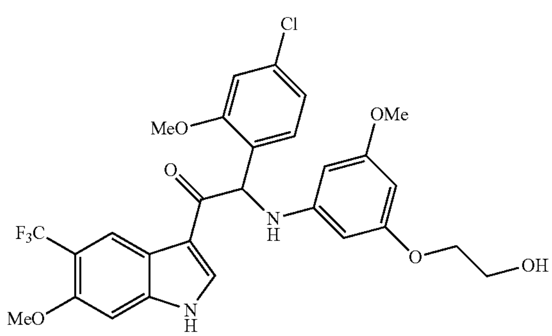 [SMILES: COc1cc(NC(C(=O)c2c[nH]c3cc(OC)c(C(F)(F)F)cc23)c2ccc(Cl)cc2OC)cc(OCCO)c1] | racemic |
| 11 | 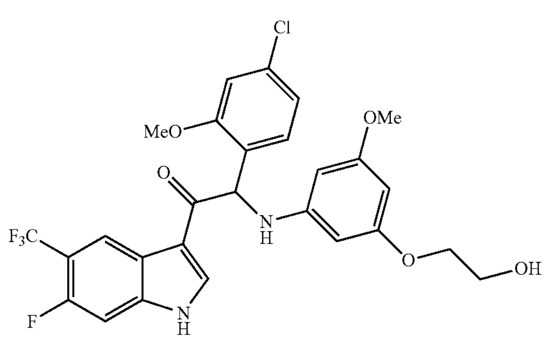 | racemic |

TABLE-continued compounds prepared as described above

| Compound | Structure | Optical rotation |
| --- | --- | --- |
| 11A | 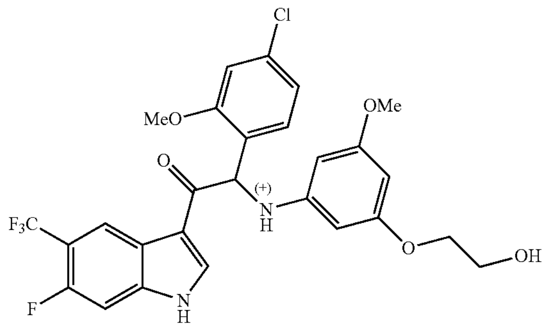 | $[\alpha]_D^{20} = +87.4°$ |
| 11B | 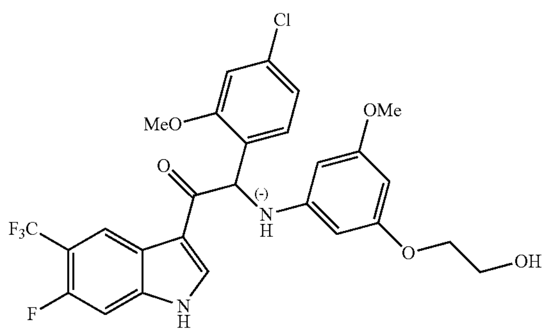 | $[\alpha]_D^{20} = -86.6°$ |
| 12 | 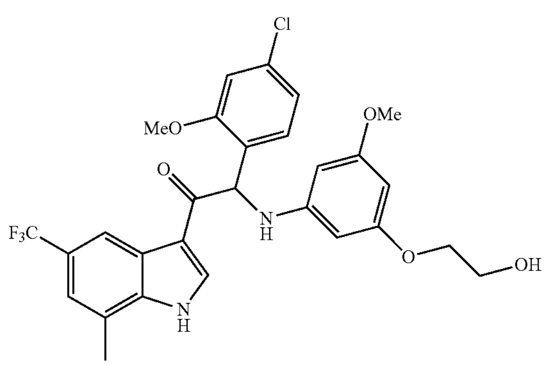 [SMILES: COc1cc(NC(C(=O)c2c[nH]c3c(C)cc(C(F)(F)F)cc23)c2ccc(Cl)cc2OC)cc(OCCO)c1] | racemic |
| 12A | 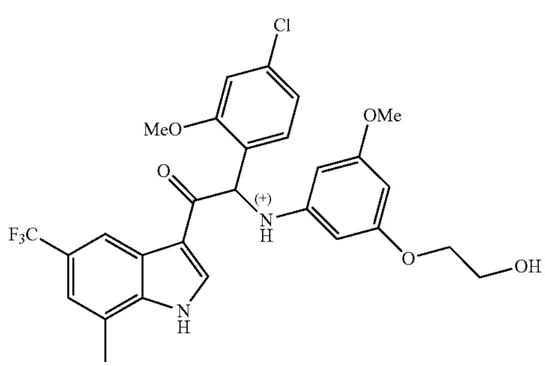 [SMILES: COc1cc(NC(C(=O)c2c[nH]c3c(C)cc(C(F)(F)F)cc23)c2ccc(Cl)cc2OC)cc(OCCO)c1] | $[\alpha]_D^{20} = +58.5°$ |

TABLE-continued compounds prepared as described above

| Compound | Structure | Optical rotation |
|---|---|---|
| 12B | 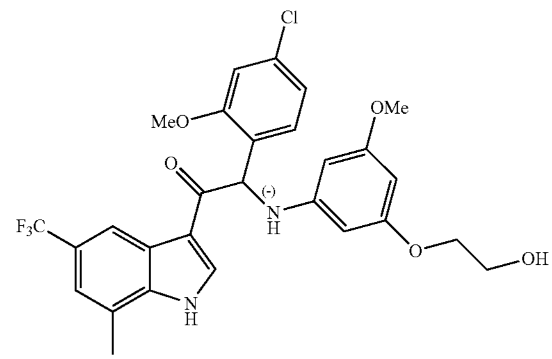 [SMILES: COc1cc(NC(C(=O)c2c[nH]c3c(C)cc(C(F)(F)F)cc23)c2ccc(Cl)cc2OC)cc(OCCO)c1] | $[\alpha]_D^{20} = -55.7°$ |
| 13 | 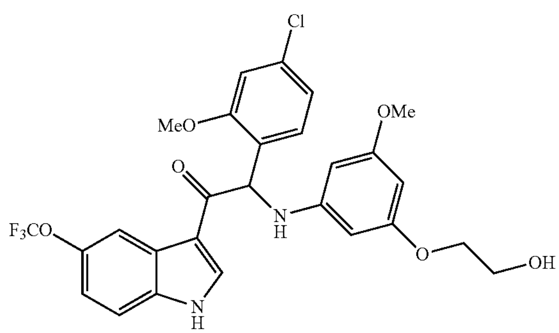 [SMILES: COc1cc(NC(C(=O)c2c[nH]c3ccc(OC(F)(F)F)cc23)c2ccc(Cl)cc2OC)cc(OCCO)c1] | racemic |
| 13A | 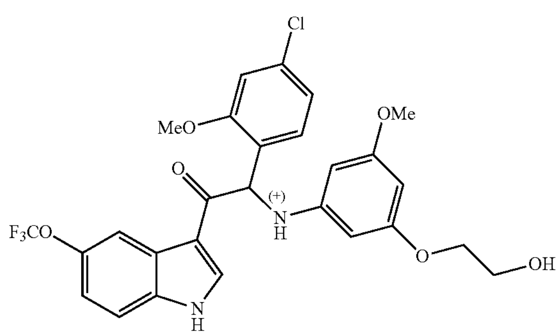 | $[\alpha]_D^{20} = +108.5°$ |
| 13B | 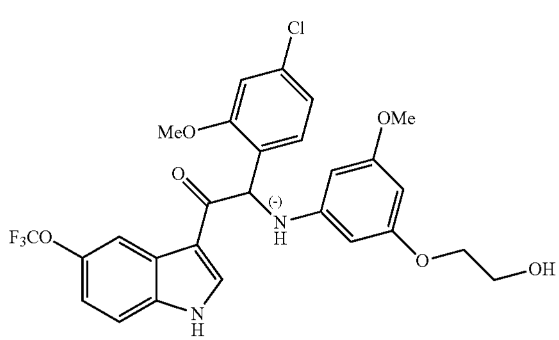 | $[\alpha]_D^{20} = -107.4°$ |

TABLE-continued compounds prepared as described above

| Compound | Structure | Optical rotation |
|---|---|---|
| 14 | 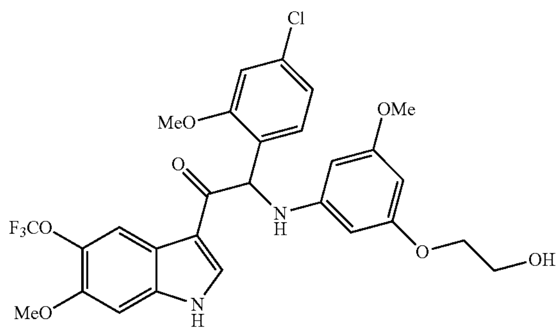 [SMILES: COc1cc(NC(C(=O)c2c[nH]c3cc(OC)c(OC(F)(F)F)cc23)c2ccc(Cl)cc2OC)cc(OCCO)c1] | racemic |
| 14A | 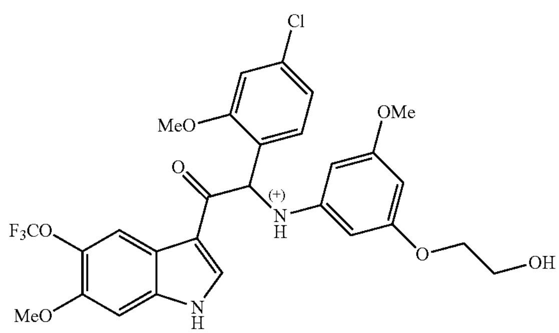 [SMILES: COc1cc(NC(C(=O)c2c[nH]c3cc(OC)c(OC(F)(F)F)cc23)c2ccc(Cl)cc2OC)cc(OCCO)c1] | $[\alpha]_D^{20} = +81.7°$ |
| 14B | 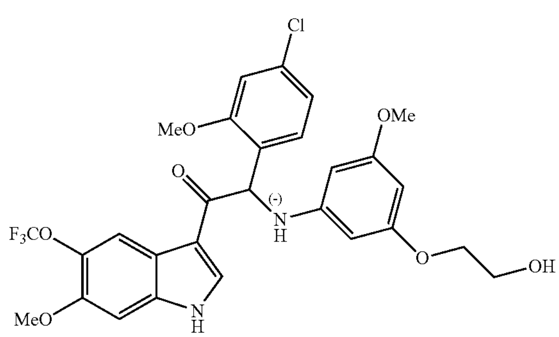 | $[\alpha]_D^{20} = -82.5°$ |
| 15 | 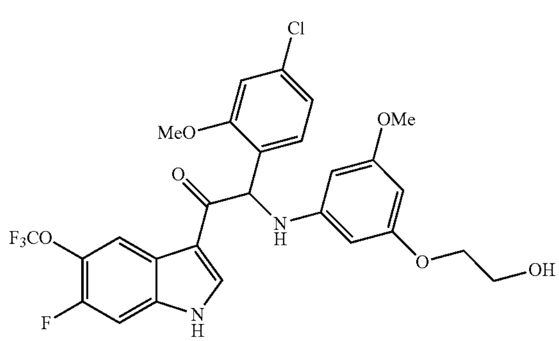 | racemic |

TABLE-continued compounds prepared as described above

| Compound | Structure | Optical rotation |
|---|---|---|
| 15A | 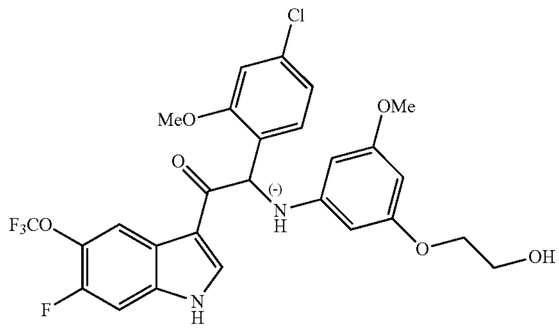 | $[\alpha]_D^{20} = -69.9°$ |
| 15B | 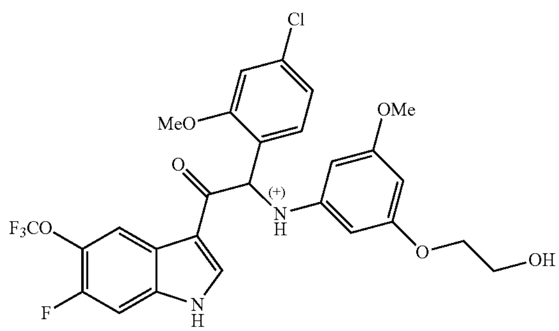 | $[\alpha]_D^{20} = +91.8°$ |
| 16 | 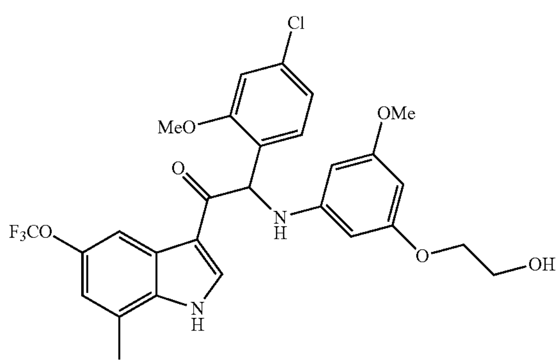 | racemic |
| 16A | 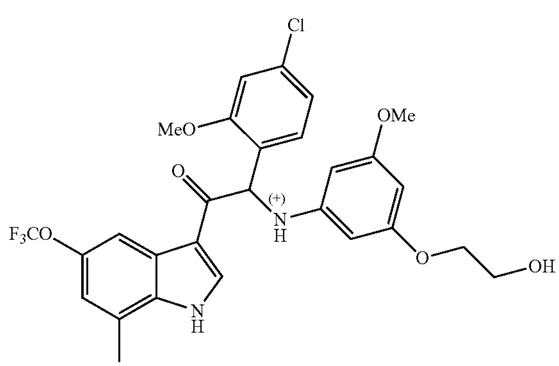 | $[\alpha]_D^{20} = +82.4°$ |

TABLE-continued compounds prepared as described above

| Compound | Structure | Optical rotation |
|---|---|---|
| 16B | (structure shown) | $[\alpha]_D^{20} = -82.0°$ |

Antiviral Activity of the Compounds of the Invention
DENV-2 Antiviral Assay

The antiviral activity of all the compounds of the invention was tested against the DENV-2 16681 strain which was labeled with enhanced green fluorescent protein (eGPF). The culture medium consists of minimal essential medium supplemented with 2% of heat-inactivated fetal calf serum, 0.04% gentamycin (50 mg/mL) and 2 mM of L-glutamine. Vero cells, obtained from ECACC, were suspended in culture medium and 25 µL was added to 384-well plates (2500 cells/well), which already contain the antiviral compounds. Typically, these plates contain a 5-fold serial dilution of 9 dilution steps of the test compound at 200 times the final concentration in 100% DMSO (200 nL). In addition, each compound concentration is tested in quadruplicate (final concentration range: 25 µM-0.000064 µM or 2.5 µM-0.0000064 µM for the most active compounds). Finally, each plate contains wells which are assigned as virus controls (containing cells and virus in the absence of compound), cell controls (containing cells in the absence of virus and compound) and medium controls (containing medium in the absence of cells, virus and compounds). To the wells assigned as medium control, 25 µL of culture medium added instead of Vero cells. Once the cells were added to the plates, the plates were incubated for 30 minutes at room temperature to allow the cells to distribute evenly within the wells. Next, the plates were incubated in a fully humidified incubator (37° C., 5% $CO_2$) until the next day. Then, DENV-2 strain 16681, labeled with eGFP, was added at a multiplicity of infection (MOI) of 0.5. Therefore, 15 µL of virus suspension was added to all the wells containing test compound and to the wells assigned as virus control. In parallel, 15 µL of culture medium was added to the medium and cell controls. Next, the plates were incubated for 3 days in a fully humidified incubator (37° C., 5% $CO_2$). At the day of the read out, the eGFP fluorescence was measured using an automated fluorescence microscope at 488 nm (blue laser). Using an in-house LIMS system, inhibition dose response curves for each compound were calculated and the half maximal effective concentration ($EC_{50}$) was determined. Therefore, the percent inhibition (I) for every test concentration is calculated using the following formula: $I=100*(S_T-S_{CC})/(S_{VC}-S_{CC})$; $S_T$, $S_{CC}$ and $S_{VC}$ are the amount of eGFP signal in the test compound, cell control and virus control wells, respectively. The $EC_{50}$ represents the concentration of a compound at which the virus replication is inhibited with 50%, as measured by a 50% reduction of the eGFP fluorescent intensity compared to the virus control. The $EC_{50}$ is calculated using linear interpolation (Table 1).

In parallel, the toxicity of the compounds was assessed on the same plates. Once the read-out for the eGFP signal was done, 40 µL of ATPlite, a cell viability stain, was added to all wells of the 384-well plates. ATP is present in all metabolically active cells and the concentration declines very rapidly when the cells undergo necrosis or apoptosis. The ATPLite assay system is based on the production of light caused by the reaction of ATP with added luciferase and D-luciferin. The plates were incubated for 10 minutes at room temperature. Next, the plates were measured on a ViewLux. The half maximal cytotoxic concentration ($CC_{50}$) was also determined, defined as the concentration required to reduce the luminescent signal by 50% compared to that of the cell control wells. Finally, the selectivity index (SI) was determined for the compounds, which was calculated as followed: $SI=CC_{50}/EC_{50}$.

TABLE 1

$EC_{50}$, $CC_{50}$, and SI for the compounds of the invention in the DENV-2 antiviral assay

| compound# | $EC_{50}$ (µM) | N | $CC_{50}$ (µM) | N | SI | N |
|---|---|---|---|---|---|---|
| 1 | 0.0012 | 3 | 5.5 | 3 | 4730 | 3 |
| 1A | 0.064 | 3 | 6.8 | 3 | 106 | 3 |
| 1B | 0.00062 | 4 | 3.3 | 5 | 4840 | 4 |
| 2 | 0.00071 | 3 | 4.8 | 3 | 6770 | 3 |
| 2A | 0.00045 | 4 | 3.5 | 4 | 8240 | 4 |
| 2B | 0.024 | 3 | 6.8 | 3 | 287 | 3 |
| 3 | 0.00099 | 3 | 3.0 | 4 | 3220 | 3 |
| 3A | 0.00047 | 3 | 2.4 | 3 | 5050 | 3 |
| 3B | 0.015 | 3 | 7.8 | 3 | 511 | 3 |
| 4 | 0.00062 | 3 | 6.1 | 3 | 13100 | 3 |
| 4A | 0.063 | 3 | 11 | 3 | 172 | 3 |
| 4B | 0.00046 | 3 | 2.5 | 3 | 7070 | 3 |
| 5 | 0.00050 | 4 | 4.5 | 4 | 10300 | 3 |
| 5A | 0.030 | 3 | 5.4 | 3 | 181 | 3 |
| 5B | 0.00030 | 3 | 3.3 | 3 | >9300 | 3 |
| 6 | 0.00084 | 3 | 3.6 | 3 | 5560 | 3 |
| 6A | 0.00033 | 3 | >2.5 | 3 | >7560 | 3 |
| 6B | 0.098 | 3 | 10 | 3 | 124 | 3 |
| 7A | 0.025 | 3 | 6.7 | 3 | 270 | 3 |
| 7B | 0.00053 | 4 | 2.4 | 5 | 4580 | 4 |
| 8 | 0.00041 | 3 | 4.7 | 5 | 11800 | 3 |
| 8A | 0.00035 | 3 | 2.9 | 3 | 8380 | 3 |
| 8B | 0.031 | 3 | 6.0 | 3 | 195 | 3 |

TABLE 1-continued

EC$_{50}$, CC$_{50}$, and SI for the compounds of the invention in the DENV-2 antiviral assay

| compound# | EC$_{50}$ (μM) | N | CC$_{50}$ (μM) | N | SI | N |
|---|---|---|---|---|---|---|
| 9 | 0.00029 | 3 | 2.5 | 3 | 17600 | 3 |
| 9A | 0.012 | 3 | 3.5 | 3 | >225 | 3 |
| 9B | 0.00018 | 6 | 3.3 | 7 | >20100 | 6 |
| 10 | 0.00027 | 3 | 3.2 | 3 | >9920 | 3 |
| 11A | 0.00033 | 3 | 2.5 | 3 | 7820 | 3 |
| 11B | 0.015 | 3 | 2.7 | 3 | 181 | 3 |
| 12A | 0.00016 | 3 | 2.6 | 4 | 21500 | 3 |
| 12B | 0.038 | 3 | 11 | 4 | 294 | 3 |
| 13A | 0.00014 | 7 | 2.6 | 6 | 23000 | 6 |
| 13B | 0.0072 | 5 | 5.8 | 5 | 643 | 5 |
| 14 | 0.00034 | 3 | 3.5 | 3 | >8340 | 3 |
| 14A | 0.00017 | 3 | 2.5 | 3 | 18500 | 3 |
| 14B | 0.0072 | 3 | 5.4 | 3 | 754 | 3 |
| 15A | 0.0099 | 3 | 3.8 | 3 | 386 | 3 |
| 15B | 0.00029 | 3 | 2.6 | 3 | 10200 | 3 |
| 16 | 0.00019 | 6 | 2.5 | 6 | >39200 | 6 |
| 16A | 0.000098 | 7 | 2.4 | 7 | >45000 | 7 |
| 16B | 0.015 | 3 | 3.6 | 3 | 236 | 3 |

N = the number of independent experiments in which the compounds were tested.

Tetravalent Reverse Transcriptase Quantitative-PCR (RT-qPCR) Assay

The antiviral activity of the compounds of the invention was tested against DENV-1 strain TC974 #666 (NCPV), DENV-2 strain 16681, DENV-3 strain H87 (NCPV) and DENV-4 strain H241 (NCPV) in a RT-qPCR assay. Therefore, Vero cells were infected with either DENV-1, or -2, or -3, or -4 in the presence or absence of test compounds. At day 3 post-infection, the cells were lysed and cell lysates were used to prepare cDNA of both a viral target (the 3'UTR of DENV; Table 2) and cellular reference gene (β-actin, Table 2). Subsequently, a duplex real time PCR was performed on a Lightcycler480 instrument. The generated Cp value is inversely proportional to the amount of RNA expression of these targets. Inhibition of DENV replication by a test compound results in a shift of Cp's for the 3'UTR gene. On the other hand, if a test compound is toxic to the cells, a similar effect on β-actin expression will be observed. The comparative ΔΔCp method is used to calculate EC$_{50}$, which is based on the relative gene expression of the target gene (3'UTR) normalized with the cellular housekeeping gene (β-actin). In addition, CC$_{50}$ values are determined based on the C$_p$ values acquired for the housekeeping gene β-actin.

TABLE 2

Primers and probes used for the real-time, quantitative RT-PCR.

| Primer/probe | Target | Sequence[a, b] |
|---|---|---|
| F3utr258 | DENV 3'-UTR | 5'-CGGTTAGAGGAGACCCCTC-3' |
| R3utr425 | DENV 3'-UTR | 5'-GAGACAGCAGGATCTCTGGTC-3' |
| P3utr343 | DENV 3'-UTR | FAM-5'-AAGGACTAG-ZEN-AGGTTAGAGGAGACCCCCC-3'-IABkFQ |
| Factin743 | β-actin | 5'-GGCCAGGTCATCACCATT-3' |
| Ractin876 | β-actin | 5'-ATGTCCACGTCACACTTCATG-3' |
| Pactin773 | β-actin | HEX-5'-TTCCGCTGC-ZEN-CCTGAGGC TCTC-3'-IABkFQ |

[a]Reporter dyes (FAM, HEX) and quenchers (ZEN and IABkFQ) elements are indicated in bold and italics.
[b]The nucleotide sequence of the primers and probes were selected from the conserved region in the 3'UTR region of the dengue virus genome, based on the alignment of 300 nucleotide sequences of the four dengue serotypes deposited in Genbank (Gong et al., 2013, Methods Mol Biol, Chapter 16).

The culture medium consisted of minimal essential medium supplemented with 2% of heat-inactivated fetal calf serum, 0.04% gentamycin (50 mg/mL) and 2 mM of L-glutamine. Vero cells, obtained from ECACC, were suspended in culture medium and 75 μL/well was added in 96-well plates (10000 cells/well), which already contain the antiviral compounds. Typically, these plates contain a 5-fold serial dilution of 9 dilution steps of the test compound at 200 times the final concentration in 100% DMSO (500 nL; final concentration range: 25 μM-0.000064 μM or 2.5 μM-0.0000064 μM for the most active compounds). In addition, each plate contains wells which are assigned as virus controls (containing cells and virus in the absence of compound) and cell controls (containing cells in the absence of virus and compound). Once the cells were added in the plates, the plates were incubated in a fully humidified incubator (37° C., 5% CO$_2$) until the next day. Dengue viruses serotype-1, 2, 3 and 4 were diluted in order to obtain a Cp of ~22-24 in the assay. Therefore, 25 μL of virus suspension was added to all the wells containing test compound and to the wells assigned as virus control. In parallel, 25 μL of culture medium was added to the cell controls. Next, the plates were incubated for 3 days in a fully humidified incubator (37° C., 5% CO$_2$). After 3 days, the supernatant was removed from the wells and the cells were washed twice with ice-cold PBS (~100 μL). The cell pellets within the 96-well plates were stored at −80° C. for at least 1 day. Next, RNA was extracted using the Cells-to-CT™ lysis kit, according to the manufacturer's guideline (Life Technologies). The cell lysates can be stored at −80° C. or immediately used in the reverse transcription step.

In preparation of the reverse transcription step, mix A (table 3A) was prepared and 7.57 μL/well was dispensed in a 96-well plate. After addition of 5 μL of the cell lysates, a five minute denaturation step at 75° C. was performed (table 3B). Afterwards, 7.43 μL of mix B was added (table 3C) and the reverse transcription step was initiated (table 3D) to generate cDNA.

Finally, a RT-qPCR mix was prepared, mix C (table 4A), and 22.02 μL/well was dispensed in 96-well LightCycler qPCR plates to which 3 μL of cDNA was added and the qPCR was performed according to the conditions in table 4B on a LightCycler 480.

Using the LightCycler software and an in-house LIMS system, dose response curves for each compound were calculated and the half maximal effective concentration (EC$_{50}$) and the half maximal cytotoxic concentration (CC$_{50}$) were determined (Tables 5-8).

TABLE 3 cDNA synthesis using Mix A, denaturation, Mix B and reverse transcription

A
Mix A

Plates 8
Samples 828                    Reaction Vol. (µl) 20

| Mix Item | Unit | Concentration Stock | Final | Volume for (µl) 1 sample | x samples |
|---|---|---|---|---|---|
| Milli-Q H$_2$O | | | | 7.27 | 6019.56 |
| R3utr425 | µM | 20 | 0.27 | 0.15 | 124.20 |
| Ractin876 | µM | 20 | 0.27 | 0.15 | 124.20 |
| | | Volume mix/well (µl) | | 7.57 | |
| | | Cell lysates | | 5.00 | |

B
Denaturation step:

| Step | Temp | Time |
|---|---|---|
| Denaturation | 75° C. | 5' |
| Hold | 4° C. | hold |

C
Mix B

Samples 864

| Mix Item | Unit | Concentration Stock | Final | Volume for (µl) 1 sample | x samples |
|---|---|---|---|---|---|
| Expand HIFI buffer 2 | X | 10.00 | 1.00 | 2.00 | 1728.0 |
| MgCl$_2$ | mM | 25.00 | 3.50 | 2.80 | 2419.2 |
| dNTPs | mM | 10.00 | 1.00 | 2.00 | 1728.0 |
| Rnase inhibitor | U/µl | 40.00 | 1.00 | 0.50 | 432.0 |
| Expand RT | U/µl | 50.00 | 0.33 | 0.13 | 112.3 |
| | | Total Volume Mix (µl) | | 7.43 | |

D
Protocol cDNA synthesis

| Step | Temp | Time |
|---|---|---|
| Rev transc | 42° C. | 30' |
| Denaturation | 99° C. | 5' |
| Hold | 4° C. | hold |

TABLE 4 qPCR mix and protocol.

A
Mix C

Samples 833                    Reaction Vol. (µl) 25

| Mix Item | Unit | Concentration Stock | Final | Volume for (µl) 1 sample | x samples |
|---|---|---|---|---|---|
| H$_2$O PCR grade Roche | | | | 7.74 | 6447.42 |
| Roche 2xMM mix | X | 2 | 1 | 12.50 | 10412.50 |
| F3utr258 | µM | 20 | 0.3 | 0.38 | 316.54 |
| R3utr425 | µM | 20 | 0.3 | 0.38 | 316.54 |
| P3utr343 | µM | 20 | 0.1 | 0.13 | 108.29 |
| Factin743 | µM | 20 | 0.3 | 0.38 | 316.54 |
| Ractin876 | µM | 20 | 0.3 | 0.38 | 316.54 |
| Pactin773 | µM | 20 | 0.1 | 0.13 | 108.29 |
| | | Volume Mix/Tube (µl) | | 22.02 | |
| | | cDNA | | 3.00 | |

B
Protocol qPCR3

| Step | Temp | Time | Ramp rate | |
|---|---|---|---|---|
| preincub/denat | 95° C. | 10 min | 4.4 | |
| Denaturation | 95° C. | 10 sec | 4.4 | 40 cycles |
| annealing | 58° C. | 1 min | 2.2 | |
| Elongation | 72° C. | 1 sec | 4.4 | |
| Cooling | 40° C. | 10 sec | 1.5 | |

TABLE 5

EC$_{50}$, CC$_{50}$, and SI for the compounds against serotype 1 in the RT-qPCR assays Protocol A
RT-qPCR serotype 1 TC974#666

| compound# | EC$_{50}$ (µM) | N | CC$_{50}$ (µM) | N | SI | N |
|---|---|---|---|---|---|---|
| 1B | 0.0013 | 3 | 3.3 | 3 | 2360 | 3 |
| 2A | 0.0022 | 4 | >2.5 | 3 | >2130 | 3 |
| 3A | 0.0021 | 3 | >2.5 | 3 | >2880 | 3 |
| 4B | 0.0014 | 3 | >2.5 | 3 | >3960 | 3 |
| 5B | 0.00077 | 3 | >2.5 | 3 | >3410 | 3 |
| 6A | 0.0026 | 3 | >2.1 | 3 | 910 | 3 |
| 7B | 0.0012 | 3 | >2.5 | 3 | >5240 | 3 |
| 8A | 0.00071 | 4 | 2.1 | 4 | 3010 | 4 |
| 9B | 0.00088 | 4 | >2.0 | 4 | >3440 | 3 |
| 11A | 0.00069 | 3 | >2.5 | 3 | >7140 | 3 |
| 12A | 0.00040 | 3 | >2.5 | 2 | >7400 | 2 |
| 13A | 0.00051 | 3 | 1.2 | 3 | 1940 | 3 |
| 14A | 0.00092 | 3 | >2.1 | 3 | 3680 | 3 |
| 15B | 0.00046 | 3 | 1.5 | 3 | 4720 | 3 |
| 16A | 0.00063 | 3 | >2.5 | 3 | >12400 | 3 |

N = the number of independent experiments in which the compounds were tested.

TABLE 6

EC$_{50}$, CC$_{50}$, and SI for the compounds against serotype 2 in the RT-qPCR assays Protocol A
RT-qPCR serotype 2 16681

| compound# | EC$_{50}$ (µM) | N | CC$_{50}$ (µM) | N | SI | N |
|---|---|---|---|---|---|---|
| 1B | 0.00041 | 3 | 3.5 | 3 | 7070 | 2 |
| 2A | 0.00025 | 4 | 3.2 | 5 | >10100 | 4 |
| 3A | 0.00046 | 3 | 2.6 | 3 | >5460 | 3 |
| 4B | 0.00036 | 3 | >2.4 | 3 | 14000 | 3 |
| 5B | 0.00036 | 3 | 3.2 | 3 | >7530 | 3 |
| 6A | 0.00055 | 3 | 3.9 | 3 | 6430 | 3 |
| 7B | 0.00055 | 3 | >2.5 | 3 | >8710 | 3 |
| 8A | 0.00031 | 5 | 3.7 | 6 | >10700 | 4 |
| 9B | 0.00027 | 3 | 3.4 | 5 | >13300 | 3 |
| 11A | 0.00024 | 3 | >2.5 | 3 | >13400 | 3 |
| 12A | 0.00022 | 3 | >2.5 | 3 | >15400 | 3 |
| 13A | 0.00020 | 3 | 2.6 | 4 | 19700 | 3 |
| 14A | 0.00017 | 3 | 3.8 | 3 | 25800 | 3 |
| 15B | 0.00015 | 3 | >2.1 | 3 | 18600 | 3 |
| 16A | 0.00015 | 3 | >2.5 | 3 | >32000 | 3 |

N = the number of independent experiments in which the compounds were tested.

TABLE 7

EC$_{50}$, CC$_{50}$, and SI for the compounds against serotype 3 in the RT-qPCR assays

| | Protocol A RT-qPCR serotype 3 H87 | | | | | |
|---|---|---|---|---|---|---|
| compound# | EC$_{50}$ (µM) | N | CC$_{50}$ (µM) | N | SI | N |
| 1B | 0.014 | 4 | 3.2 | 4 | 241 | 4 |
| 2A | 0.019 | 4 | >1.9 | 4 | >158 | 4 |
| 3A | 0.018 | 3 | >2.5 | 3 | >203 | 3 |
| 4B | 0.0092 | 3 | >2.5 | 3 | >317 | 3 |
| 5B | 0.0060 | 3 | >2.5 | 2 | >425 | 2 |
| 6A | 0.012 | 3 | >2.5 | 3 | >312 | 3 |
| 7B | 0.0082 | 3 | >2.5 | 3 | >460 | 3 |
| 8A | 0.0058 | 4 | >2.4 | 3 | 530 | 3 |
| 9B | 0.0063 | 3 | >2.5 | 3 | 456 | 3 |
| 11A | 0.0057 | 3 | >2.5 | 3 | >741 | 3 |
| 12A | 0.0039 | 3 | >2.5 | 3 | >862 | 3 |
| 13A | 0.0035 | 3 | >2.5 | 2 | >1010 | 2 |
| 14A | 0.0051 | 3 | >2.3 | 3 | 534 | 3 |
| 15B | 0.0032 | 3 | >2.4 | 3 | 1130 | 3 |
| 16A | 0.0017 | 3 | >2.5 | 3 | >1650 | 3 |

N = the number of independent experiments in which the compounds were tested.

TABLE 8

EC$_{50}$, CC$_{50}$, and SI for the compounds against serotype 4 in the RT-qPCR assays

| | Protocol A RT-qPCR serotype 4 H241 | | | | | |
|---|---|---|---|---|---|---|
| compound# | EC$_{50}$ (µM) | N | CC$_{50}$ (µM) | N | SI | N |
| 1B | 0.050 | 4 | 2.6 | 3 | 48 | 3 |
| 2A | 0.062 | 5 | >2.1 | 5 | >34 | 5 |
| 3A | 0.062 | 3 | >2.5 | 2 | >63 | 2 |
| 4B | 0.051 | 3 | >2.1 | 3 | >41 | 3 |
| 5B | 0.050 | 3 | 2.4 | 2 | 34 | 2 |
| 6A | 0.078 | 3 | 1.5 | 3 | 19 | 3 |
| 7B | 0.052 | 4 | 2.1 | 4 | 40 | 4 |
| 8A | 0.048 | 8 | 2.6 | 8 | 58 | 8 |
| 9B | 0.050 | 4 | 2.7 | 4 | 62 | 4 |
| 11A | 0.039 | 4 | 1.9 | 4 | 50 | 4 |
| 12A | 0.030 | 4 | >2.4 | 4 | 91 | 4 |
| 13A | 0.020 | 4 | >2.5 | 1 | >121 | 1 |
| 14A | 0.025 | 3 | 1.6 | 3 | 75 | 3 |
| 15B | 0.031 | 4 | 1.6 | 4 | 47 | 4 |
| 16A | 0.017 | 3 | >2.0 | 3 | >84 | 3 |

N = the number of independent experiments in which the compounds were tested.

PRIOR ART EXAMPLE

Compound (350) disclosed in WO-2013/045516 has been tested in an analogous DENV-2 antiviral assay as the compounds of the present invention and their reported activity is listed below.

compound (350) of WO-2013/045516

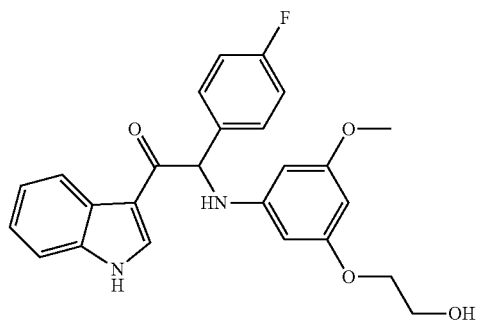

TABLE 9

EC$_{50}$, CC$_{50}$, and SI for compound (350) disclosed in the DENV-2 antiviral assay

| compound# | EC$_{50}$ (µM) | CC$_{50}$ (µM) | SI |
|---|---|---|---|
| (350) of WO-2013/045516 | 0.01 | 46 | 3462 |

The invention claimed is:

1. A compound selected from the group consisting of: formula (Ia or Ib)

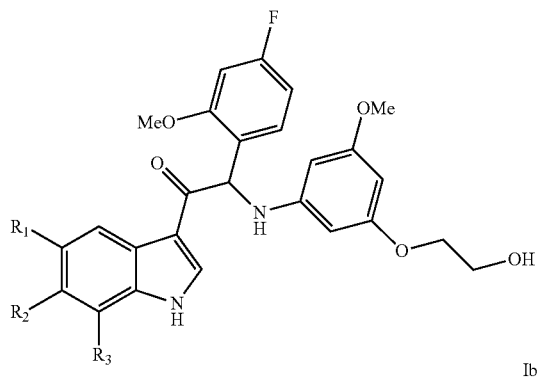

a stereoisomeric form, a pharmaceutically acceptable salt, solvate and polymorph thereof comprising a mono- or di-substituted indole group; said compound is selected from the group wherein:

$R_1$ is $CF_3$ or $OCF_3$, $R_2$ is H or $OCH_3$ or F, $R_3$ is H; and when $R_2$ is H then $R_3$ can also be $CH_3$.

2. The compound of claim 1 selected from the group consisting of:

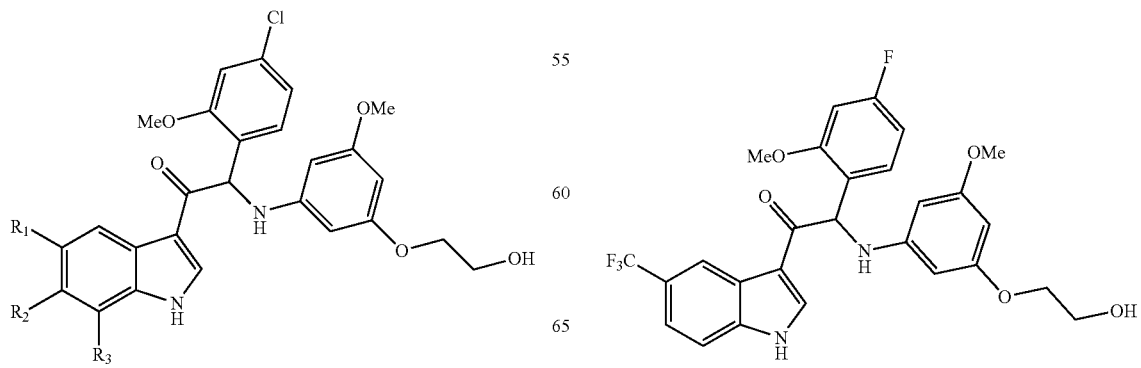

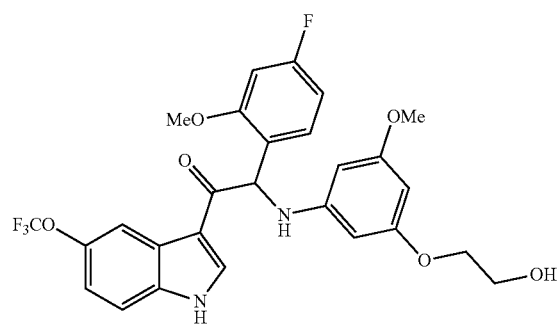
5
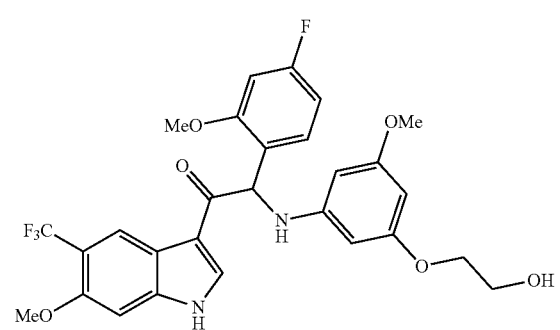
2
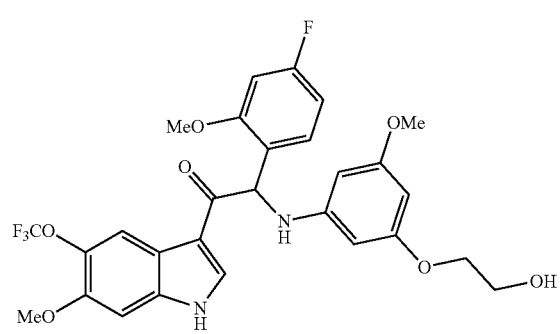
6
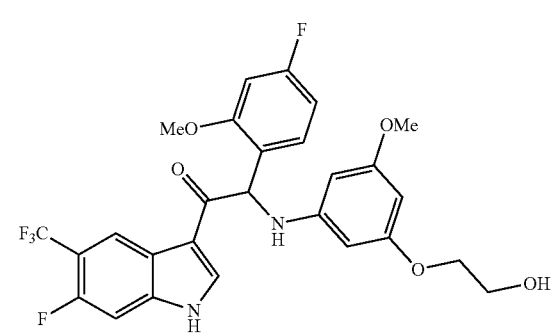
3
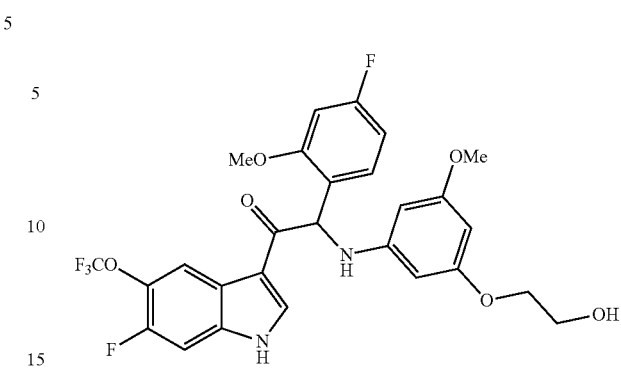
7
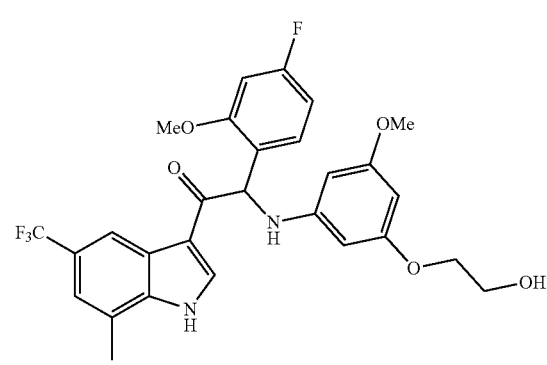
4
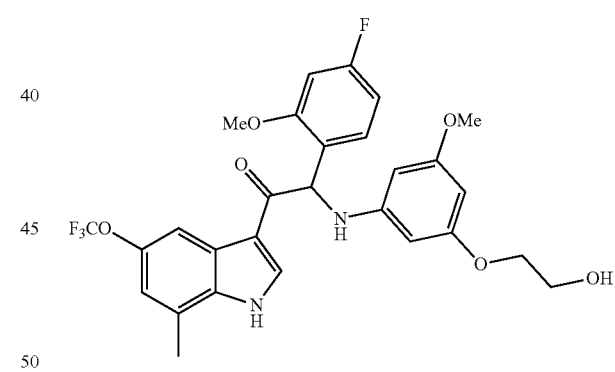
8
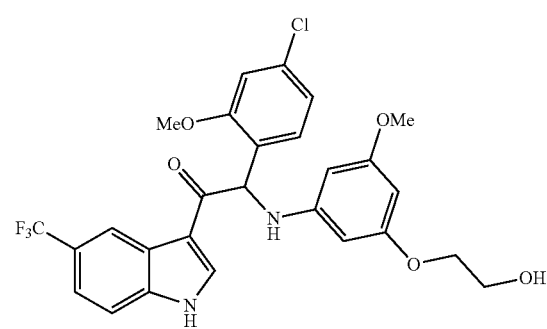
9

13
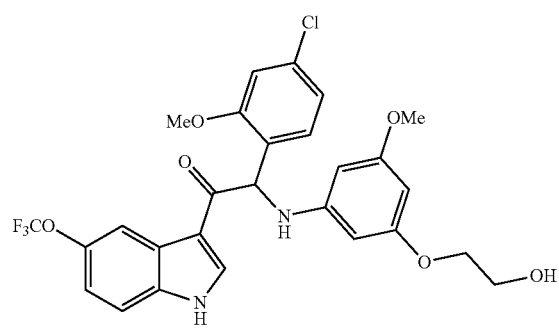
14
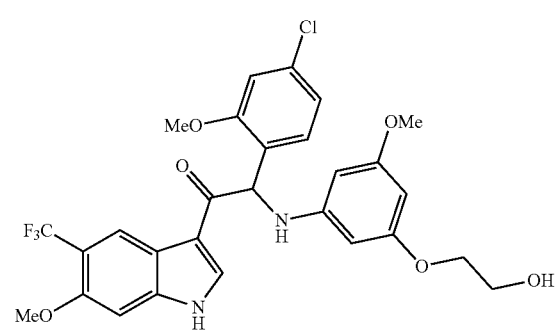
11
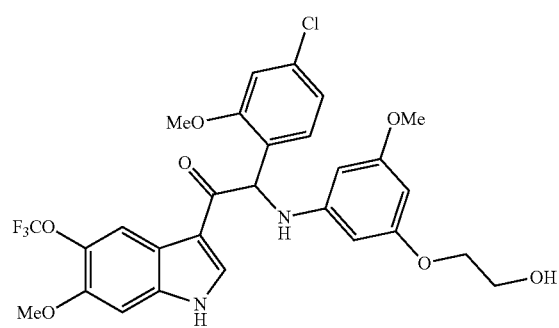
15
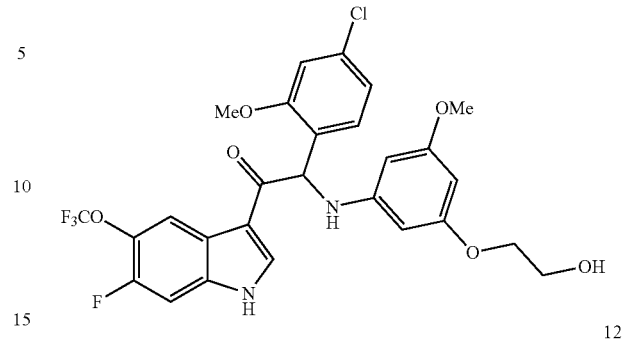
12
16
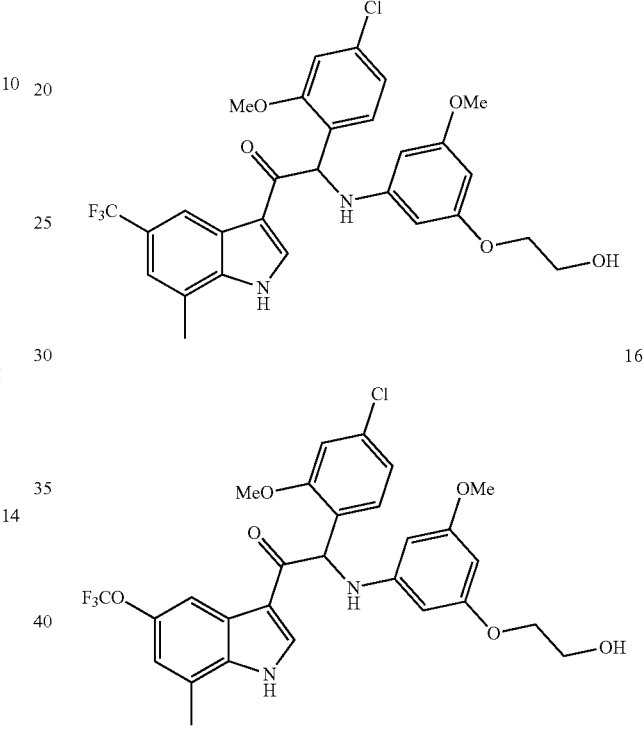
or stereoisomeric form, a pharmaceutically acceptable salt, solvate or polymorph thereof.
3. A pharmaceutical composition comprising a compound of claim 1 together with one or more pharmaceutically acceptable excipients, diluents or carriers.
4. The compound of claim 1 selected from the group consisting of:
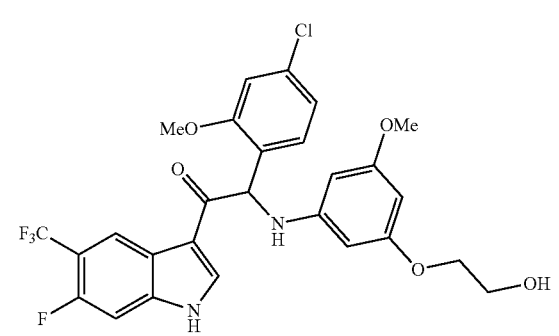
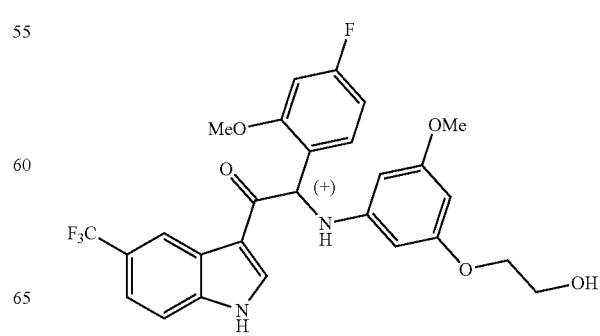

99
-continued
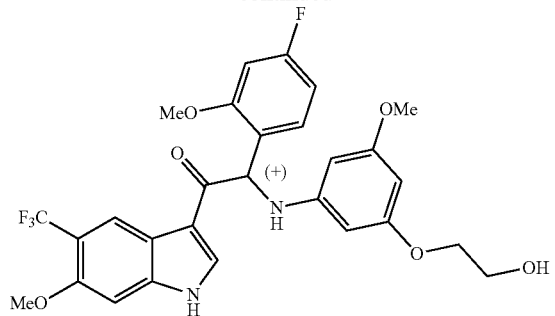
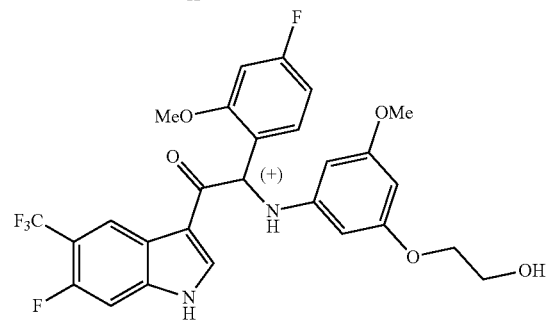
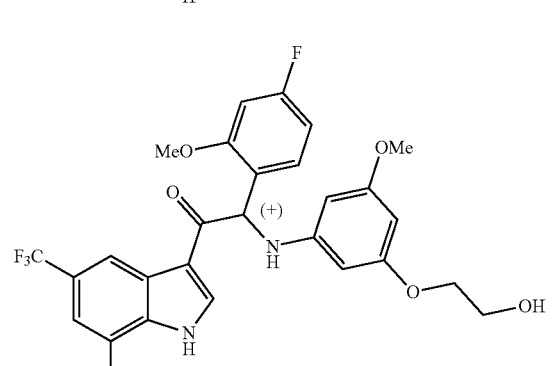
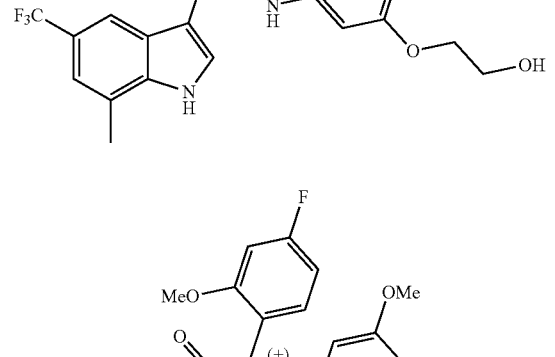
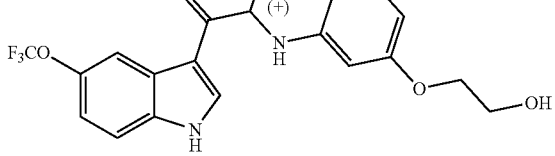
100
-continued
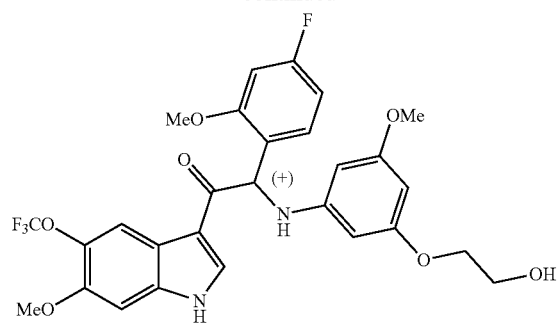
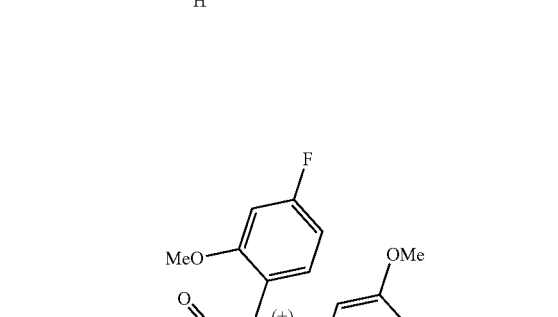
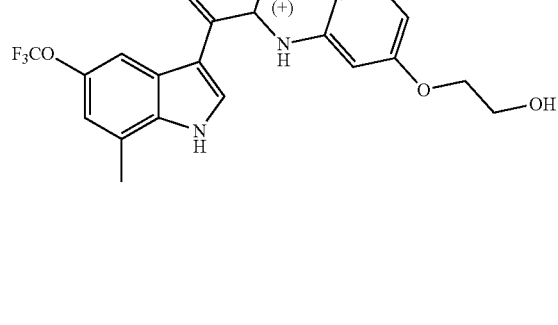
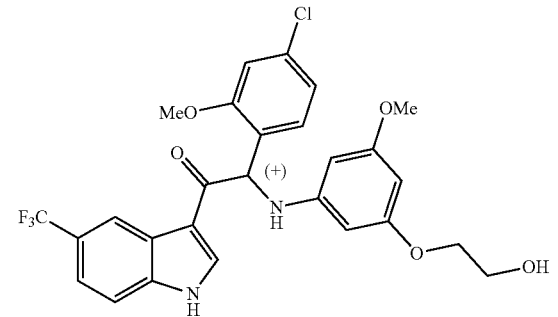
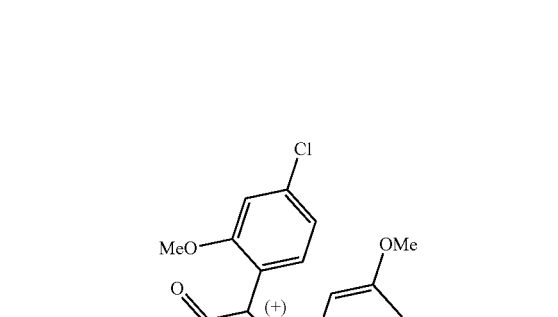

-continued

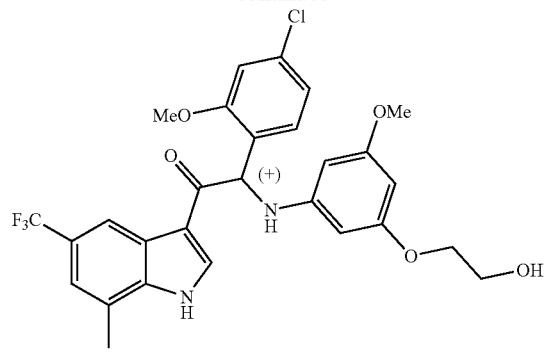

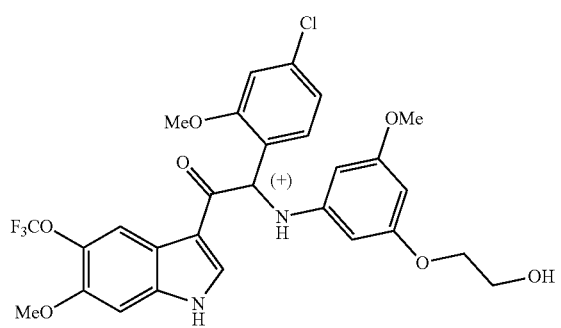

-continued

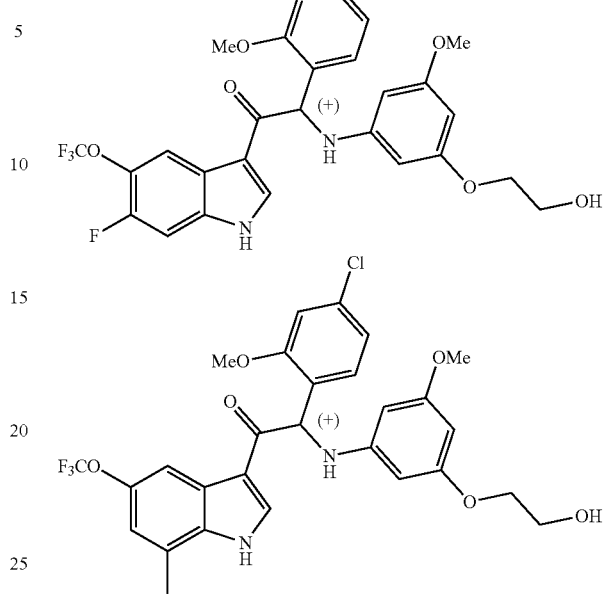

or a pharmaceutically acceptable salt, solvate or polymorph thereof.

5. A pharmaceutical composition comprising a compound of claim 4 together with one or more pharmaceutically acceptable excipients, diluents or carriers.

6. A method of inhibiting the replication of dengue virus comprising contacting a compound of claim 1 with dengue virus.

7. A method of treating dengue virus infection comprising administering a pharmaceutical composition of claim 3 to a patient.

* * * * *